United States Patent
Halbig et al.

(10) Patent No.: US 12,226,614 B2
(45) Date of Patent: Feb. 18, 2025

(54) AUTO-INJECTOR AND RELATED METHODS OF USE

(71) Applicant: Regeneron Pharmaceuticals, Inc., Tarrytown, NY (US)

(72) Inventors: Daniel Halbig, Ballston Lake, NY (US); Bryan Grygus, Clifton Park, NY (US); Trevor Langley, Rensselaer, NY (US); Andrew Dumont, Rensselaer, NY (US); Bart E. Burgess, Bernville, PA (US); Matthew Pausley, Gansevoort, NY (US); Ross Kenyon, Saratoga Springs, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/565,237

(22) Filed: Dec. 29, 2021

(65) Prior Publication Data
US 2022/0203032 A1 Jun. 30, 2022

Related U.S. Application Data

(60) Provisional application No. 63/134,554, filed on Jan. 6, 2021, provisional application No. 63/133,185, filed on Dec. 31, 2020.

(51) Int. Cl.
*A61M 5/20* (2006.01)
*A61M 5/145* (2006.01)
(Continued)

(52) U.S. Cl.
CPC ...... *A61M 5/2053* (2013.01); *A61M 5/14526* (2013.01); *A61M 5/16881* (2013.01);
(Continued)

(58) Field of Classification Search
CPC .............. A61M 5/2053; A61M 5/2033; A61M 2005/206; A61M 2005/2073;
(Continued)

(56) References Cited

U.S. PATENT DOCUMENTS

| 2,685,383 A | 8/1954 | Kochner |
| 3,395,704 A | 8/1968 | Max et al. |

(Continued)

FOREIGN PATENT DOCUMENTS

| AU | 2005231753 A1 | 10/2005 |
| BR | 112018068240 A2 | 1/2019 |

(Continued)

OTHER PUBLICATIONS

International Search Report in International Application No. PCT/US2020/040729, dated Sep. 12, 2020 (7 pages).

(Continued)

*Primary Examiner* — Michael J Tsai
*Assistant Examiner* — Nidah Hussain
(74) *Attorney, Agent, or Firm* — Bookoff McAndrews, PLLC

(57) ABSTRACT

An auto-injector may include a container capable of comprising a medicament; a shuttle coupled to the container and on a horizontal path with a first state and a second state; an energy source configured to release energy to translate the container and to translate the shuttle, preferably the energy source is pressurized fluid from a can; an impediment preventing horizontal movement of the shuttle before activation of the auto-injector; and a needle having a first end configured to extend out of the auto-injector, and a second end configured to extend into the container, wherein the second end of the needle and the container are not in fluid communication with one another before activation of the auto-injector.

20 Claims, 48 Drawing Sheets

(51) Int. Cl.
*A61M 5/168* (2006.01)
*A61M 5/24* (2006.01)

(52) U.S. Cl.
CPC ........ *A61M 5/2033* (2013.01); *A61M 5/2466* (2013.01); *A61M 2005/14513* (2013.01); *A61M 2005/206* (2013.01)

(58) Field of Classification Search
CPC ........... A61M 2005/2013; A61M 2005/31508; A61M 5/3202; A61M 5/2046; A61M 5/34; A61M 5/583; A61M 5/14248; A61M 2205/581; A61M 5/2429; A61M 5/283
USPC ....................................................... 604/136
See application file for complete search history.

(56) References Cited

U.S. PATENT DOCUMENTS

| | | |
|---|---|---|
| 5,527,288 A | 6/1996 | Gross et al. |
| 5,713,876 A | 2/1998 | Bogert et al. |
| 5,848,991 A | 12/1998 | Gross et al. |
| 5,997,501 A | 12/1999 | Gross et al. |
| 6,186,982 B1 | 2/2001 | Gross et al. |
| 6,290,683 B1 | 9/2001 | Erez et al. |
| 6,500,150 B1 | 12/2002 | Gross et al. |
| 6,595,956 B1 | 7/2003 | Gross et al. |
| 6,620,133 B1 | 9/2003 | Steck |
| 6,673,035 B1 | 1/2004 | Rice et al. |
| 6,682,504 B2 | 1/2004 | Nelson et al. |
| 6,824,529 B2 | 11/2004 | Gross et al. |
| 6,830,560 B1 | 12/2004 | Gross et al. |
| 6,843,388 B1 | 1/2005 | Hollars |
| 6,843,782 B2 | 1/2005 | Gross et al. |
| 6,960,184 B2 | 11/2005 | Willis et al. |
| 7,156,257 B2 | 1/2007 | De La Serna |
| 7,314,211 B2 | 1/2008 | Vallon et al. |
| 7,416,540 B2 | 8/2008 | Edwards et al. |
| 7,449,012 B2 | 11/2008 | Young et al. |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,731,686 B2 | 6/2010 | Edwards et al. |
| 7,731,690 B2 | 6/2010 | Edwards et al. |
| 7,740,607 B2 | 6/2010 | Willis et al. |
| 7,749,194 B2 | 7/2010 | Edwards et al. |
| 7,758,550 B2 | 7/2010 | Bollenbach et al. |
| 7,824,373 B2 | 11/2010 | Kim et al. |
| 7,857,167 B1 | 12/2010 | Hollars |
| 7,918,823 B2 | 4/2011 | Edwards et al. |
| 7,947,017 B2 | 5/2011 | Edwards et al. |
| 8,016,788 B2 | 9/2011 | Edwards et al. |
| 8,021,344 B2 | 9/2011 | Edwards et al. |
| 8,028,858 B2 | 10/2011 | Hollars |
| 8,105,281 B2 | 1/2012 | Edwards et al. |
| 8,118,777 B2 | 2/2012 | Ducharme et al. |
| 8,123,719 B2 | 2/2012 | Edwards et al. |
| 8,172,082 B2 | 5/2012 | Edwards et al. |
| 8,172,797 B2 | 5/2012 | Högdahl |
| 8,206,351 B2 | 6/2012 | Sugimoto et al. |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,303,535 B2 | 11/2012 | Both et al. |
| 8,313,463 B2 | 11/2012 | Barrow-Williams et al. |
| 8,313,466 B2 | 11/2012 | Edwards et al. |
| 8,343,110 B2 | 1/2013 | Harrison et al. |
| 8,361,026 B2 | 1/2013 | Edwards et al. |
| 8,361,029 B2 | 1/2013 | Edwards et al. |
| 8,361,054 B2 | 1/2013 | Ducharme et al. |
| 8,414,533 B2 | 4/2013 | Alexandersson |
| 8,425,462 B2 | 4/2013 | Edwards et al. |
| 8,480,624 B2 | 7/2013 | Kim et al. |
| 8,544,645 B2 | 10/2013 | Edwards et al. |
| 8,551,071 B2 | 10/2013 | Hwang et al. |
| 8,608,698 B2 | 12/2013 | Edwards et al. |
| 8,622,973 B2 | 1/2014 | Edwards et al. |
| 8,627,816 B2 | 1/2014 | Edwards et al. |
| 8,636,704 B2 | 1/2014 | Shang et al. |
| 8,668,670 B2 | 3/2014 | Bicknell et al. |
| 8,679,061 B2 | 3/2014 | Julian et al. |
| 8,690,827 B2 | 4/2014 | Edwards et al. |
| 8,708,958 B2 | 4/2014 | Kim et al. |
| 8,708,968 B2 | 4/2014 | Julian et al. |
| 8,728,032 B2 | 5/2014 | Ducharme et al. |
| 8,758,301 B2 | 6/2014 | Shang et al. |
| 8,814,834 B2 | 8/2014 | Sund et al. |
| 8,821,451 B2 | 9/2014 | Daniel |
| 8,887,720 B2 | 11/2014 | Fine et al. |
| 8,899,987 B2 | 12/2014 | Edwards et al. |
| 8,920,367 B2 | 12/2014 | Edwards et al. |
| 8,920,377 B2 | 12/2014 | Edwards et al. |
| 8,925,756 B2 | 1/2015 | Tarapata et al. |
| 8,926,594 B2 | 1/2015 | Edwards et al. |
| 8,932,252 B2 | 1/2015 | Edwards et al. |
| 8,939,943 B2 | 1/2015 | Edwards et al. |
| 8,992,476 B2 | 3/2015 | Shang et al. |
| 9,016,502 B2 | 4/2015 | Hollars et al. |
| 9,017,287 B2 | 4/2015 | Bicknell et al. |
| 9,022,022 B2 | 5/2015 | Edwards et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,101,744 B2 | 8/2015 | Ducharme |
| 9,119,920 B2 | 9/2015 | Cowe |
| 9,149,579 B2 | 10/2015 | Edwards et al. |
| 9,149,582 B2 | 10/2015 | Sugimoto et al. |
| D744,005 S | 11/2015 | Anderson et al. |
| 9,173,999 B2 | 11/2015 | Edwards et al. |
| 9,180,244 B2 | 11/2015 | Anderson et al. |
| 9,199,038 B2 | 12/2015 | Daniel |
| 9,216,251 B2 | 12/2015 | Daniel |
| 9,220,841 B2 | 12/2015 | Daniel |
| 9,238,108 B2 | 1/2016 | Edwards et al. |
| 9,259,539 B2 | 2/2016 | Edwards et al. |
| 9,265,887 B2 | 2/2016 | Julian et al. |
| 9,278,048 B2 | 3/2016 | Freed |
| 9,278,177 B2 | 3/2016 | Edwards et al. |
| 9,278,182 B2 | 3/2016 | Edwards et al. |
| 9,302,047 B2 | 4/2016 | Alexandersson |
| 9,327,077 B2 | 5/2016 | Edwards et al. |
| 9,333,305 B2 | 5/2016 | McLoughlin et al. |
| 9,333,308 B2 | 5/2016 | Mide et al. |
| 9,339,610 B2 | 5/2016 | Julian et al. |
| 9,352,091 B2 | 5/2016 | Edwards et al. |
| 9,375,533 B2 | 6/2016 | Ducharme et al. |
| 9,408,973 B2 | 8/2016 | Shang et al. |
| 9,441,790 B2 | 9/2016 | Tarapata et al. |
| 9,443,445 B2 | 9/2016 | Laurusonis et al. |
| 9,474,869 B2 | 10/2016 | Edwards et al. |
| 9,486,584 B2 | 11/2016 | Julian et al. |
| 9,498,574 B2 | 11/2016 | Davis et al. |
| 9,517,307 B2 | 12/2016 | Blondino et al. |
| 9,518,703 B2 | 12/2016 | Quail |
| 9,522,235 B2 | 12/2016 | Edwards et al. |
| 9,542,826 B2 | 1/2017 | Edwards et al. |
| 9,550,025 B2 | 1/2017 | Dunne |
| 9,555,191 B2 | 1/2017 | Edwards et al. |
| 9,561,328 B2 | 2/2017 | Shang et al. |
| 9,572,938 B2 | 2/2017 | Julian et al. |
| 9,623,182 B2 | 4/2017 | Alexandersson |
| 9,623,183 B2 | 4/2017 | Jennings et al. |
| 9,636,460 B1 | 5/2017 | Jaeger et al. |
| 9,662,452 B2 | 5/2017 | Daniel |
| 9,675,754 B2 | 6/2017 | DeSalvo et al. |
| 9,713,677 B2 | 7/2017 | Daniel |
| 9,724,471 B2 | 8/2017 | Edwards et al. |
| 9,731,080 B2 | 8/2017 | Douglas Ivan |
| 9,737,669 B2 | 8/2017 | Edwards et al. |
| 9,757,519 B2 | 9/2017 | Alexandersson |
| 9,764,089 B2 | 9/2017 | Alexandersson |
| 9,764,090 B2 | 9/2017 | Bicknell et al. |
| 9,789,266 B2 | 10/2017 | Mide et al. |

(56) References Cited

U.S. PATENT DOCUMENTS

| | | |
|---|---|---|
| 9,805,620 B2 | 10/2017 | Edwards et al. |
| 9,810,375 B2 | 11/2017 | Rider et al. |
| 9,814,838 B2 | 11/2017 | Edwards et al. |
| 9,821,117 B2 | 11/2017 | Anderson et al. |
| 9,833,573 B2 | 12/2017 | Edwards et al. |
| 9,836,948 B2 | 12/2017 | Edwards et al. |
| 9,867,931 B2 | 1/2018 | Gittard |
| 9,867,938 B2 | 1/2018 | Edwards et al. |
| 9,867,942 B2 | 1/2018 | Alexandersson |
| 9,867,949 B2 | 1/2018 | Sund et al. |
| 9,878,102 B2 | 1/2018 | Julian et al. |
| 9,895,493 B2 | 2/2018 | Burnell et al. |
| 9,911,308 B2 | 3/2018 | Edwards et al. |
| 9,943,649 B2 | 4/2018 | Shang et al. |
| 9,956,345 B2 | 5/2018 | Anderson et al. |
| 9,956,353 B2 | 5/2018 | Rao et al. |
| 9,962,490 B2 | 5/2018 | Karlsson et al. |
| 9,962,494 B2 | 5/2018 | Blancke et al. |
| 10,039,879 B2 | 8/2018 | Davis et al. |
| 10,071,203 B2 | 9/2018 | Edwards et al. |
| 10,076,611 B2 | 9/2018 | Edwards et al. |
| 10,092,704 B2 | 10/2018 | Daniel |
| 10,099,023 B2 | 10/2018 | Edwards et al. |
| 10,105,489 B2 | 10/2018 | Edwards et al. |
| 10,124,121 B2 | 11/2018 | Bode |
| 10,130,774 B2 | 11/2018 | Daniel |
| 10,130,800 B2 | 11/2018 | Kiss |
| 10,155,086 B2 | 12/2018 | Sugimoto et al. |
| 10,159,800 B2 | 12/2018 | Säll |
| 10,179,222 B2 | 1/2019 | Fine et al. |
| 10,183,116 B2 | 1/2019 | Edwards et al. |
| 10,192,464 B2 | 1/2019 | Edwards et al. |
| 10,238,806 B2 | 3/2019 | Edwards et al. |
| 10,300,208 B2 | 5/2019 | Gylleby et al. |
| 10,300,209 B2 | 5/2019 | Stewart |
| 10,307,539 B2 | 6/2019 | Alexandersson |
| 10,314,977 B2 | 6/2019 | Edwards et al. |
| 10,328,205 B2 | 6/2019 | Stefanov |
| 10,335,549 B2 | 7/2019 | Edwards et al. |
| 10,342,924 B2 | 7/2019 | Edwards et al. |
| 10,350,356 B2 | 7/2019 | Hirschel et al. |
| 10,384,009 B2 | 8/2019 | Olson et al. |
| 10,420,898 B2 | 9/2019 | Daniel |
| 10,471,217 B2 | 11/2019 | Plumptre et al. |
| 10,561,798 B2 | 2/2020 | Holland et al. |
| 10,569,019 B2 | 2/2020 | Hirschel et al. |
| 10,576,206 B2 | 3/2020 | Edwards et al. |
| 10,610,351 B2 | 4/2020 | McCawley et al. |
| 10,617,824 B2 | 4/2020 | Alexandersson |
| 10,646,659 B2 | 5/2020 | Huthmacher et al. |
| 10,661,014 B2 | 5/2020 | Sarkinen et al. |
| 10,688,244 B2 | 6/2020 | Edwards et al. |
| 10,695,495 B2 | 6/2020 | Blondino et al. |
| 10,709,844 B2 | 7/2020 | Sund et al. |
| 10,716,901 B2 | 7/2020 | Genosar |
| 10,737,028 B2 | 8/2020 | Edwards et al. |
| 10,751,483 B2 | 8/2020 | Hatch et al. |
| 10,792,428 B2 | 10/2020 | Anderson et al. |
| 10,796,604 B2 | 10/2020 | Edwards et al. |
| 10,835,673 B2 | 11/2020 | Edwards et al. |
| 10,842,938 B2 | 11/2020 | Edwards et al. |
| 10,881,799 B2 | 1/2021 | Hirschel et al. |
| 10,912,883 B2 | 2/2021 | McCawley et al. |
| 10,918,791 B2 | 2/2021 | Edwards et al. |
| 10,933,197 B2 | 3/2021 | Daniel |
| 10,960,155 B2 | 3/2021 | Edwards et al. |
| 11,001,435 B2 | 5/2021 | Genosar |
| 11,014,524 B2 | 5/2021 | Yi |
| 11,058,817 B2 | 7/2021 | Sugimoto et al. |
| 11,058,827 B2 | 7/2021 | Mosebach et al. |
| 11,065,386 B2 | 7/2021 | Atterbury et al. |
| 11,071,824 B2 | 7/2021 | Auld et al. |
| 11,116,910 B2 | 9/2021 | Säll et al. |
| 11,167,087 B2 | 11/2021 | Meyers et al. |
| 11,263,921 B2 | 3/2022 | Edwards et al. |
| 11,291,775 B2 | 4/2022 | Daniel |
| 11,324,895 B2 | 5/2022 | Schader et al. |
| 11,357,922 B2 | 6/2022 | Mosebach et al. |
| 11,369,745 B2 | 6/2022 | Garson et al. |
| 11,376,363 B2 | 7/2022 | Alexandersson |
| 11,400,215 B2 | 8/2022 | Cowe et al. |
| 11,400,226 B2 | 8/2022 | Yigal et al. |
| 11,426,520 B2 | 8/2022 | Edwards et al. |
| 11,517,673 B2 | 12/2022 | Pedersen et al. |
| 11,517,674 B2 | 12/2022 | Edwards et al. |
| 11,517,680 B2 | 12/2022 | Teucher et al. |
| 11,529,469 B2 | 12/2022 | Lee et al. |
| RE49,369 E | 1/2023 | Stefanov |
| 11,547,801 B2 | 1/2023 | Grygus et al. |
| 11,590,286 B2 | 2/2023 | Edwards et al. |
| 11,607,494 B2 | 3/2023 | Hirschel et al. |
| 11,617,833 B2 | 4/2023 | Rioux et al. |
| 11,638,786 B2 | 5/2023 | Huthmacher et al. |
| 11,648,348 B2 | 5/2023 | Alexandersson |
| 11,654,245 B2 | 5/2023 | Plumptre et al. |
| 11,660,388 B2 | 5/2023 | Lee et al. |
| 11,684,723 B2 | 6/2023 | Sund et al. |
| 11,717,610 B2 | 8/2023 | Sarkinen et al. |
| 11,724,040 B2 | 8/2023 | Säll et al. |
| 11,738,154 B2 | 8/2023 | Huculak et al. |
| 11,752,269 B2 | 9/2023 | Salari |
| 11,752,273 B2 | 9/2023 | Huthmacher et al. |
| 11,771,830 B2 | 10/2023 | Edwards et al. |
| 11,771,839 B2 | 10/2023 | Daniel |
| 11,819,669 B2 | 11/2023 | Daniel |
| 11,819,671 B2 | 11/2023 | Daniel |
| 11,826,551 B2 | 11/2023 | Atterbury et al. |
| 11,826,554 B2 | 11/2023 | Daniel |
| 11,844,933 B2 | 12/2023 | Genosar |
| 11,890,453 B2 | 2/2024 | Auld et al. |
| 11,944,789 B2 | 4/2024 | Hirschel et al. |
| 11,969,581 B2 | 4/2024 | Pedersen et al. |
| 11,975,464 B2 | 5/2024 | Mangiagalli |
| 11,980,749 B2 | 5/2024 | Marsh et al. |
| 11,992,652 B2 | 5/2024 | Auld et al. |
| 12,005,236 B2 | 6/2024 | Blondino et al. |
| 12,017,047 B2 | 6/2024 | Meyers et al. |
| 2003/0105430 A1 | 6/2003 | Lavi et al. |
| 2003/0233070 A1 | 12/2003 | De La Serna et al. |
| 2005/0197650 A1 | 9/2005 | Sugimoto et al. |
| 2007/0149925 A1 | 6/2007 | Edwards et al. |
| 2007/0233001 A1 | 10/2007 | Burroughs et al. |
| 2008/0262438 A1 | 10/2008 | Bollenbach et al. |
| 2010/0121275 A1 | 5/2010 | Edwards et al. |
| 2010/0185177 A1 | 7/2010 | Gillum |
| 2011/0125100 A1 | 5/2011 | Schwirtz et al. |
| 2011/0238037 A1 | 9/2011 | Hwang et al. |
| 2014/0052071 A1 | 2/2014 | Pickhard et al. |
| 2014/0094769 A1 | 4/2014 | Hwang et al. |
| 2014/0188048 A1 | 7/2014 | Edwards et al. |
| 2014/0296824 A1 | 10/2014 | Edwards et al. |
| 2014/0319140 A1 | 10/2014 | Holbeche |
| 2015/0320940 A1 | 11/2015 | Mide et al. |
| 2016/0008541 A1 | 1/2016 | Hirschel et al. |
| 2016/0082189 A1 | 3/2016 | Anderson et al. |
| 2016/0184535 A1 | 6/2016 | Edwards et al. |
| 2016/0235916 A1 | 8/2016 | Edwards et al. |
| 2016/0262980 A1 | 9/2016 | Mide et al. |
| 2016/0296716 A1 | 10/2016 | Cabiri et al. |
| 2016/0361496 A1 | 12/2016 | Guillermo et al. |
| 2017/0209647 A1 | 7/2017 | Daniel |
| 2017/0246392 A1 | 8/2017 | DeSalvo et al. |
| 2017/0246395 A1 | 8/2017 | Daniel et al. |
| 2017/0354788 A1 | 12/2017 | Quinn et al. |
| 2018/0106431 A1 | 4/2018 | Timm et al. |
| 2018/0283608 A1 | 10/2018 | Wilder et al. |
| 2018/0361069 A1 | 12/2018 | Schader et al. |
| 2018/0369506 A1 | 12/2018 | Edwards et al. |
| 2018/0370480 A1 | 12/2018 | Yi |
| 2019/0030247 A1 | 1/2019 | Edwards et al. |
| 2019/0070362 A1 | 3/2019 | Lynch |
| 2019/0117897 A1 | 4/2019 | Avery et al. |
| 2019/0186693 A1 | 6/2019 | Wilder et al. |
| 2019/0217004 A1 | 7/2019 | Edwards et al. |

(56) References Cited

U.S. PATENT DOCUMENTS

| | | |
|---|---|---|
| 2019/0217043 A1 | 7/2019 | Fine et al. |
| 2019/0282763 A1 | 9/2019 | Edwards et al. |
| 2019/0381245 A1 | 12/2019 | Edwards et al. |
| 2020/0086051 A1* | 3/2020 | Grygus .............. A61M 5/2033 |
| 2020/0164155 A1 | 5/2020 | Mojarrad et al. |
| 2020/0232605 A1 | 7/2020 | McCawley et al. |
| 2020/0316291 A1* | 10/2020 | Gibson ............ A61M 5/14248 |
| 2020/0345937 A1 | 11/2020 | Genosar |
| 2020/0353180 A1 | 11/2020 | Edwards et al. |
| 2021/0085881 A1 | 3/2021 | Daniel |
| 2021/0093789 A1 | 4/2021 | Plambech et al. |
| 2021/0093796 A1 | 4/2021 | Finkelstein et al. |
| 2021/0093797 A1 | 4/2021 | Finkelstein et al. |
| 2021/0138152 A1 | 5/2021 | Edwards et al. |
| 2021/0196892 A1* | 7/2021 | Dasbach ................ A61M 5/50 |
| 2021/0244894 A1 | 8/2021 | Edwards et al. |
| 2021/0322683 A1 | 10/2021 | Mosebach et al. |
| 2021/0338936 A1 | 11/2021 | Pedersen et al. |
| 2021/0353861 A1 | 11/2021 | Rose et al. |
| 2021/0353862 A1 | 11/2021 | Schrul et al. |
| 2021/0379347 A1 | 12/2021 | Kiss |
| 2021/0402097 A1 | 12/2021 | Genosar et al. |
| 2022/0008655 A1 | 1/2022 | Ratjen |
| 2022/0040413 A1 | 2/2022 | Edwards et al. |
| 2022/0054753 A1 | 2/2022 | Meyers et al. |
| 2022/0118177 A1 | 4/2022 | Burgess et al. |
| 2022/0176041 A2 | 6/2022 | Rioux et al. |
| 2022/0193343 A1 | 6/2022 | Burgess et al. |
| 2022/0233778 A1 | 7/2022 | Schader et al. |
| 2022/0257865 A1 | 8/2022 | Mosebach et al. |
| 2022/0336076 A1 | 10/2022 | Albertini et al. |
| 2022/0355034 A1 | 11/2022 | Edwards et al. |
| 2022/0362470 A1 | 11/2022 | Alexandersson |
| 2023/0008831 A1 | 1/2023 | Huang et al. |
| 2023/0016657 A1 | 1/2023 | Pedersen et al. |
| 2023/0067401 A1 | 3/2023 | Teucher et al. |
| 2023/0076855 A1 | 3/2023 | Edwards et al. |
| 2023/0082790 A1 | 3/2023 | Lee et al. |
| 2023/0090397 A1 | 3/2023 | Olson et al. |
| 2023/0105585 A1 | 4/2023 | Grygus et al. |
| 2023/0119081 A1 | 4/2023 | McCawley et al. |
| 2023/0137976 A1 | 5/2023 | Corrigan et al. |
| 2023/0158247 A1 | 5/2023 | Huthmacher et al. |
| 2023/0173184 A1 | 6/2023 | McCawley et al. |
| 2023/0248919 A1 | 8/2023 | Plumptre et al. |
| 2023/0270950 A1 | 8/2023 | Sund et al. |
| 2023/0277770 A1 | 9/2023 | Hirschel et al. |
| 2023/0347067 A1 | 11/2023 | Xie |
| 2023/0355876 A1 | 11/2023 | Calderwood et al. |
| 2023/0355881 A1 | 11/2023 | Genosar |
| 2023/0355887 A1 | 11/2023 | Daniel |
| 2023/0355892 A1 | 11/2023 | Calderwood et al. |
| 2023/0364353 A1 | 11/2023 | Atterbury et al. |
| 2023/0372620 A1 | 11/2023 | Sarkinen et al. |
| 2023/0381424 A1 | 11/2023 | Bech et al. |
| 2023/0398299 A1 | 12/2023 | Atterbury et al. |
| 2023/0405235 A1 | 12/2023 | Daniel |
| 2024/0033434 A1 | 2/2024 | Dunne, Jr. et al. |
| 2024/0075204 A1 | 3/2024 | Halbig et al. |
| 2024/0091462 A1 | 3/2024 | Yin |
| 2024/0165336 A1 | 5/2024 | Pedersen et al. |
| 2024/0173483 A1 | 5/2024 | Meyers et al. |
| 2024/0198000 A1 | 6/2024 | Hirschel et al. |
| 2024/0216611 A1 | 7/2024 | Meyers et al. |
| 2024/0246268 A1 | 7/2024 | Mangiagalli |
| 2024/0252761 A1 | 8/2024 | Dasbach et al. |
| 2024/0252765 A1 | 8/2024 | Calderwood et al. |
| 2024/0252766 A1 | 8/2024 | Calderwood et al. |
| 2024/0261508 A1 | 8/2024 | Auld et al. |

FOREIGN PATENT DOCUMENTS

| | | |
|---|---|---|
| CA | 2831102 A1 | 8/2012 |
| CA | 3017183 A1 | 9/2017 |
| CN | 108495666 A | 9/2018 |
| CN | 109071071 B | 3/2021 |
| EP | 0258057 A2 | 3/1988 |
| EP | 1416218 A2 | 5/2004 |
| EP | 3037712 A1 | 6/2016 |
| EP | 3260147 A1 | 12/2017 |
| EP | 3354303 A1 | 8/2018 |
| EP | 3426567 A2 | 1/2019 |
| HK | 40001863 A | 3/2020 |
| IL | 261703 | 10/2018 |
| IN | 201817036580 | 1/2019 |
| JP | 2016533213 A | 10/2016 |
| JP | 6923947 B2 | 8/2021 |
| KR | 20190008523 A | 1/2019 |
| MX | 2018010887 A | 5/2019 |
| RU | 2505322 C2 | 1/2014 |
| RU | 2748403 C2 | 5/2021 |
| SG | 11201807761 | 10/2018 |
| TW | 201818983 A | 6/2018 |
| WO | 95/03078 A1 | 2/1995 |
| WO | 9915214 | 4/1999 |
| WO | 03047663 | 6/2003 |
| WO | 2004067067 | 8/2004 |
| WO | 2005115508 | 12/2005 |
| WO | 2006057636 | 6/2006 |
| WO | 2008064092 | 5/2008 |
| WO | 2008146021 | 12/2008 |
| WO | 2010097593 A1 | 9/2010 |
| WO | 2011043714 | 4/2011 |
| WO | 2011116304 | 9/2011 |
| WO | 2011123024 | 10/2011 |
| WO | 2013164358 | 11/2013 |
| WO | 2014109012 | 7/2014 |
| WO | 2014139914 | 9/2014 |
| WO | 2014146209 | 9/2014 |
| WO | 2014146210 | 9/2014 |
| WO | 2015044055 | 4/2015 |
| WO | 2015113968 | 8/2015 |
| WO | 2015117864 | 8/2015 |
| WO | 2015121081 | 8/2015 |
| WO | 2015074977 | 9/2015 |
| WO | 2015185311 | 12/2015 |
| WO | 2016027096 | 2/2016 |
| WO | 2016034407 | 3/2016 |
| WO | 2016/130679 A2 | 8/2016 |
| WO | 2016170346 | 10/2016 |
| WO | 2016170347 | 10/2016 |
| WO | 2016193346 | 12/2016 |
| WO | 2016193352 | 12/2016 |
| WO | 2016205403 | 12/2016 |
| WO | 2017/004345 A1 | 1/2017 |
| WO | 2017114910 | 7/2017 |
| WO | 2017/129191 A1 | 8/2017 |
| WO | 2017143461 | 8/2017 |
| WO | 2017148618 | 9/2017 |
| WO | 2017156186 A2 | 9/2017 |
| WO | 2017/177094 A2 | 10/2017 |
| WO | 2017181297 | 10/2017 |
| WO | 2017/196504 A1 | 11/2017 |
| WO | 2018007251 | 1/2018 |
| WO | 2018013493 | 1/2018 |
| WO | 2018015749 | 1/2018 |
| WO | 2018080959 | 5/2018 |
| WO | 2018082887 | 5/2018 |
| WO | 2018100117 | 6/2018 |
| WO | 2018119218 | 6/2018 |
| WO | 2018166951 | 9/2018 |
| WO | 2018204779 A1 | 11/2018 |
| WO | 2019090193 | 5/2019 |
| WO | 2019090195 | 5/2019 |
| WO | 2019121358 | 6/2019 |
| WO | 2019137701 | 7/2019 |
| WO | 2019/197361 A1 | 10/2019 |
| WO | 2020072846 | 4/2020 |
| WO | 2020126270 | 6/2020 |
| WO | 2020140040 | 7/2020 |
| WO | 2020164910 | 8/2020 |
| WO | 2020210513 | 10/2020 |
| WO | 2021003409 | 1/2021 |
| WO | 2021004018 A1 | 1/2021 |

(56) References Cited

FOREIGN PATENT DOCUMENTS

| | | |
|---|---|---|
| WO | 2021051010 | 3/2021 |
| WO | 2021099542 A1 | 5/2021 |
| WO | 2021169048 | 9/2021 |
| WO | 2022055759 | 3/2022 |
| WO | 2022055760 | 3/2022 |
| WO | 2022078986 | 4/2022 |
| WO | 2022078987 | 4/2022 |
| WO | 2022128533 | 6/2022 |
| WO | 2022147166 | 7/2022 |
| WO | 2022240749 | 11/2022 |
| WO | 2022253852 | 12/2022 |
| WO | 2022256807 | 12/2022 |
| WO | 2023272716 | 1/2023 |
| WO | 2023016888 | 2/2023 |
| WO | 2023064497 | 4/2023 |
| WO | 2023066677 | 4/2023 |
| WO | 2023073056 | 5/2023 |
| WO | 2023073058 | 5/2023 |
| WO | 2023079357 | 5/2023 |
| WO | 2023083616 | 5/2023 |
| WO | 2023107515 | 6/2023 |
| WO | 2023138800 | 7/2023 |
| WO | 2023141627 | 7/2023 |
| WO | 2023173142 | 9/2023 |
| WO | 2024030451 | 2/2024 |
| WO | 2024069381 | 4/2024 |
| WO | 2024094706 | 5/2024 |
| WO | 2024118184 | 6/2024 |
| WO | 2024153405 | 7/2024 |
| ZA | 201806403 B | 6/2019 |

OTHER PUBLICATIONS

International Written Opinion and Search Report issued in International Patent Application No. PCT/US2021/065567 dated Apr. 25, 2022 (17 pages, in English).

English Translation of TIPO Search Report for Taiwan Patent Application No. 109122426, dated Jan. 28, 2024 (1 page).

\* cited by examiner

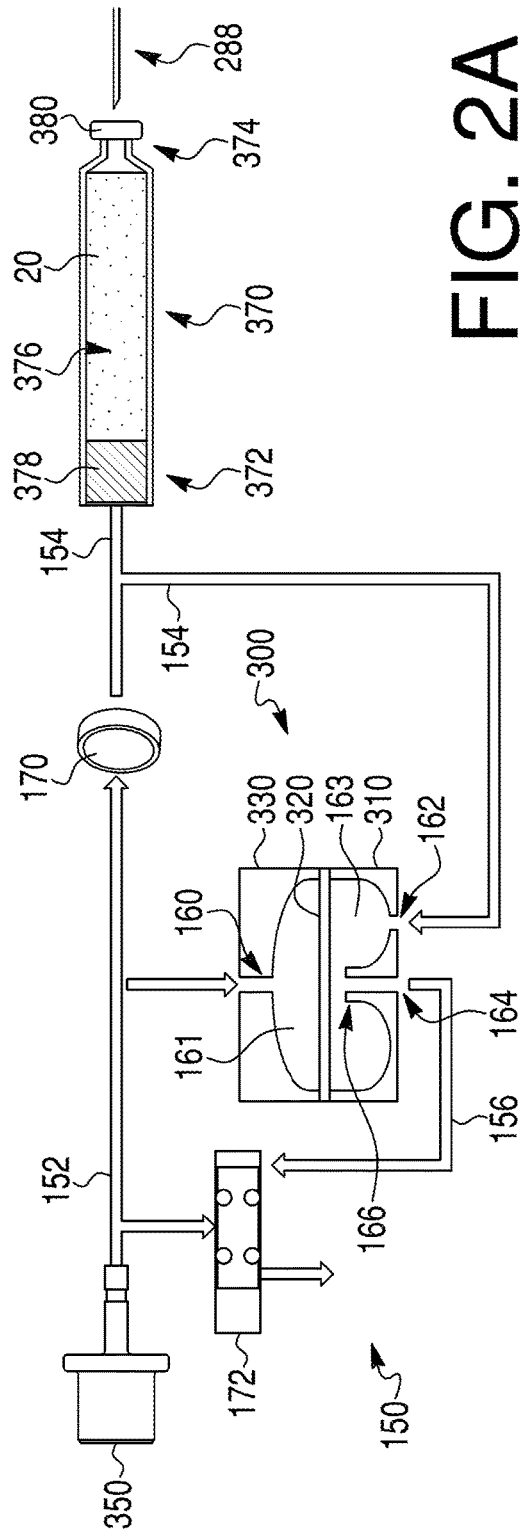
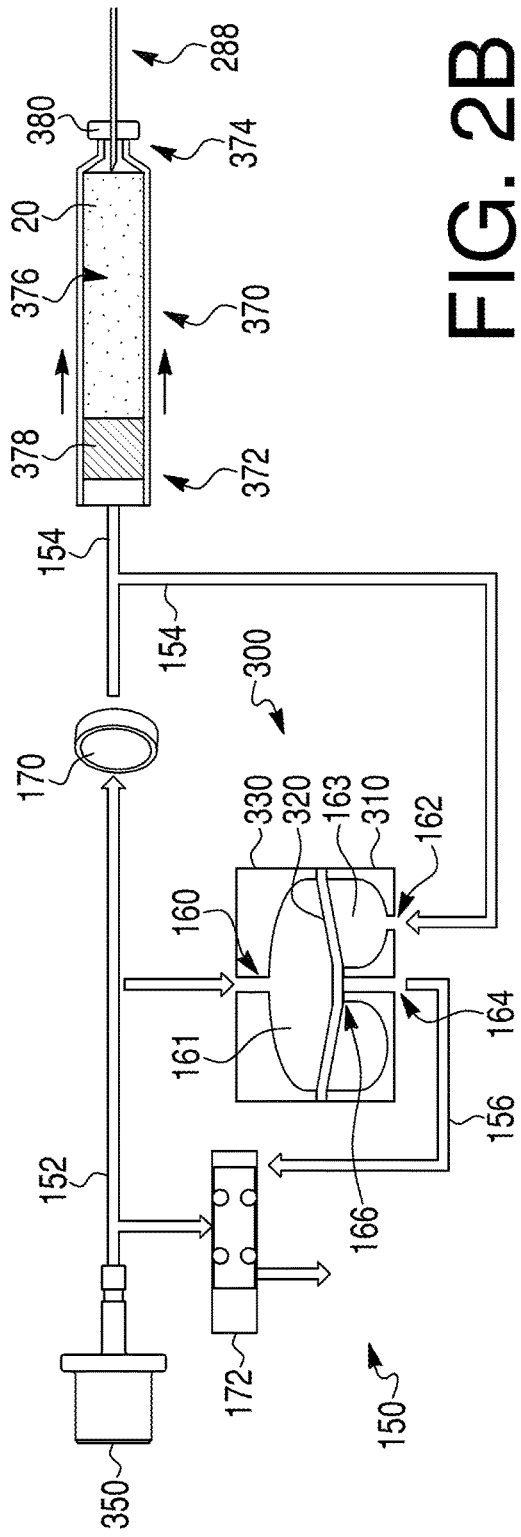

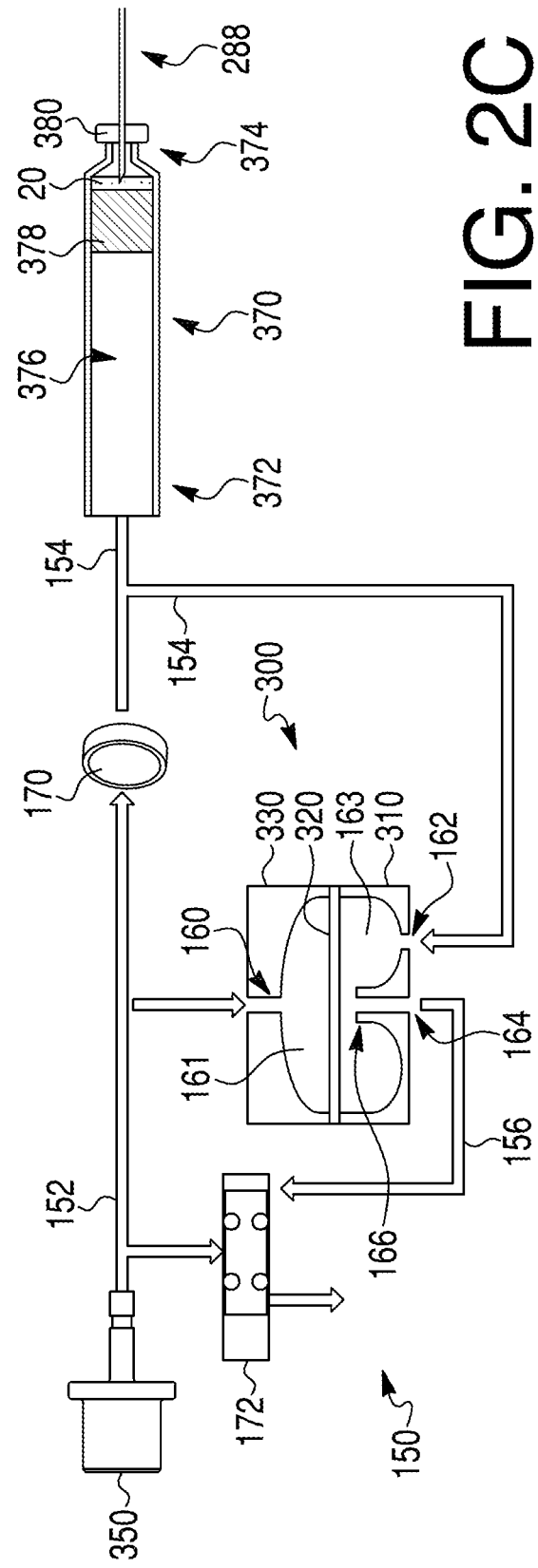

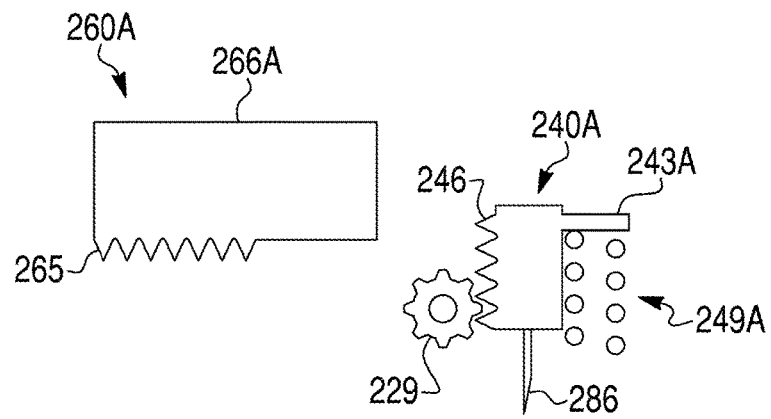
FIG. 41A
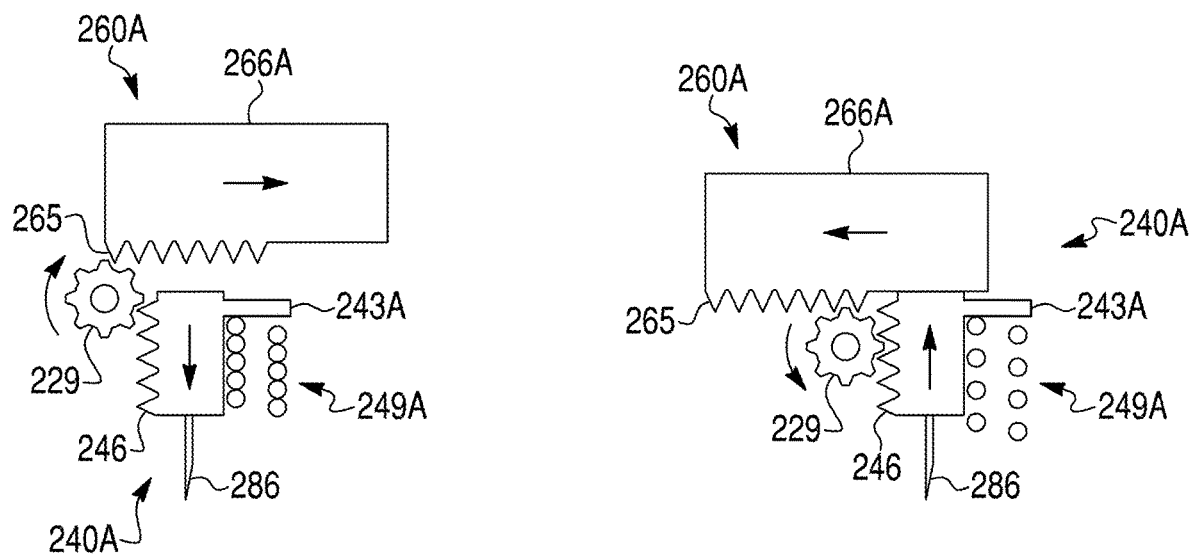
FIG. 41B
FIG. 41C

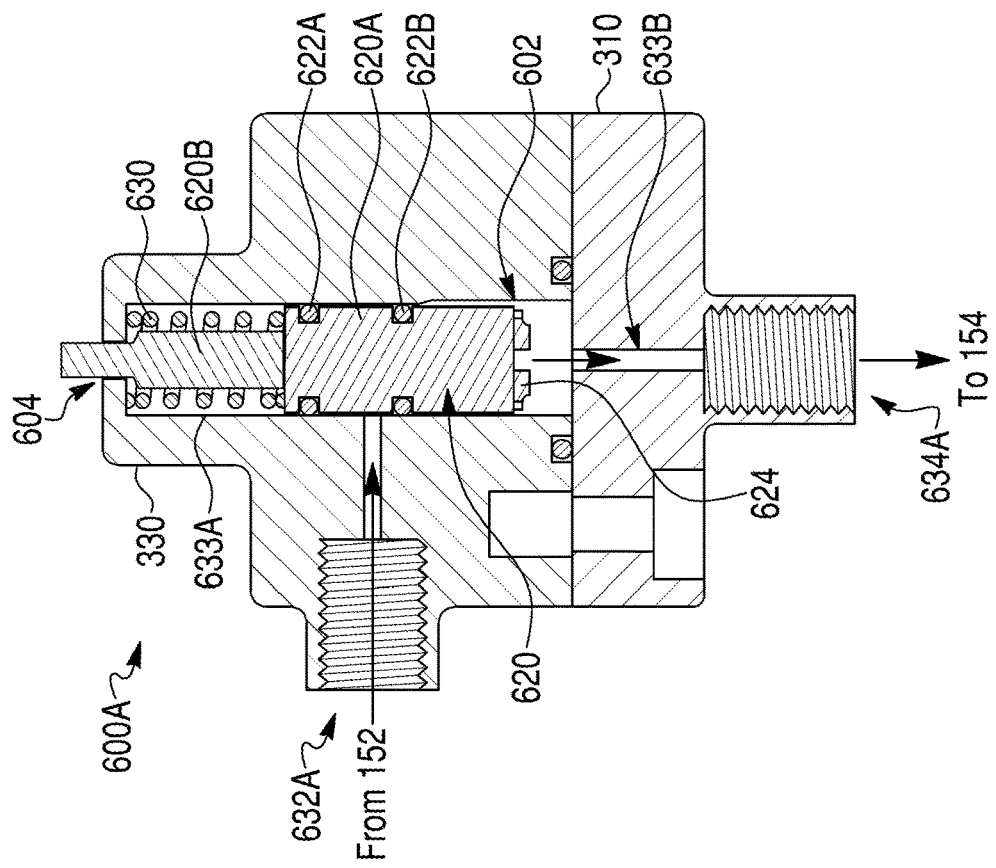
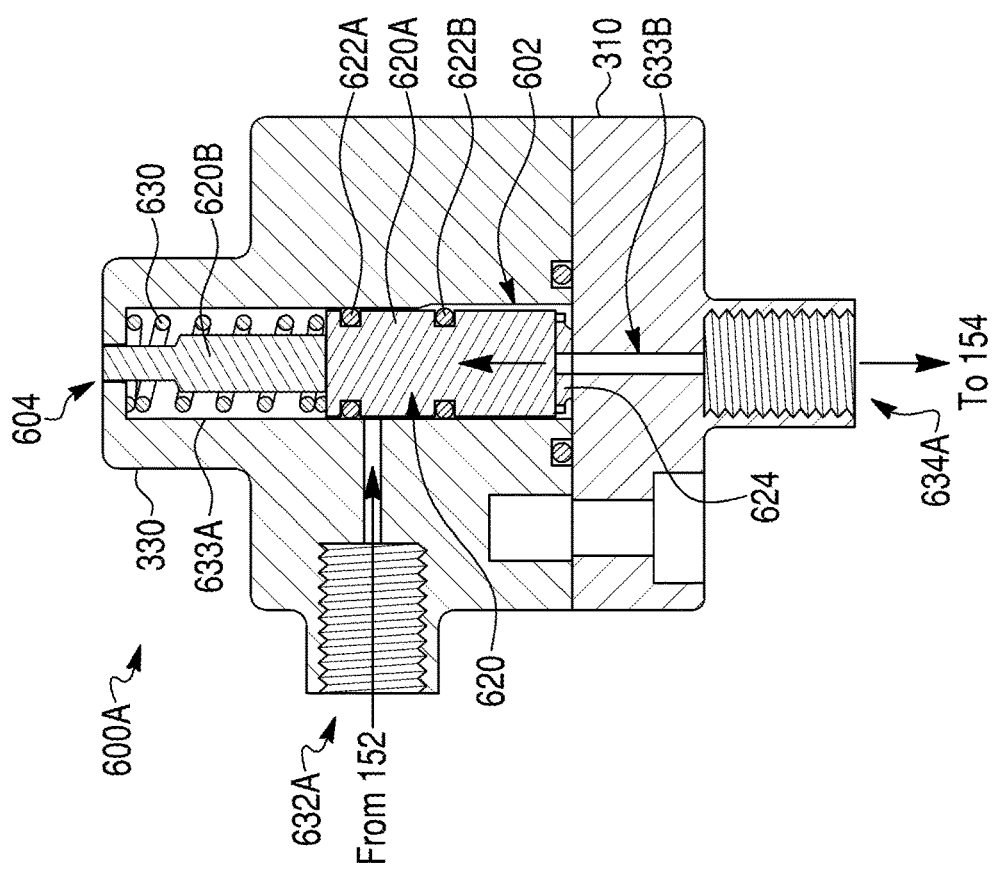

AUTO-INJECTOR AND RELATED METHODS OF USE

CROSS-REFERENCE TO RELATED APPLICATIONS

This application claims priority to U.S. Application No. 63/133,185, filed Dec. 31, 2020, and U.S. Application No. 63/134,554, filed Jan. 6, 2021, both of which are incorporated by reference herein in their entireties.

FIELD OF DISCLOSURE

Aspects of the present disclosure relate to devices and methods for delivering a fluid from a needle into a user using mechanisms, e.g., a pressurized medium and/or spring, which automatically control injection of the needle and fluid. More specifically, embodiments of the present disclosure relate to auto-injectors and methods for delivering a dose of a medicament to a user by automatically deploying and retracting an injection needle.

INTRODUCTION

In various available auto-injectors, upon activation by a user, a needle is deployed, and fluid is delivered from the needle into the user. After completion of fluid delivery, the needle may be retracted for user comfort, needle safety, and positive perception of the product. However, many auto-injectors require separate user actions for inserting and removing the needle. In addition, many available auto-injectors have a high profile. For example, existing pen-type injectors that align a medicament container along the axis of injection show a high profile relative to the skin of the patient. Patients may respond to such auto-injectors with anxiety, especially because the high profile is often perceived by patients to correspond to a long needle length, whereas the actual needle length may be relatively short. Additionally, many auto-injectors must be secured to the user for extended periods of time, which may be an inconvenience for the user.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIGS. 2A-2C are schematic illustrations of features of an auto-injector, according to an example of the disclosure.

FIGS. 41A-41C are schematic illustrations of portions of the needle mechanism of FIGS. 33-34, according to an example of the disclosure.

FIGS. 61A-61B are schematic illustrations of additional features of an auto-injector, according to an example of the disclosure.

Figure 1:
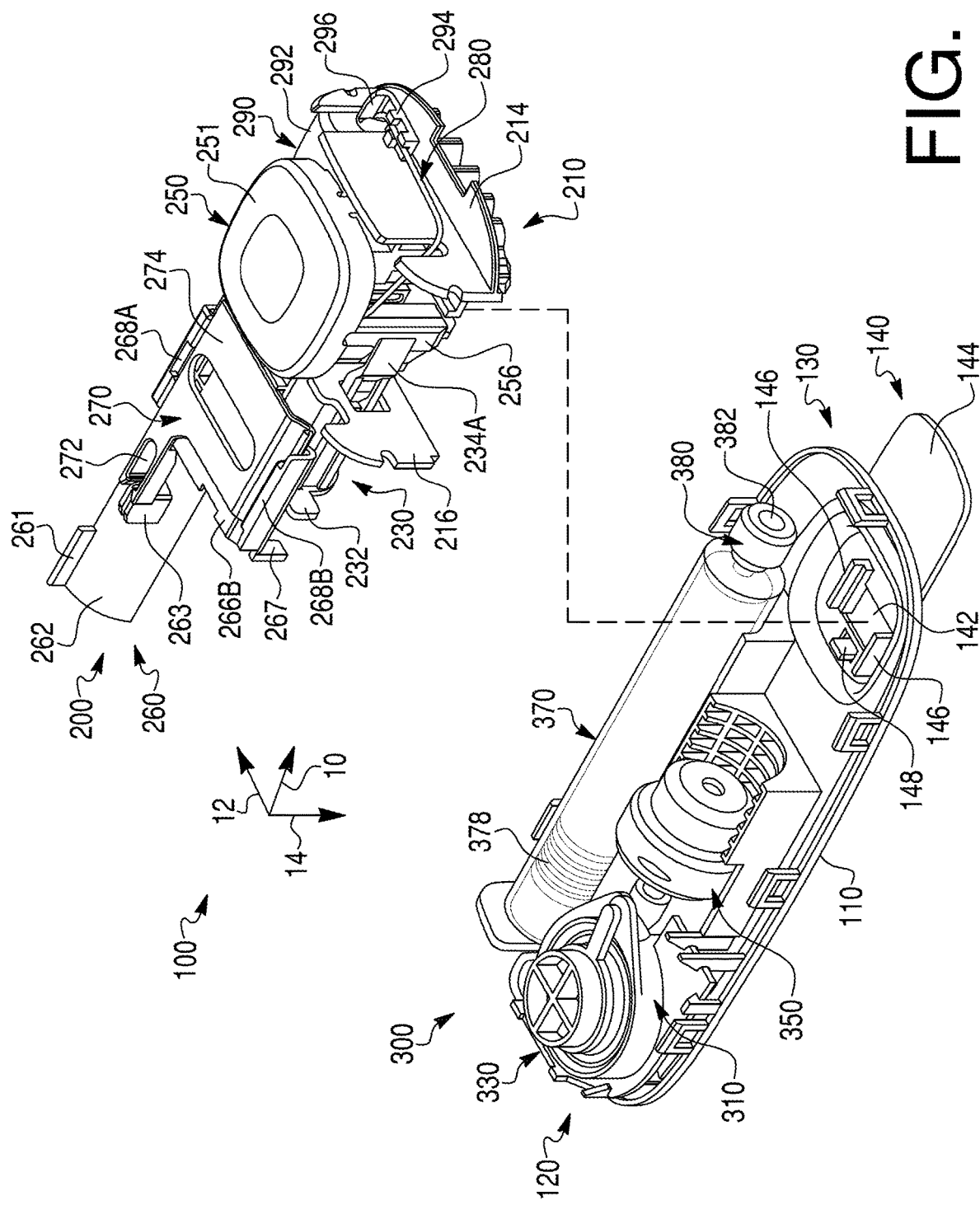
FIG. 1 is a perspective view of an auto-injector, according to an example of the disclosure.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

Notably, for simplicity and clarity of illustration, certain aspects of the figures depict the general structure and/or manner of construction of the various embodiments. Descriptions and details of well-known features and techniques may be omitted to avoid unnecessarily obscuring other features. Elements in the figures are not necessarily drawn to scale; the dimensions of some features may be exaggerated relative to other elements to improve understanding of the example embodiments. For example, one of ordinary skill in the art appreciates that the cross-sectional views are not drawn to scale and should not be viewed as representing proportional relationships between different components. The cross-sectional views are provided to help illustrate the various components of the depicted assembly, and to show their relative positioning to one another.

DETAILED DESCRIPTION

Reference will now be made in detail to examples of the present disclosure, which are illustrated in the accompanying drawings. Wherever possible, the same reference numbers will be used throughout the drawings to refer to the same or like parts. Embodiments of the present disclosure may be used with any type of fluid-containing products, such as liquid drug substances, liquid placebos, or other liquids that may be dispensed in a dose form. In the discussion that follows, terms "about," "approximately," "substantially," and the like, when used in describing a numerical value, denote a variation of +/−10% of that value, unless specified otherwise.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal."

As used herein, the terms "distal" and "distally" refer to a location (or portion of a device) relatively closer to, or in the direction of, a patient delivery site, and the terms "proximal" and "proximally" refer to a location (or portion of a device) relatively closer to, or in the direction of, a user end opposite a distal location/portion of a device. In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items.

As described above, existing auto-injectors often require multiple user interactions to self-administer a drug, including, e.g., separate user interactions for deploying a needle and subsequently retracting the needle after drug delivery. These additional steps can increase complexity of self-administration of drugs, introduce user errors, and cause user discomfort. Accordingly, the present disclosure is directed to various embodiments of an injection device (e.g., auto-injector) that simplifies self-administration of drugs, or other therapeutic agents, by a user. Specifically, according to certain embodiments, the auto-injector may not require any additional user interaction to withdraw a needle once the needle is subcutaneously inserted into the user. Thus, auto-injectors of the present disclosure are simplified to help prevent misuse or user error.

As described above, existing auto-injectors often require multiple components and user operations to administer a drug, including, various spring or motor mechanisms. These additional components can increase complexity of manufacture and introduce mechanical faults or user error. Accordingly, the present disclosure is directed to various embodiments of an injection device (e.g., auto-injector) that simplifies and refines administration of drugs, or other therapeutic agents.

Referring now to FIG. 1, an exemplary auto-injector 100 is depicted in accordance with an example of the present disclosure. Auto-injector 100 may include a housing having a bottom cover 110 and a top cover (not shown). Bottom cover 110 may be defined by a first end 120 and a second end 130. Bottom cover 110 may define a tissue-engaging surface along an exterior interface of bottom cover 110, through which a needle may be deployed and retracted (see FIG. 33). The top cover may define a user interface surface from which a user may control auto-injector 100, such as through a window providing visualization of one or more internal components of auto-injector 100.

Auto-injector 100 may include a needle mechanism 200 and a valve assembly 300 housed between the bottom cover 110 and the top cover of the housing. Needle mechanism 200 may include a carrier 210, a can actuator 230 (sometimes referred to herein as "actuator"), a button 250, a shuttle actuator 260, an indicator slide 270, a fluid conduit 280, and a needle retainer or sterile connector 290. Valve assembly 300 may include a low pressure body portion 310, a high pressure body portion 330, and a fluid source 350. Valve assembly 300 may be operatively coupled to fluid conduit 280 via a container 370 having a stopper 380. Stated differently, fluid conduit 280 may be in fluid communication with container 370, and container 370 may be operatively coupled to valve assembly 300. Container 370 includes a piston 378 that inhibits receipt of fluid from valve assembly 300 into container 370 and/or fluid conduit 280. As described in detail herein, needle mechanism 200 and valve assembly 300 may be coupled to one another, and collectively configured to deploy a needle (FIG. 33) through bottom cover 110, deliver a dosage of a medicament from container 370 (FIGS. 2A-2C), and retract the needle back into the housing of auto-injector 100 in response to a single actuation of auto-injector 100 by a user.

Auto-injector 100 may have any suitable dimensions to enable portability and self-attachment by a user. Auto-injector 100, for example, may have a length from about 0.5 inches to about 5.0 inches, a width of about 0.5 inches to about 3.0 inches, and a height from 0.5 inches to about 2.0 inches. Auto-injector 100 also may include a grip or frictional coating such that the outer surface of auto-injector 100 is a non-slip surface. Auto-injector 100 may be oriented about a longitudinal axis 10 (e.g., an X axis), a lateral axis 12 (e.g., a Y axis) that is substantially perpendicular to longitudinal axis 10, and a transverse axis 14 (e.g., a Z axis) that is substantially perpendicular to both longitudinal axis 10 and lateral axis 12. Transverse auto-injectors of the present disclosure, in some embodiments, may have a longer dimension along longitudinal axis 10 than along lateral axis 12 and/or transverse axis 14.

In certain embodiments of auto-injector 100, such as when auto-injector 100 is a wearable auto-injector, auto-injector 100 may include an adhesive patch positioned along an exterior of bottom cover 110. The adhesive patch may be coupled to the exterior of bottom cover 110 (e.g., the tissue-engaging surface) to help secure auto-injector 100 to a user's body (e.g., skin). The adhesive patch may be formed from fabric or any other suitable material, and may include an adhesive. The adhesive may be an aqueous or solvent-based adhesive, or may be a hot melt adhesive, for example. Suitable adhesives also include acrylic based, dextrin based, and urethane based adhesives as well as natural and synthetic elastomers. In some examples, the adhesive provided on the patch may be activated upon contact with a user's skin. In yet another example, the adhesive patch may include a non-woven polyester substrate and an acrylic or silicone adhesive. The adhesive patch may be joined to bottom cover 110 by, e.g., a double-sided adhesive, or by other mechanisms like ultrasonic welding. The adhesive patch may have a longitudinal dimension (e.g., a dimension parallel to longitudinal axis 10) that is greater than a width (e.g., a dimension parallel to lateral axis 12) of auto-injector 100.

In other embodiments of the disclosure, auto-injector 100 does not include an adhesive patch. For example, auto-injector 100 may be a handheld auto-injector, as opposed to a wearable auto-injector. In at least some embodiments, a handheld auto-injector may require a user to hold the auto-injector against the user's skin for the entirety of an injection procedure, whereas, a wearable injector may include features for securing the wearable auto-injector to the skin. For example, a wearable auto-injector may include one or more features, such as, e.g., an adhesive patch, straps, or the like, for securing to the user. In some embodiments, a handheld auto-injector according to this disclosure may be configured to deliver a medicament volume of less than 3.5 mL (or a medicament volume from about 0.5 mL to about 4.0 mL, about 1.0 mL to about 3.5 mL, about 3.0 mL, about 3.1 mL, about 3.2 mL, about 3.3 mL, about 3.4 mL, about 3.5 mL), whereas a wearable auto-injector may be configured to deliver a medicament volume of greater than 3.5 mL, greater than 4.0 mL, or greater than 5.0 mL.

Furthermore, handheld auto-injectors according to the present disclosure may be configured to complete an injection procedure, as measured from 1) a point at which that the user places the auto-injector onto the skin to 2) a point at which the user removes the auto-injector from the skin after completion of an injection, in less than about 30 seconds, less than about 25 seconds, less than about 20 seconds, less than about 15 seconds, or less than about 10 seconds. A wearable auto-injector may or will take longer than 30 seconds to complete the same steps 1) and 2) discussed above, i.e., from 1) the point in time at which the auto-injector is placed onto a user's skin, to 2) the point in time at which the auto-injector is removed from the skin.

Still referring to FIG. 1, container 370 may be sized and shaped to store a nominal value of a medicament. The "nominal volume" (also called the "specified volume," or "specified capacity") of a container refers to the container's maximum capacity, as identified by the container's manufacturer or a safety standards organization. A manufacturer or a safety standards organization may specify a container's nominal volume to indicate that the container can be filled with that volume of fluid (either aseptically or not) and be closed, stoppered, sterilized, packaged, transported, and/or used while maintaining container closure integrity, and while maintaining the safety, sterility, and/or aseptic nature of the fluid contained inside. In determining the nominal volume of a container, a manufacturer or a safety standards organization may also take into account variability that occurs during normal filling, closing, stoppering, packaging, transportation, and administration procedures. As an example, a prefillable syringe may be either hand- or machine-filled with up to its nominal volume of fluid, and may then be either vent tube- or vacuum-stoppered, without the filling and stoppering machinery and tools touching and potentially contaminating the contents of the syringe. Alternatively, the stopping machinery and tools may be sterile or aseptic, and are able to contact the contents of the syringe and/or the syringe itself without resulting in any contamination.

Container 370 may have about a 5.0 mL nominal volume in some examples, although any other suitable nominal volume (e.g., from about 0.5 mL to about 50.0 mL, or from about 2.0 mL to about 10.0 mL, or from about 3.0 mL to about 6.0 mL, or from about 1.0 mL to about 3.0 mL, or from about 2.0 mL to about 5.0 mL, or another suitable range) also may be utilized depending on the drug to be delivered. In other examples, container 370 may have a nominal volume greater than or equal to about 0.5 mL, or greater than or equal to about 2.0 mL, or greater than or equal to about 3.0 mL, or greater than or equal to about 4.0 mL, or greater than or equal to about 5.0 mL. Container 370 may contain and preserve a drug for injection into a user, and may help maintain sterility of the drug. In one embodiment, container 370 may be configured to deliver a delivered quantity of medicament (e.g., from about 0.5 mL to about 4.0 mL, about 1.0 mL to about 3.5 mL, about 3.0 mL, about 3.1 mL, about 3.2 mL, about 3.3 mL, about 3.4 mL, about 3.5 mL, greater than about 1.0 mL, greater than about 2.0 mL, greater than about 3.0 mL, greater than about 4.0 mL, greater than about 5.0 mL, greater than about 10.0 mL, greater than about 20.0 mL or another delivered quantity).

The delivered quantity may be less than the nominal volume of container 370. Furthermore, in order to deliver the delivered quantity of medicament to a user, container 370 itself may be filled with a different quantity of medicament than the delivered quantity (i.e., a filled quantity). The filled quantity may be an amount of medicament greater than the delivered quantity to account for medicament that cannot be transferred from container 370 to the user due to, e.g., dead space in container 370 or fluid conduit 280. Thus, while container 370 may have a nominal volume of 5 mL, the filled quantity and delivered quantity of medicament may be less than 5 mL.

In one embodiment, when container 370 is used in a handheld auto-injector, the delivered quantity of medicament from container 370 may be from about 0.5 mL to about 4.0 mL, about 1.0 mL to about 3.5 mL, about 3.0 mL, about 3.1 mL, about 3.2 mL, about 3.3 mL, about 3.4 mL, about 3.5 mL. The delivered quantity of medicament may be related to the viscosity of the medicament and the hand-held nature of auto-injector 100. That is, in at least some embodiments, at certain viscosities, higher volumes of medicament may prohibit the ability of auto-injector 100 to complete an injection procedure in less than an acceptable amount of time, e.g., less than about 30 seconds. Thus, the delivered quantity of medicament from auto-injector 100 may be set such that an injection procedure, measured from 1) the point in time at which auto-injector 100 is placed onto a user's skin, to 2) the point in time at which auto-injector 100 is removed from the skin, is less than about 30 seconds or less than about another time period (e.g., less than about 25 seconds, less than about 20 seconds, less than about 15 seconds, or less than about 10 seconds).

When the delivered quantity and/or viscosity of the medicament is too high, auto-injector 100 may not be able to function as a handheld auto-injector, since the time required to complete the injection procedure may be higher than commercially or clinically acceptable for handheld devices. Again, as stated above, in embodiments where container 370 is used in a hand-held auto-injector, regardless of the nominal volume of container 370, the delivered quantity of medicament from container 370 may be set such that the injection procedure as defined above is completed in a relatively short period of time (so as to avoid the need for additional features to attach auto-injector 100 to the user so that auto-injector 100 is a wearable auto-injector).

However, it is contemplated that various embodiments of the present disclosure relate to wearable auto-injectors that deliver relatively large quantities of medicament (e.g., greater than about 3.5 mL) and/or have relatively longer injection procedure times as opposed to handheld auto-injectors (e.g., longer than about 30 seconds, longer than about 1 minute, longer than about 2 minutes, longer than about 5 minutes, or longer than about 1 hour) to complete an injection procedure as measured from 1) the point in time at which the auto-injector is placed onto a user's skin, to 2) the point in time at which the auto-injector is removed from the skin.

Container 370 may have about a 13 mm diameter neck, about a 45 mm length, and an internal diameter of about 19.05 mm. In another embodiment, container 370 may be a standard 3 mL container having an 8 mm crimp top, a 9.7 mm inner diameter, and a 64 mm length. In further embodiments, container 370 may have a length of about 64 mm to 74 mm, such as, for example, about 69.3 mm±0.15 mm (excluding a length of the neck of container 370 at second end 374). In embodiments including the neck, container 370 may have a length ranging from about 65 mm to 75 mm, such as, for example, about 70.8 mm±0.4 mm. These values are merely exemplary, and other suitable dimensions may be utilized as appropriate. In some examples, container 370 may be formed using conventional materials, and may be shorter than existing devices, which can help auto-injector 100 remain cost-effective and small. In some embodiments, container 370 may be a shortened ISO 10 mL cartridge.

Auto-injectors of the present disclosure may be configured to deliver highly viscous liquid to a patient. For example, auto-injectors of the present disclosure may be configured to deliver liquid having a viscosity from about 0 cP to about 100 cP, from about 5 cP to about 45 cP, from about 10 cP to about 40 cP, from about 15 cP to about 35 cP, from about 20 cP to about 30 cP, or about 25 cP.

Still referring to FIG. 1, container 370 may include a piston 378 movably disposed within a cavity of container 370. Piston 378 may be movable by a pressurized fluid expelled from a fluid source, such as, e.g., fluid source 350 (FIGS. 2A-2C). As described further herein, pressurized fluid (e.g., gas) expelled from fluid source 350 may translate piston 378 and container 370 horizontally along longitudinal axis 10 toward second end 130. The movement of piston 378 toward second end 130 may cause piston 378 to act against the contents within container 370 (e.g., drugs, medications, medicaments, etc.), which ultimately transfers force against container 370, thereby causing container 370 to move along longitudinal axis 10. In some embodiments, transverse auto-injectors may be oriented such that fluid source 350 and piston 378 are offset, or are otherwise not longitudinally aligned with one another.

Referring to FIGS. 2A-2C, a drive system 150 of auto-injector 100 is schematically depicted. Drive system 150 may be configured to provide a drive force to deliver a medicament 20 from container auto-injector 100 to a patient. Drive system 150 may include fluid source 350 fluidly coupled to one or more components of auto-injector 100, e.g., needle mechanism 200 and valve assembly 300. Drive system 150 may further include a high pressure (first) line 152, a low pressure (second line) 154, and a third line 156. Fluid source 350 may be operatively coupled to container 370 via high pressure line 152 and low pressure line 154.

Further, fluid source 350 may be fluidly coupled to valve assembly 300 via one or more of high pressure line 152 and low pressure line 154. Drive system 150 may further include a flow restrictor 170 disposed between high pressure line 152 and low pressure line 154.

Flow restrictor 170 may include a pressure restriction system configured to reduce a pressure of a pressurized fluid (e.g., from fluid source 350). Flow restrictor 170 may define a serpentine or tortuous path between an inlet and outlet of flow restrictor 170, thereby diverting a reduced-pressure flow of the fluid. Flow restrictor 170 may include a frit comprising a porous material (e.g., microporous or macroporous), such as, for example, plastics (particularly sintered plastics), ceramics, or other suitable materials. The average pore size of the porous material may be from about 0.5 to about 15 microns, from about 1 micron to about 10 microns, from about 3 microns to about 6 microns, or about 5 microns, in diameter. The porous material causes a pressure drop to be experienced in the pressurized gas flowing through it, and the pressure-reduced gas is then diverted to low pressure line 154 and container 370.

Still referring to FIGS. 2A-2C, valve assembly 300 may include a diaphragm 320 positioned between low pressure body portion 310 and high pressure body portion 330. Within valve assembly 300, diaphragm 320 defines a high pressure (first) cavity 161 and a low pressure (second) cavity 163. Valve assembly 300 may further include a high pressure (first) inlet 160, a low pressure (second) inlet 162, and a conduit 164. Conduit 164 is formed within a valve seat 166 that extends into the interior of valve assembly 300, and particularly low pressure cavity 163. High pressure cavity 161 may be in fluid communication with high pressure line 152 via high pressure (inlet 160, and low pressure cavity 163 may be in fluid communication with low pressure line 154 via low pressure inlet 162 and with third line 156 via conduit 164.

Drive system 150 may include a venting system 172 fluidly connected by a number of fluid lines or conduits. For example, venting system 172 may be in fluid communication with fluid source 350 via high pressure line 152, and with valve assembly 300 via third line 156. Venting system 172 may be configured to vent drive system 150 by releasing pressurized fluid into an interior cavity of auto-injector (e.g., defined between bottom cover 110 and the top cover) and/or into the atmosphere.

Still referring to FIGS. 2A-2C, container 370 may include a first end 372 and a second end 374. Container 370 also may include a cavity 376 having an opening at first end 372 and extending toward second end 374. Second end 374 may include a stopper 380 configured to assist with closing and/or sealing second end 374, and allow for a needle 288 (e.g., a staked needle) to be inserted into container 370. As seen in FIG. 1, stopper 380 may include a line seal, a protrusion disposed in a neck of container 370 (e.g., to reduce dead volume), and/or a septum 382. Septum 382 may be formed of an uncoated bromobutyl material, or another suitable material. Cavity 376 may be closed at first end 372 by piston 378. Piston 378 may include a fluoropolymer coated bromobutyl material, and, in some embodiments, may include a conical nose to help reduce dead volume within container 370. Piston 378 may include one or more rubber materials such as, e.g., halobutyls (e.g., bromobutyl, chlorobutyl, florobutyl) and/or nitriles, among other materials. As described in detail above, container 370 may store a medicament 20 (e.g., drug, fluid substance, etc.) within cavity 376.

Fluid source 350 may include a non-latching can or a latching can. Fluid source 350 may be configured to dispense liquid propellant for boiling outside of fluid source 350 so as to provide a pressurized gas (vapor pressure) that acts on piston 378 in container 370. In some embodiments, once opened, the latching can may be latched open so that the entire contents of propellant is dispensed therefrom. Alternatively, in some embodiments, fluid source 350 may be selectively controlled, including selectively activated and deactivated. For example, in an alternative embodiment, the flow of pressurized gas from fluid source 350 may be stopped after flow is initiated.

The fluid from fluid source 350 may be any suitable propellant for providing a vapor pressure to drive piston 378 relative to container 370, and container 370 relative to the housing of auto-injector 100. In certain embodiments, the propellant may be a liquefied gas that vaporizes to provide a vapor pressure. In certain embodiments, the propellant may be or contain a hydrofluoroalkane ("HFA"), for example HFA134a, HFA227, HFA422D, HFA507, or HFA410A. In certain embodiments, the propellant may be or contain a hydrofluoroolefin ("HFO") such as HFO1234yf or HFO1234ze, an organic gas (e.g., carbon dioxide ($CO_2$), etc.), a cryogenic gas (e.g., Argon (Ar), Helium (He), etc.), a hydrocarbon gas (e.g., propane, butane, propylene, ethane, methane, etc.) or an inorganic gas (e.g., Ammonia, Nitrogen Dioxide ($NO_2$), Nitrous Oxide ($N_2O$), etc.). In some embodiments, fluid source 350 may be a high-pressure canister configured to hold a compressed gas.

In the pre-activated state of auto-injector 100 shown in FIG. 2A, needle 288 may be spaced apart from the second end 374 of container 370. To move auto-injector 100 from the pre-activated state of FIG. 2A, fluid source 350 may be activated to move container 370 along longitudinal axis 10 toward needle 288. Fluid source 350 may be actuated so as to move to an open configuration in which propellant may exit the fluid source 350 as a pressurized gas. As described in further detail below, fluid source 350 may be actuated in response to one or more components of needle mechanism 200 (e.g., can actuator 230) contacting fluid source 350. In some embodiments, the actuation is irreversible such that the flow of pressurized gas from fluid source 350 is not able to be stopped.

When fluid source 350 is actuated, pressurized gas may flow through high pressure line 152 and flow restrictor 170, and then to container 370. Some pressurized gas from high pressure line 152 may be diverted to high pressure cavity 161 via high pressure inlet 160. As seen in FIG. 2B, this may cause diaphragm 320 to move into low pressure cavity 163 and toward conduit 164, thereby sealing valve seat 166. Downstream of flow restrictor 170, reduced-pressure gas may be diverted to low pressure cavity 163 via low pressure line 154 and low pressure inlet 162. The pressure difference between high pressure cavity 161 and low pressure cavity 163 may provide the force required to seal conduit 164 by diaphragm 320. The low pressure line 154 may further direct the reduced-pressurized gas from flow restrictor 170 to container 370. The reduced-pressurized gas may initiate movement of container 370 toward needle 288.

Stated differently, with needle 288 not yet in fluid communication with container 370, activation of fluid source 350 may apply a pressure against medicament 20 contained in cavity 376, which may then be applied to container 370 itself. This pressure may cause container 370 to move toward the needle 288, thereby forcing needle 288 through septum 382 of stopper 380. In this instance, as seen in FIG. 2B, needle 288 is in fluid communication with the contents of container 370 (e.g., medicament 20). The reduced-pressure gas from low pressure line 154 may subsequently urge piston 378 toward second end 374 to expel medicament 20 through container 370 until piston 378 reaches second end 374 (and bottoms out).

In other words, once needle 288 is in fluid communication with container 370, further movement of piston 378 toward second end 374 may urge medicament 20 through needle 288. As described further herein, pressurized gas from fluid source 350 may also drive movement of one or more components of needle mechanism 200 (e.g., can actuator 230, shuttle actuator 260, indicator slide 270, etc.) to drive injection of a needle 286 into a user.

Referring now to FIG. 2C, when piston 378 bottoms out at second end 374, the pressure across high pressure cavity 161 and low pressure cavity 163 may equilibrate, thereby causing diaphragm 320 to lift off of valve seat 166 and open conduit 164. This may allow the gas from low pressure line 154 to travel to venting system 172 via conduit 164 and third line 156 where the gas may vent out of drive system 150. It should be appreciated that fluid source 350 may be configured to contain enough pressurized fluid so that release of the pressurized gas may actuate both movement of container 370 relative to the housing of auto-injector 100 and movement of piston 378 relative to cavity 376. In some instances, fluid source 350 may contain excess pressurized gas, i.e., more fluid than is necessary to complete delivery of medicament 20 from container 370. Release of the pressurized fluid from within drive system 150 may allow for the movement of one or more components of needle mechanism 200 (e.g., can actuator 230, shuttle actuator 260, indicator slide 270, etc.) to initiate retraction of needle 286 back into auto-injector 100.

Figure 3:
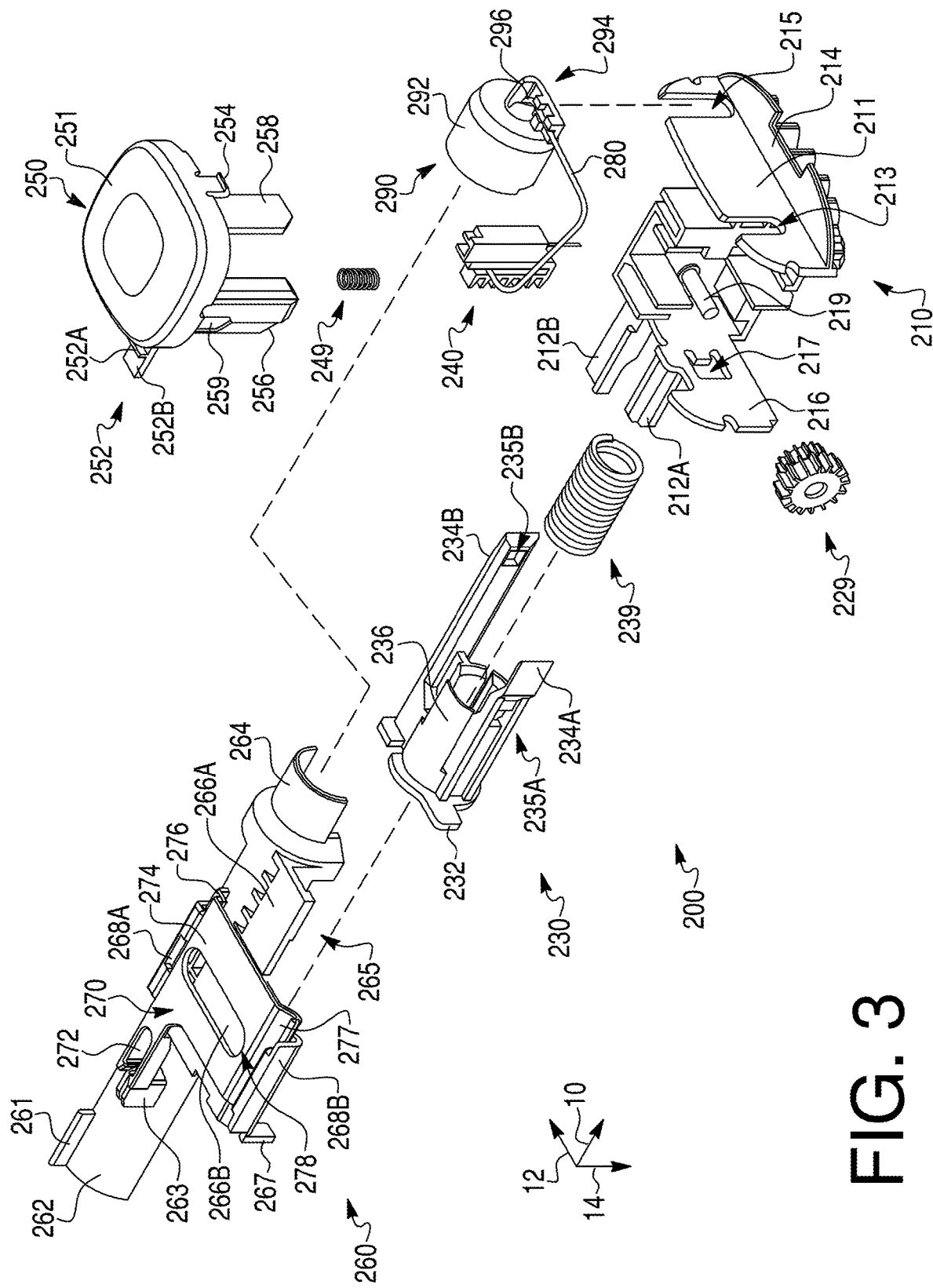
FIG. 3 is an exploded perspective view of a needle mechanism of the auto-injector of FIG. 1, according to an example of the disclosure.

Referring now to FIG. 3, an implementation of needle mechanism 200 is depicted. As briefly described above, needle mechanism 200 may include carrier 210, can actuator 230, shuttle actuator 260, button 250, and sterile connector 290. In some embodiments, shuttle actuator 260 is coupled to container 370 such that shuttle actuator 260 and container 370 move together. A resilient member 239 is disposed within can actuator 230, and compressed between can actuator 230 and carrier 210 prior to activation of auto-injector 100.

Figure 4A:
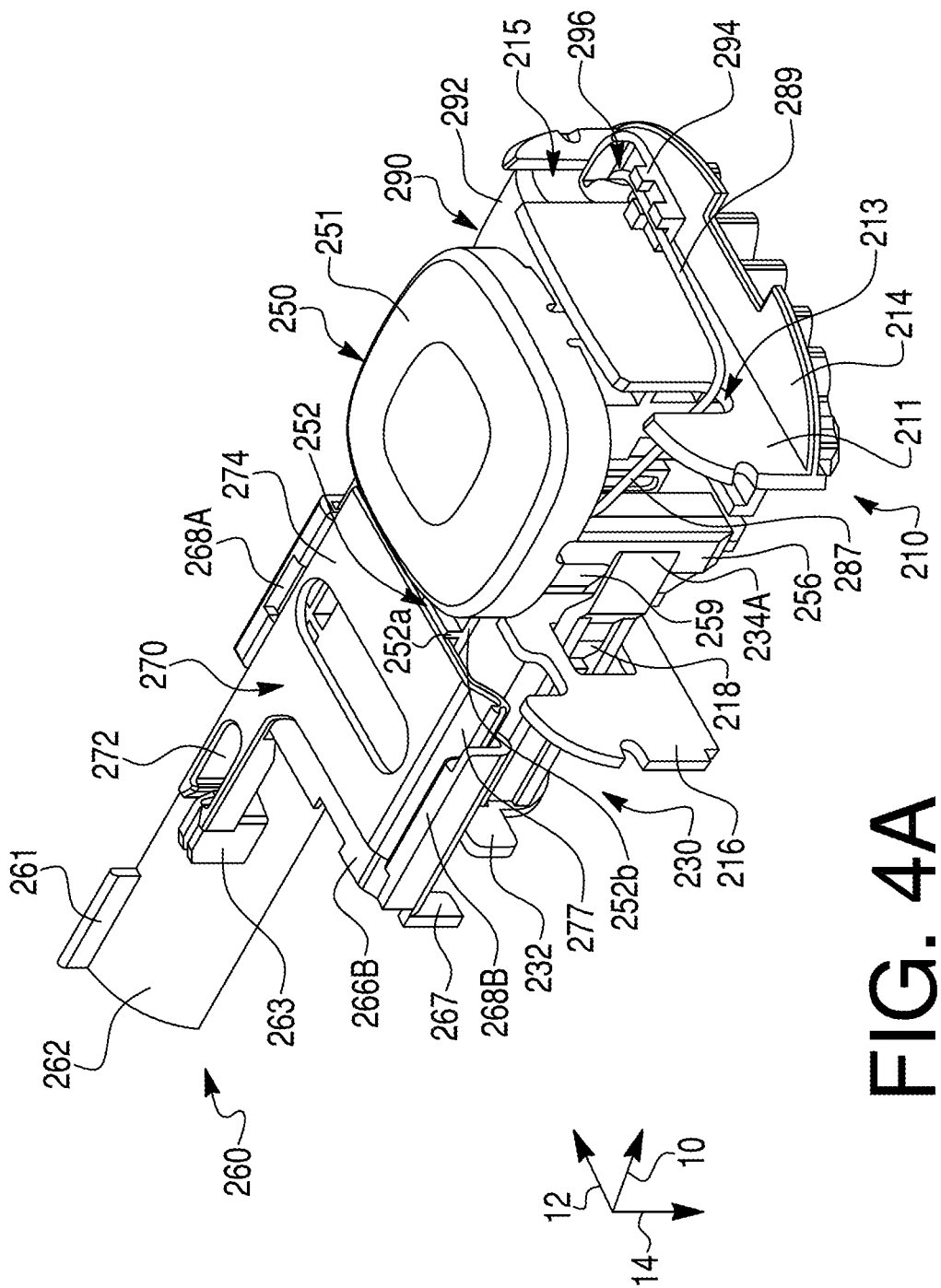
FIG. 4A is a perspective view of the needle mechanism of FIG. 3, according to an example of the disclosure.

FIG. 4A shows the components of FIG. 3 in an assembled state prior to activation of auto-injector 100. In this state, button 250 may be located in a first (extended) position and can actuator 230 may be positioned at a first position relative to carrier 210. Can actuator 230 is held in its first position by a first impediment 218 positioned on carrier 210. First impediment 218 is in a path of can actuator 230, preventing horizontal movement of can actuator 230. In particular, first impediment 218 interacts with and engages features on a first leg 234A of can actuator 230. Container 370 is prevented from establishing fluid connection with fluid conduit 280 by a stop tab 252 (e.g., an impediment) extending from button 250 and engaging shuttle actuator 260 (which is coupled to container 370). Stop tab 252 may be positioned in the path of shuttle actuator 260 (e.g., via a ridge 252b), preventing horizontal movement of shuttle actuator 260 (and container 370 connected to shuttle actuator 260) in a direction toward sterile connector 290 and fluid conduit 280.

In some embodiments, stop tab 252 may be further engaged with indicator slide 270 (e.g., at a protrusion 252a), thereby obstructing movement of indicator slide 270 in the same direction. In other embodiments, stop tab 252 may omit protrusion 252a entirely, and a top (and/or outer) cover 118 of the housing of auto-injector 100 may include a stop tab 119 (e.g., an impediment) for obstructing movement of indicator slide 270 in the direction toward sterile connector 290 (see FIG. 4B). Stop tab 119 may extend radially inward from an interior surface of top cover 118 in a direction parallel to transverse axis 14, and may be positioned along top cover 118 at a location that aligns with a first end of indicator slide 270. In other words, stop tab 119 may extend vertically within auto-injector 100. Accordingly, stop tab 119 may be configured to engage/abut indicator slide 270 and obstruct movement of indicator slide 270 in a direction parallel to longitudinal axis 10 (toward sterile connector 290). Stop tab 119 may be sized and/or shaped to abut against body 274 when button 250 is in a first (unactuated) position, and even after button 250 is actuated. Stop tab 119 may hold indicator slide 270 in place so that it can be mated/coupled to shuttle actuator 260 (via engagement between a leg 254 of indicator slide 270 and a fastening mechanism 263 of shuttle actuator 260), after fluid released from fluid source 350 drives the container 370 (and shuttle actuator 260) in the horizontal direction toward sterile connector 290. It should be appreciated that, in further embodiments, auto-injector 100 may include protrusion 252a on stop tab 252 and stop tab 119 on top cover 118.

In this state, prior to actuation of auto-injector 100, indicator slide 270 may be in a first position relative to shuttle actuator 260. In embodiments where a housing of auto-injector 100 includes a window for visualizing needle mechanism 200, a user may identify a relative state of auto-injector 100 through the window based on visualizing the first position of indicator slide 270. As described in further detail herein, in some embodiments, indicator slide 270 may include a graphical interface on a body 274 that indicates the relative position of indicator slide 270 and/or a state of auto-injector 100. Furthermore, the first position may be visually indicated to a user based on a sticker, color, or the like, positioned on shuttle 260 visible from outside of the auto-injector through both the window on the outer surface of the auto-injector and through the window 278 of indicator slide 270.

Prior to actuation, a leg 272 of indicator slide 270 may be positioned adjacent to, but disengaged from, a fastening mechanism 263 of shuttle actuator 260. As described in further detail herein, shuttle actuator 260 may initially be uncoupled from indicator slide 270, but may ultimately become coupled to indicator slide 270 so that shuttle 260 and indicator slide 270 move together. A second impediment 225 may be positioned on an opposite side of carrier 210 (see FIG. 6), and may engage with features of a second leg 234B of can actuator 230.

A user may remove peel tab 140 from bottom cover 110 (see FIG. 1) to expose one or more openings along a (bottom) tissue-engaging surface of bottom cover 110, and also to allow button 250 to be depressed (further explanation of peel tab 140 is found below). Button 250 may be actuated by applying a downward force onto its body 251, thereby moving button 250 from the first (extended) position to a second (depressed) position. Prior to activation of auto-injector 100, movement of shuttle actuator 260 relative to carrier 210 may be inhibited due to stop tab 252 abutting against a portion of shuttle actuator 260. Accordingly, moving button 250 to the second position may disengage stop tab 252 from shuttle actuator 260, thereby permitting movement of shuttle actuator 260 relative to (e.g., horizontally toward) carrier 210. With top cover 118 including stop tab 119 in engagement with indicator slide 270 (see FIG. 4B), movement of indicator slide 270 toward sterile connector 290 is initially inhibited as shuttle actuator 260 moves away from carrier 210 upon initial actuation of button 250.

Figure 5:
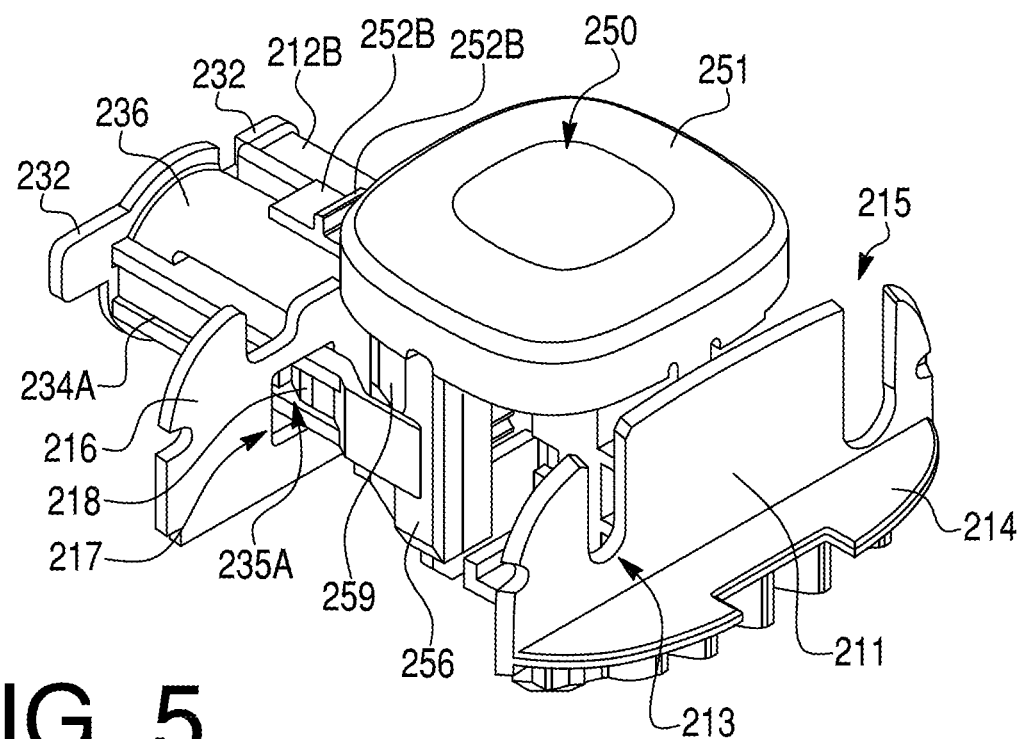
FIGS. 5-6 are partial perspective views of the needle mechanism of FIG. 3, according to an example of the disclosure.
Figure 6:
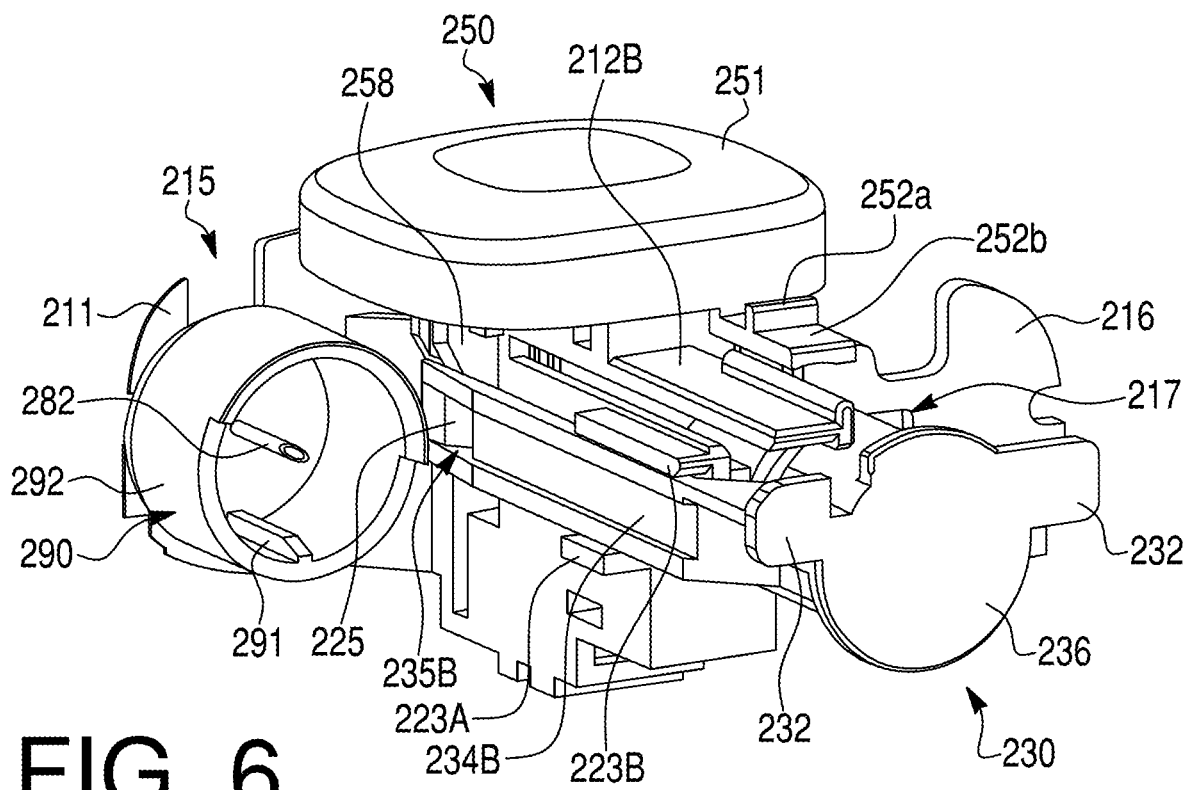
Figure 10:
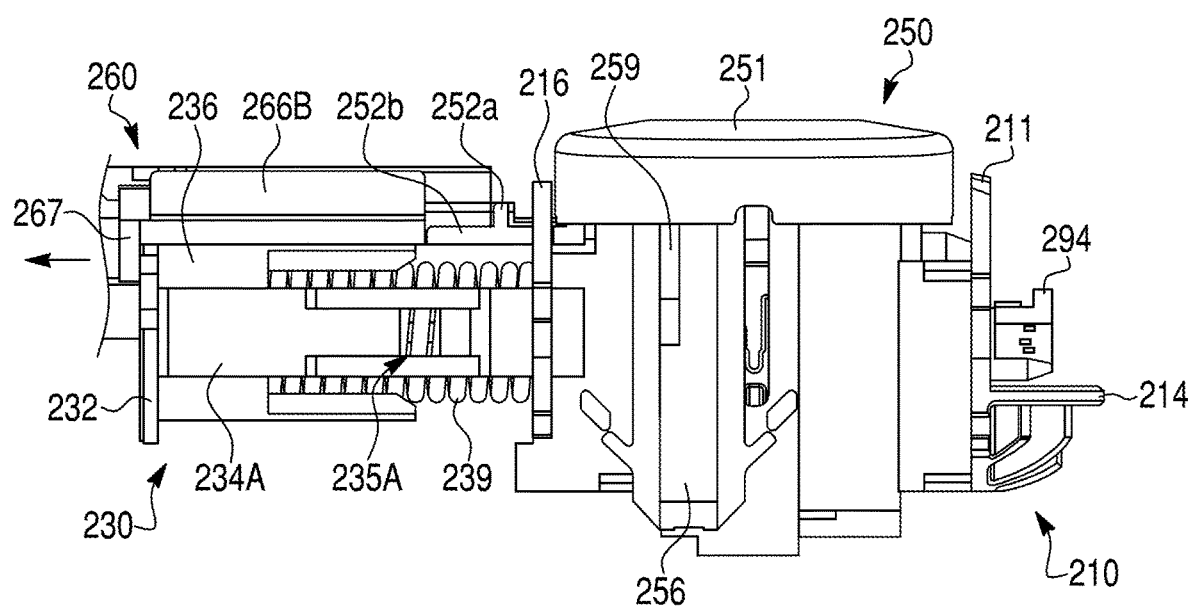

Referring to FIGS. 5-6 and 10, moving button 250 in a downward vertical direction may cause a first leg 256 of button 250 to push first leg 234A laterally or radially outward, out of engagement with first impediment 218. Moving button 250 downward also may cause a second leg 258 of button 250 to push second leg 234B laterally or radially outward, out of engagement with second impediment 225. In the embodiment shown, first leg 234A and second leg 234B move in opposite directions when button 250 is pushed downward. The outward movement of first leg 234A and second leg 234B allows them to clear impediments 218 and 225, respectively.

Figure 7:
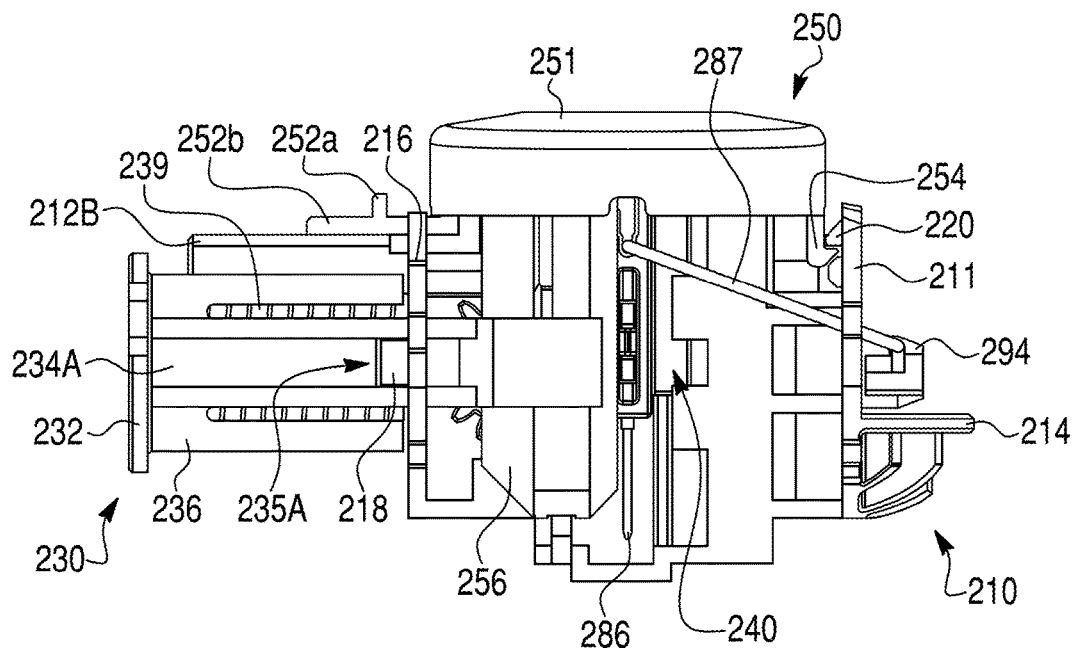
FIGS. 7-10 are partial side views of the needle mechanism of FIG. 3, according to an example of the disclosure.
Figure 8:
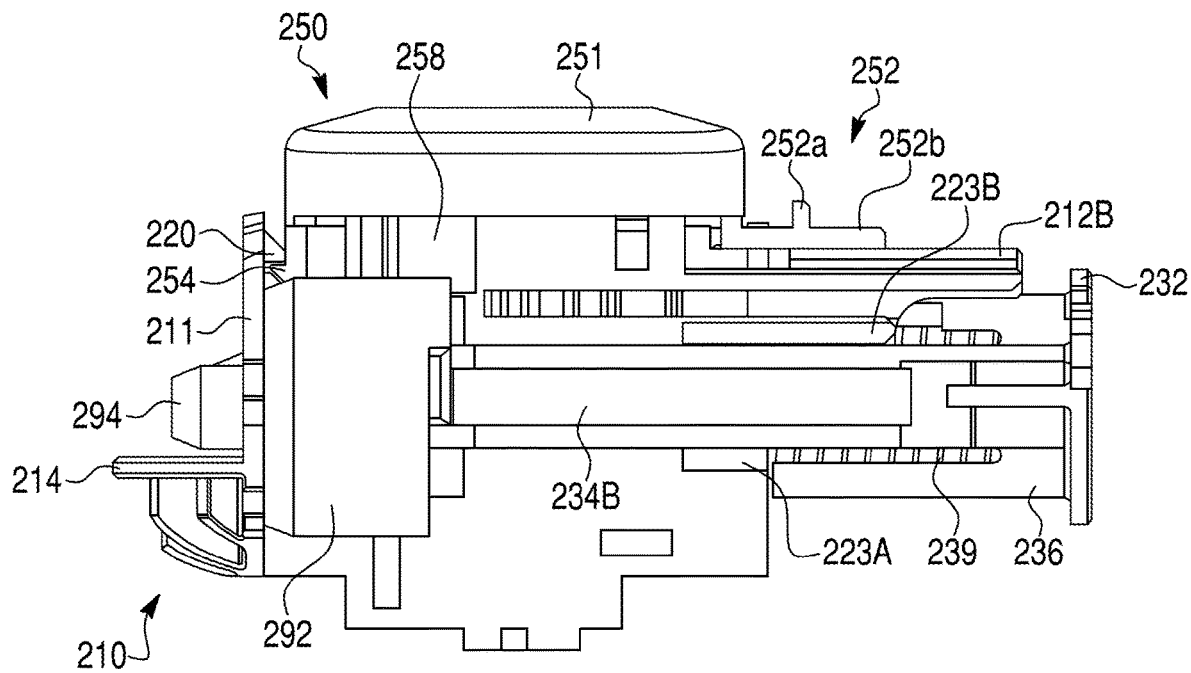

Referring now to FIGS. 7-8, resilient member 239 is disposed within or otherwise coupled to can actuator 230. Prior to activation of auto-injector 100, resilient member 239 is compressed in a first energy-storing state between can actuator 230 and carrier 210. After button 250 is depressed, and can actuator 230 is cleared from first impediment 218 and/or second impediment 225, resilient member 239 may move from its first energy-storing state (compression, FIG. 9) to a first energy-released state (expanded, FIG. 10) to push can actuator 230 away from carrier 210. This release of energy from resilient member 239 (expansion) moves can actuator 230 horizontally from its first position to its second position in order to activate an energy source (e.g., fluid source 350) by, for example, directly contacting a portion of the energy source. For example, can actuator 230 may contact and move a valve stem of fluid source 350 into an open configuration, to enable the flow of fluid/gas from fluid source 350. In other examples, the valve stem of fluid source 350 may be positioned within or adjacent to valve assembly 300 and stationary, such that can actuator 230 may push against the stationary valve stem to move fluid source 350 to the open configuration. In some embodiments, a feedback (e.g., tactile, audible, etc.) may be generated by needle mechanism 200 in response to can actuator 230 contacting fluid source 350, to indicate initiation of a dose delivery sequence to a user.

Figure 9:
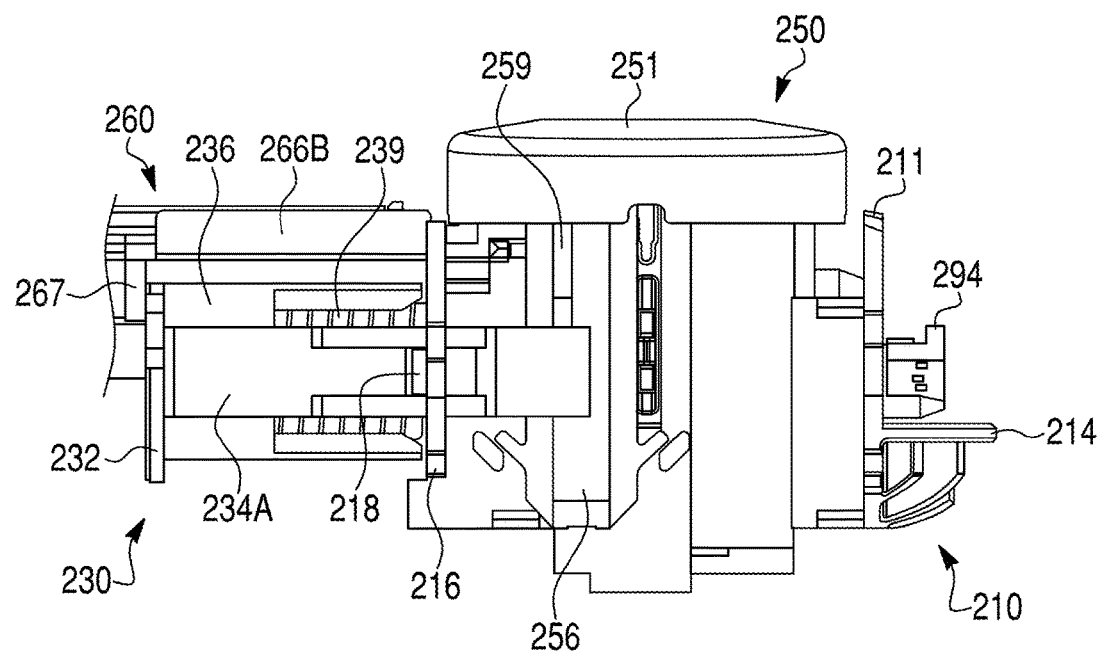
Figure 11A:
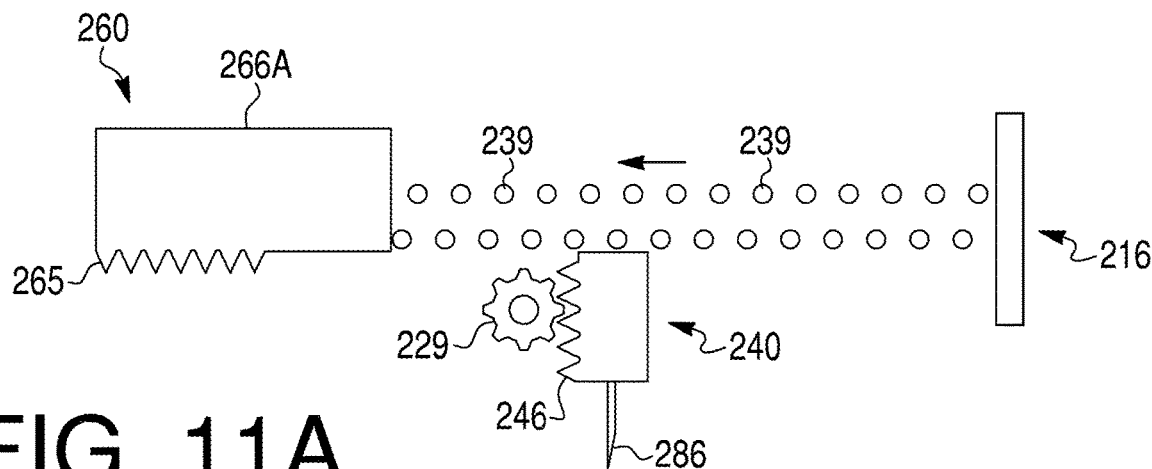
FIGS. 11A-11C are schematic illustrations of portions of the needle mechanism of FIG. 3, according to an example of the disclosure.

In some embodiments, as seen in FIG. 4A, a tab 232 on a first end of can actuator 230 may be separated from a stop 267 of shuttle actuation 260 prior to actuation of button 250 (when can actuator 230 is in the first position). In this instance, tab 232 may move toward stop 267 when resilient member 239 is expanded and can actuator 230 is moved horizontally to the second position. Accordingly, as seen in FIG. 11A, shuttle actuator 260 remains stationary as resilient member 239 expands, thereby moving can actuator 230 from the first position to the second position. In other embodiments, as seen in FIG. 9, tab 232 may be in contact with stop 267 when can actuator 230 is in the first position, such that can actuator 230 may move shuttle actuator 260 horizontally when transitioning to the second position.

Shuttle actuator 260 may be configured to move with can actuator 230 from the second position to a third position given the established connection between tab 232 of can actuator 230 and stop 267 of shuttle actuator 260. Thus, when shuttle actuator 260 moves in the horizontal direction from its first state to its second state, it pushes can actuator 230 in the same horizontal direction (see FIG. 11B). That is, once energy or fluid is release from the energy source (e.g., fluid source 350), the released energy or fluid acts on container 370 in the opposite horizontal direction as that of can actuator 230 when resilient member 239 is initially expanded to the energy-released state described above. The released energy or fluid will push container 370, shuttle actuator 260 (coupled to container 370), and can actuator 230 (now coupled to shuttle actuator 260 via the engagement of stop 267 and tab 232) in the opposite horizontal direction, compressing resilient member 239.

This same movement of components in the opposite horizontal direction establishes fluid communication between container 370 and fluid conduit 280. The fluid communication is established when container 370 moves onto a stationary, second end (needle) 288 of fluid conduit 280 (see FIG. 2B), forcing needle 288 through stopper 380 of container 370. Still further, this same opposite horizontal movement of components may be configured to drive injection of a first end (needle) 286 of fluid conduit 280 (see FIG. 33) out of auto-injector 100 and into a patient.

Figure 11B:
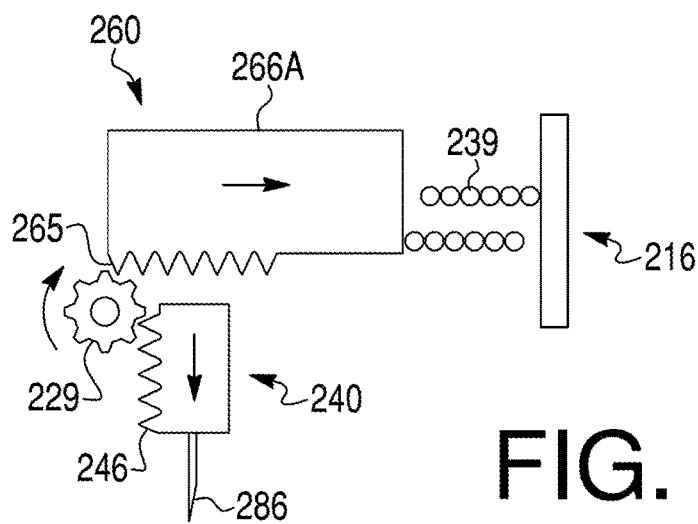

In particular, referring to FIGS. 11A and 11B, the movement of container 370 and shuttle actuator 260 in the opposite horizontal direction causes a rack 265 of shuttle actuator 260 to rotate a gear 229 in a first rotational direction (e.g., clockwise), which forces driver 240 in the downward vertical direction (needle injection) via contact between gear 229 and a rack 246 of driver 240. As shown and described in further detail below, gear 229 may include two body portions of varying sizes such that each body portion may have a different pitch ratio (see FIG. 21). For example, gear 229 may have a 4:3 pitch ratio difference between the two body portions, and the body portions may have a different diameter relative to one another, such that gear 229 may move shuttle actuator 260 along a first distance (e.g., ranging from about 1 mm to 6 mm) while simultaneously moving driver 240 along a second distance (e.g., ranging from about 6 mm to 10 mm) that is different (e.g., greater) than the first distance. For example, 6 mm of travel of shuttle actuator 260 may correspond to 8 mm of travel for driver 240. It is further noted that gears or gear portions of the present disclosure are not limited to a specific pitch, diameter, length, and/or combination thereof. The gears and gear portions can be adjustable and may be modified to accommodate any patient needle insertion depth. As described above, once container 370 is in fluid communication with fluid conduit 280, and first end 282 of fluid conduit 280 is deployed into a patient (FIG. 11B), further release of energy or fluid from fluid source 350 will move piston 378 through container 370, expelling medicament 20 into the patient (see FIG. 2C).

Figure 4B:
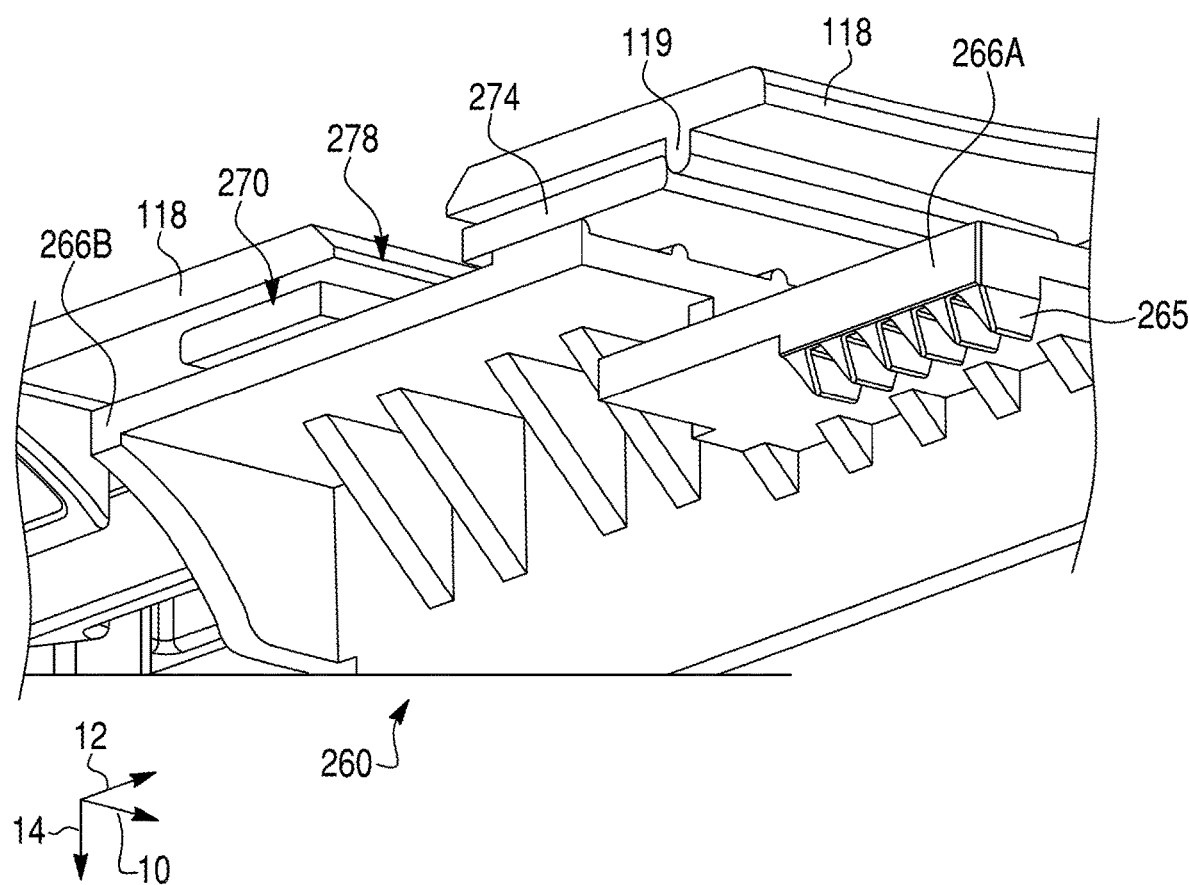
FIG. 4B is a cross-sectional perspective view of a portion of the auto-injector of FIG. 1, according to an example of the disclosure.

In some embodiments, a feedback (e.g., tactile, audible, etc.) may be generated by needle mechanism 200 in response to shuttle actuator 260 contacting can actuator 230 (e.g., via engagement between stop 267 and tab 232) to indicate delivery of a dose to the user. With button 250 having been moved to a second position (FIG. 10) initiate the dose delivery sequence described above, stop tab 252 may be positioned along a new plane that is relatively lower than when button 250 was in a first position (FIG. 9). Accordingly, stop tab 252 may now engage one or more of shuttle actuator 260 and/or indicator slide 270 as they move horizontally toward button 250. In this state, leg 272 may move toward, and engage, fastening mechanism 263 (FIG. 4A) such that shuttle actuator 260 is coupled to indicator slide 270 and moves together with indicator slide 270 after this coupling/locking. In particular, stop tab 252 (and/or stop tab 119) may maintain the horizontal position of indicator slide 270 (preventing indicator slide 270 from moving toward sterile connector 290) while shuttle actuator 260 moves from its first state to its second state, allowing shuttle actuator 260 to interlock with indicator slide 270. As seen in FIG. 4A and as described above, a protrusion 252*a* on stop tab 252 may abut against indicator slide 270 while a ridge 252*b* of stop tab 252 may contact shuttle actuator 260. In the embodiment, protrusion 252*a* extends parallel to transverse axis 14 and ridge 252*b* extends parallel to longitudinal axis 10, such that protrusion 252*a* is perpendicular relative to ridge 252*b*. Upon actuation of button 250, protrusion 252*a* may maintain contact with indicator slide 270, preventing movement of indicator slide 270 in the horizontal direction toward sterile connector 290, even after shuttle actuator 260 has disengaged ridge 262*b*. It should be appreciated that protrusion 252*a* may have a length sufficient to maintain contact with indicator slide 270 after movement of button 250 from a first (unactuated) position to a second (actuated) position. In other embodiments, as seen in FIG. 4B, stop tab 119 may maintain contact with indicator slide 270 in lieu of and/or in addition to protrusion 252*a*.

Therefore, upon actuation of auto-injector 100, movement of shuttle actuator 260 from its first state to its second state causes a second indicator (positioned on the surface of shuttle actuator 260), to be visible through the window of the housing of auto-injector 100 and through window 278. In this instance, the window may align with a portion of body 274 and/or a window 278 of indicator slide 270, which may thereby reveal a portion of second platform 266B (containing the second indicator) disposed underneath body 274. As described in further detail herein, second platform 266B may include one or more graphical interfaces (e.g., color, text, marking, etc.) indicative of a state of auto-injector 100 when viewable by a user through window 278. The first and second indicators on second platform 266B may be different colored and/or patterned pieces of material, stickers, etching, or any other suitable mechanism for providing a different visual cue to the user.

Figure 11C:
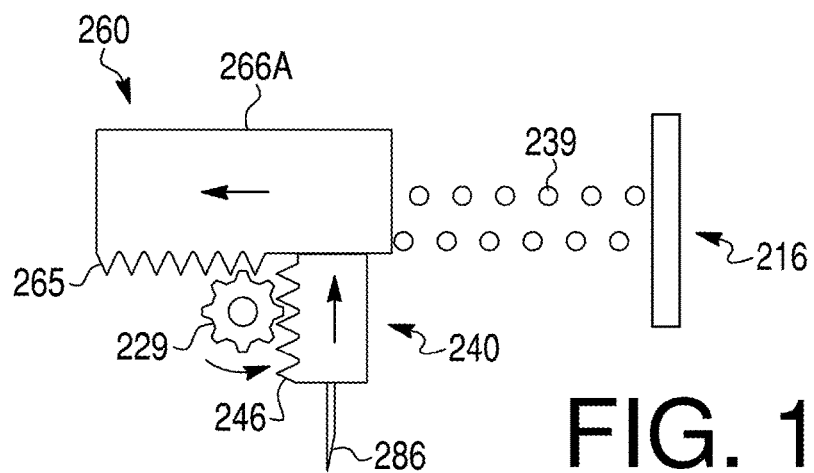

Upon completing delivery of the medicament 20 (e.g., when piston 378 bottoms out at second end 374), the pressure acting on container 370 may be reduced and/or eliminated. For example, venting system 172 (FIG. 2C) may release a pressure generated within valve assembly 300 upon delivering the medicament 20 through fluid conduit 280. The absence of a fluid force acting on container 370 allows resilient member 239 to move from its second energy-storing state (compression, shown in FIG. 11B) to its second energy-released state (expansion, FIG. 11C). This expansion or movement of resilient member 239 may drive can actuator 230 (and shuttle actuator 260 coupled thereto) in a second horizontal direction. The movement of shuttle actuator 260 horizontally causes rack 265 to drive gear 229 in a second rotational direction (e.g., counter-clockwise) that is opposite of the first rotational direction. This opposing rotation retracts needle 286 out of the patient and into auto-injector 100 by forcing driver 240 in the upward vertical direction. Thus, resilient member 239 indirectly drives gear 229.

With shuttle actuator 260 and can actuator 230 moved horizontally by the expansion of resilient member 239 (e.g., via the contact between tabs 232 and shuttle actuator 260), indicator slide 270 may similarly move with shuttle actuator 260. Accordingly, indicator slide 270 may move to a third position, viewable through the window of the housing of auto-injector 100 to indicate a final state of auto-injector 100. In some embodiments, a feedback (e.g., tactile, audible, etc.) may be generated by needle mechanism 200 in response to resilient member 239 expanding and/or driver 240 moving vertically to retract fluid conduit 280 into the housing of auto-injector 100, thereby indicating completion of the dose delivery to the user. In some embodiments, driver 240 may contact a surface of carrier 210 or a top interior surface of the housing of auto-injector 100 (e.g., top cover 118), thereby generating a feedback (e.g. tactile, audible) indicating completion of the delivery. In other embodiments, can actuator 230 and/or shuttle actuator 260 may contact one or more components and/or surfaces within auto-injector 100 to generate a corresponding feedback when the dose is delivered to the user (with the force being provided by the second or subsequent expansion of resilient member 239 after dose delivery). This movement of the indicator slide 270 with the shuttle 260 may move window 278 out of alignment with the window on the exterior of the auto-injector 100. Instead, a surface of indicator slide 270 containing a third indicator (different than the first and second indicators) may now be visible through window of auto-injector 100.

Further Description of Individual Components

Peel Tab

Referring back to FIG. 1, auto-injector 100 may further include a peel tab 140 coupled to bottom cover 110. Peel tab 140 may include a first end 142 positioned at least partially beneath, and extending through one or more openings in bottom cover 110. Peel tab 140 may further include a second end 144 extending outwardly from an end of bottom cover 110 at various suitable lengths, shapes, sizes, and/or configurations. Second end 144 may be selectively graspable by a user to remove peel tab 140 from bottom cover 110. It should be appreciated that peel tab 140 may be configured to enclose the one or more openings along bottom cover 110 when coupled thereto. Peel tab 140 may be configured to prevent the depression of button 250 when peel tab 140 is coupled to auto-injector 100.

Figure 12:
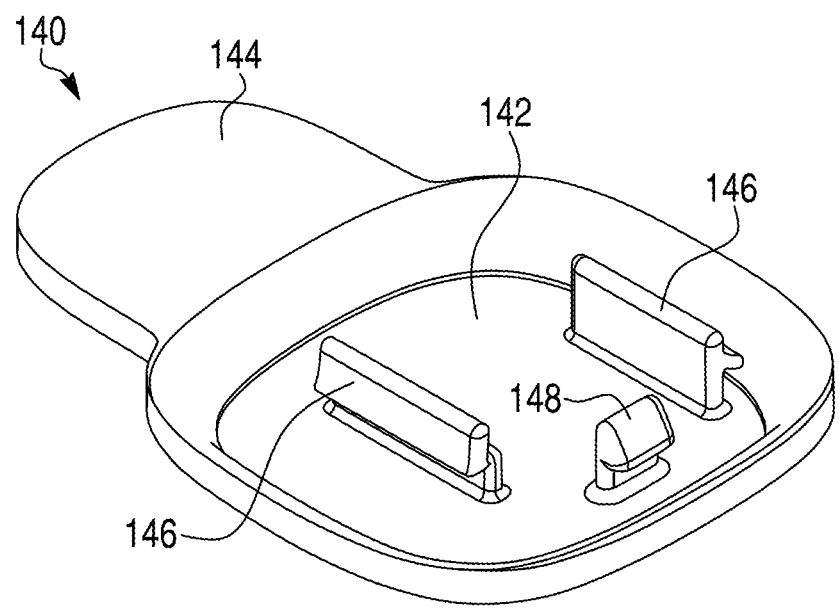
FIGS. 12-13 are perspective views of peel tabs of the auto-injector of FIG. 1, according to an example of the disclosure.

First end 142 may include a pair of tabs 146 and a clasp 148 extending through bottom cover 110 and into the interior of auto-injector 100 when peel tab 140 is coupled to bottom cover 110. Peel tab 140 may be disposed on at least a portion of the exterior (tissue-engaging) surface of bottom cover 110. As best seen in FIG. 12, the pair of tabs 146 may include vertical stops and/or projections extending outwardly (e.g., upward) from an interior surface of first end 142. As described in detail herein, the pair of tabs 146 may be configured to form an impediment that obstructs actuation (e.g., vertical translation) of button 250 until removal of peel tab 140 from bottom cover 110 (see FIGS. 14-18). In the embodiment, the pair of tabs 146 may have varying sizes (e.g., length, height, width) relative to one another, corresponding to a height of a portion of button 250 (e.g., first leg 256, second leg 258) that the tab 146 will be aligned with when peel tab 140 is coupled to bottom cover 110. Clasp 148 may include a hook or other suitable fastening mechanism capable of securing peel tab 140 to bottom cover 110.

Figure 13:
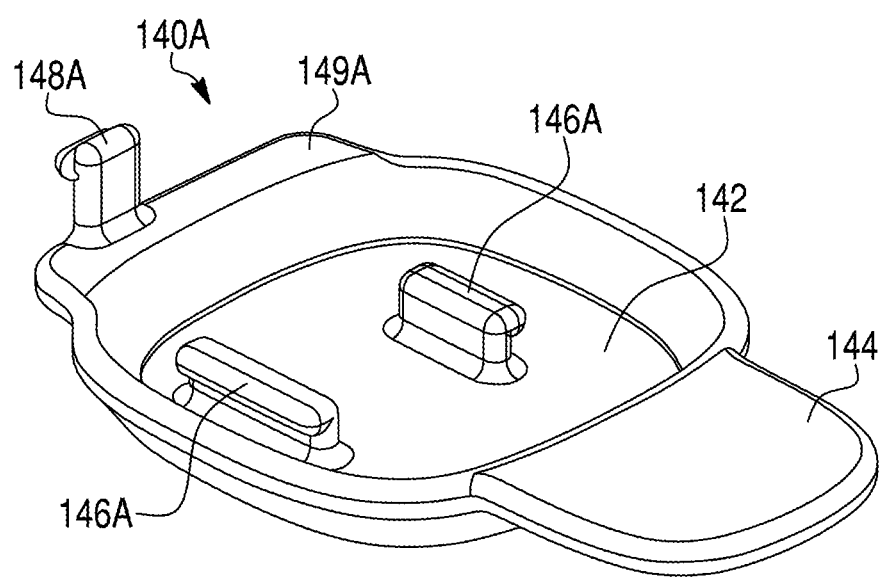

FIG. 13 shows another implementation of a peel tab 140A, which may be compatible with bottom cover 110 in a manner substantially similar to that shown and described above. Peel tab 140A may include a pair of tabs 146A extending outward from first end 142, and a clasp 148A extending outward from a ledge 149A. In the embodiment, ledge 149A may be positioned along a plane that is elevated relative to first end 142, such that clasp 148A may located along a different surface than the pair of tabs 146A. It should be appreciated that a position, size, and arrangement of the tabs 146, 146A and clasps 148, 148A of peel tabs 140, 140A shown and described herein are merely exemplary, such that various other suitable configurations may be possible without departing from a scope of this disclosure.

Figure 14:
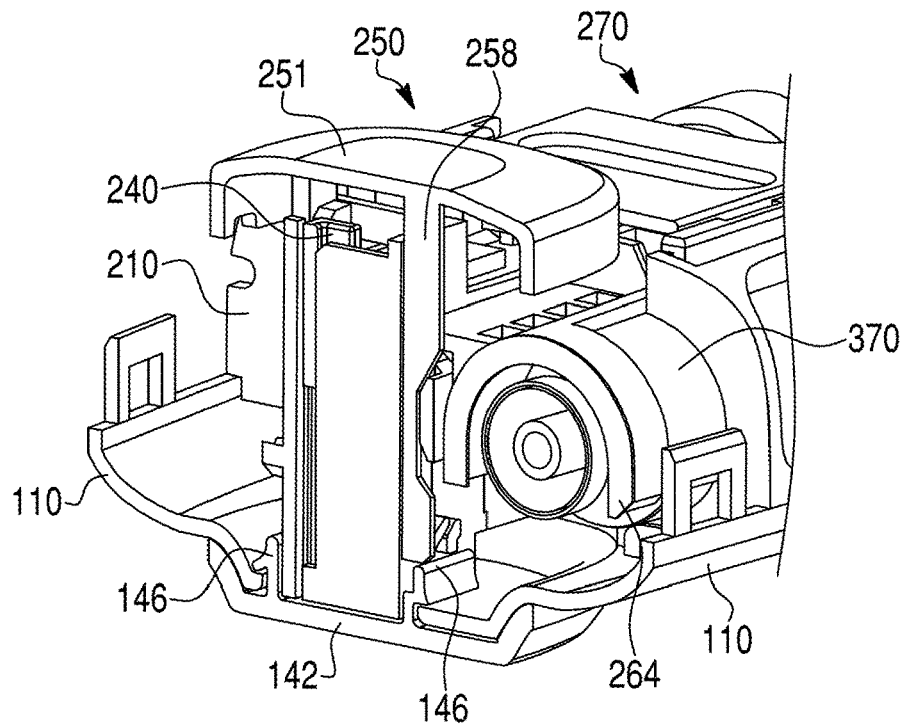
FIGS. 14-15 are cross-sectional views of the peel tabs of FIGS. 12-13 coupled to the auto-injector of FIG. 1, according to an example of the disclosure.
Figure 15:
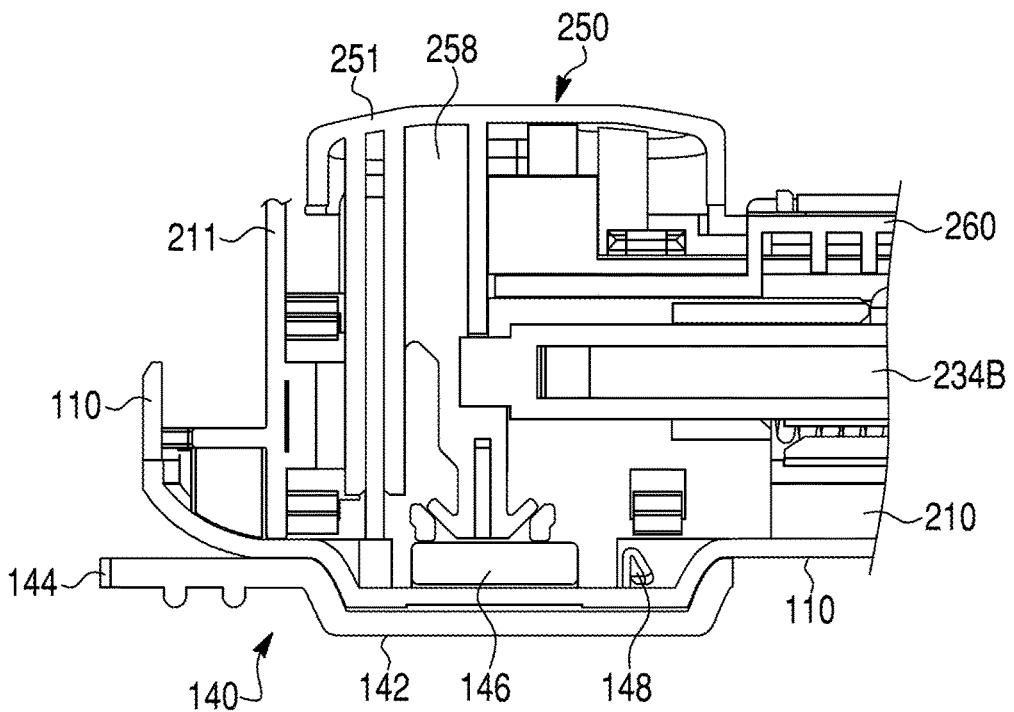

In the embodiment, as seen in FIGS. 14-15, peel tab 140 may be coupled to bottom cover 110 and the pair of tabs 146 may be received through bottom cover 110 and into a cavity of the housing. At least one of the pair of tabs 146 may abut a portion of button 250, e.g., legs 256, 258. Particularly, tabs 146 may abut against a bottom end of the one or more of legs 256, 258 such that the depression of button 250 may be prevented until peel tab 140 is removed by a user. Accordingly, peel tab 140 may be configured to inhibit movement of button 250 due to tabs 146 forming an impediment obstructing a (downward) vertical travel path of button 250 until removal of peel tab 140. As seen in FIG. 15, clasp 148 may extend into bottom cover 110 and engage at least an interior surface (and/or feature) of the housing to maintain an attachment between peel tab 140 and bottom cover 110 until a user manually removes peel tab 140.

Figure 16:
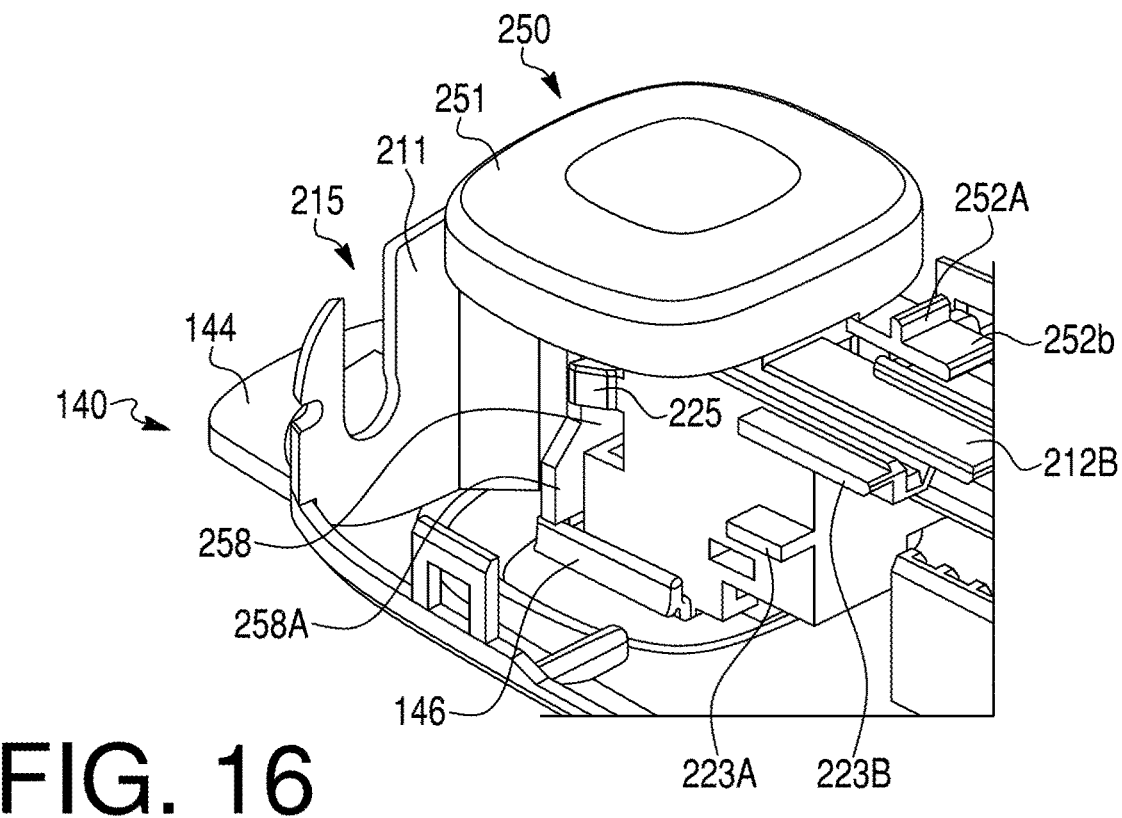
FIGS. 16-17 are partial perspective views of the peel tabs of FIGS. 12-13 coupled to the auto-injector of FIG. 1, according to an example of the disclosure.

In some embodiments, as seen in FIG. 16, button 250 may include an extension 258A at a bottom end of second leg 258. Extension 258A may be sized, shaped, and configured to abut against at least one of the pair of tabs 146. In this instance, peel tab 140 may be configured to inhibit movement of button 250 due to tab 146 forming an impediment obstructing a (downward) travel path of extension 258A. A user may remove peel tab 140 (e.g., by applying a downward force onto second end 144) to separate peel tab 140 from bottom cover 110, thereby removing the impediment against extension 258A and permitting actuation of button 250.

Figure 17:
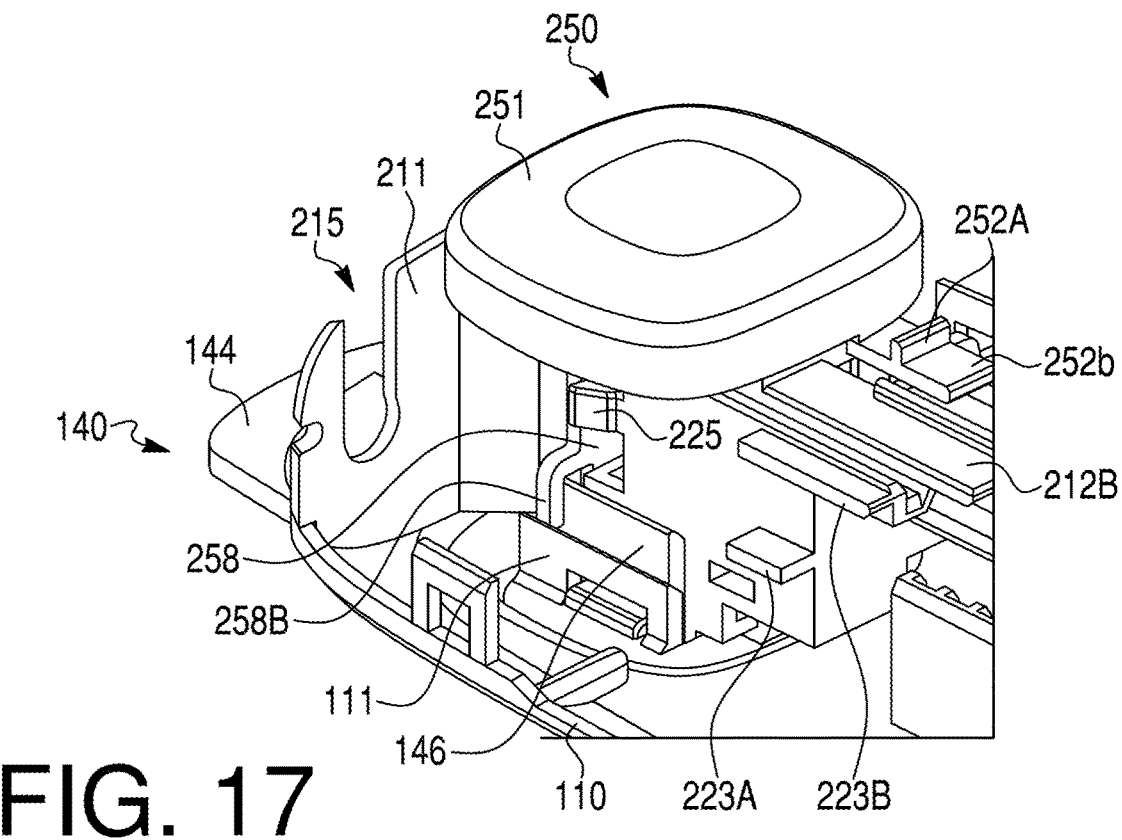
Figure 18:
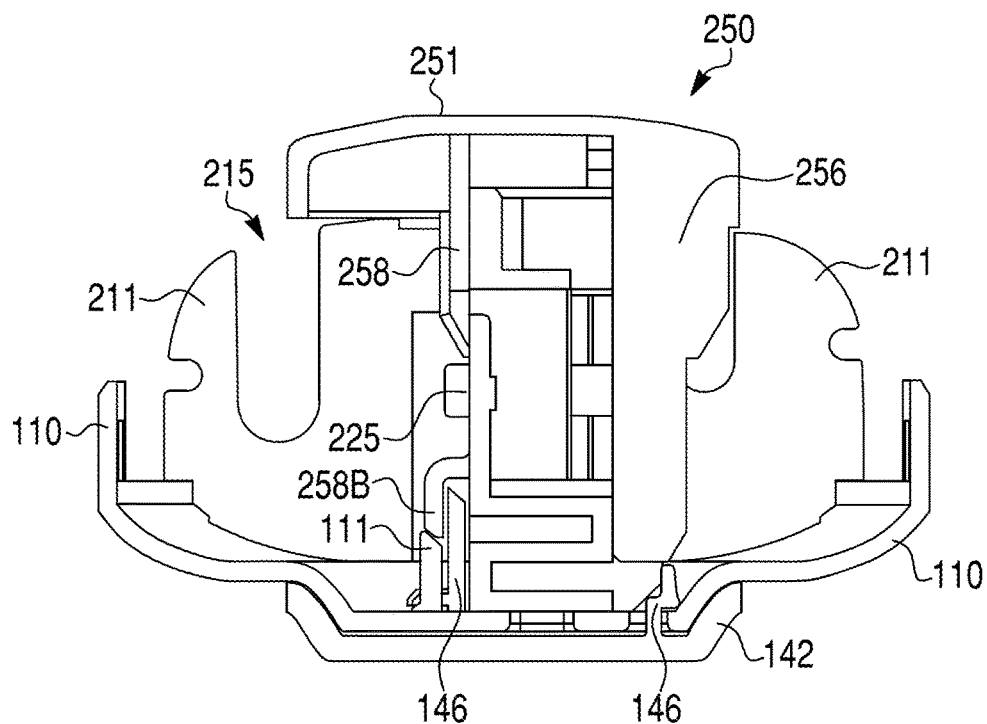
FIG. 18 is a cross-sectional view of the peel tabs of FIGS. 12-13 coupled to the auto-injector of FIG. 1, according to an example of the disclosure.

In other embodiments, as seen in FIGS. 17-18, actuator may include a hook 258B at a bottom end of second leg 258. Hook 258B may be sized, shaped, and configured to engage at least one of the pair of tabs 146. Bottom cover 110 may include a rib 111 extending outwardly (upward) from an inner surface of bottom cover 110. Rib 111 may be positioned in vertical alignment with hook 258B. Peel tab 140 may be configured to inhibit movement of button 250 due to tab 146 forming an impediment obstructing a (downward) travel path of second leg 258.

As seen in FIG. 18, hook 258B may abut against rib 111 in response to applying a downward force onto button 250. A user may remove peel tab 140 from bottom cover 110, thereby removing the impediment against extension 258A by tab 146 and permitting actuation of button 250. Upon removal of peel tab 140, an inclined surface of rib 111 may be configured to flexibly deform hook 258B in a radially inward direction (e.g., toward where tab 146 was previously positioned prior to removal) to facilitate the downward vertical movement of button 250.

Carrier

Figure 19A:
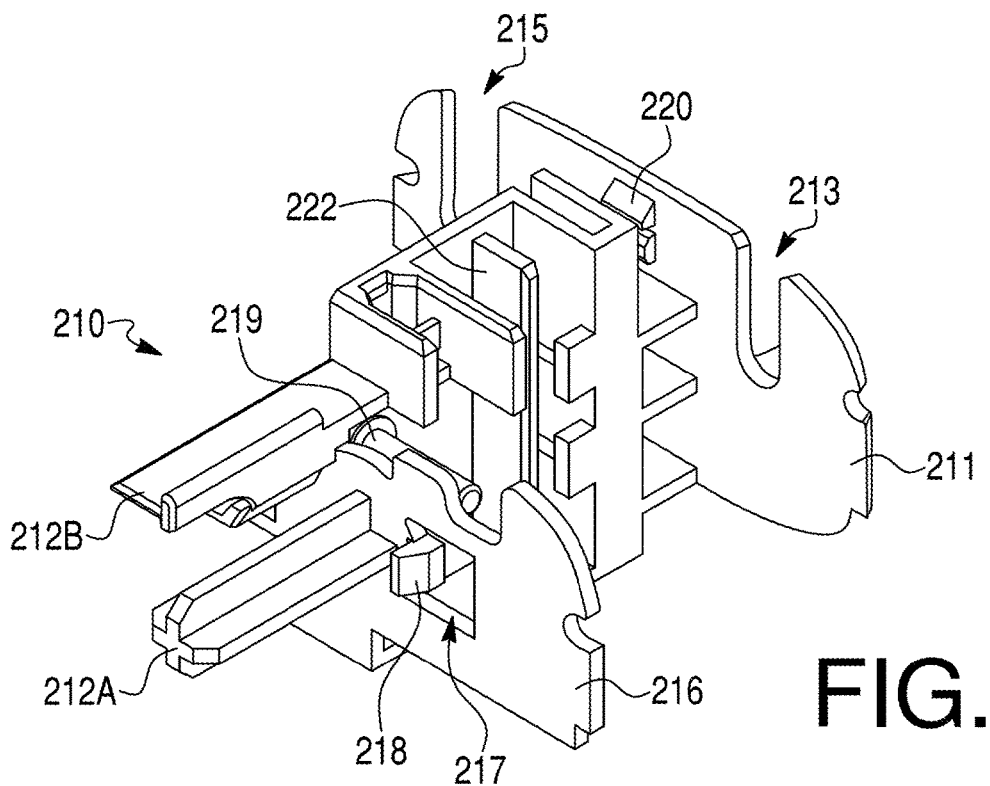
FIGS. 19A, 19B, 20A, and 20B are perspective views of a carrier of the auto-injector of FIG. 1, according to an example of the disclosure.
Figure 19B:
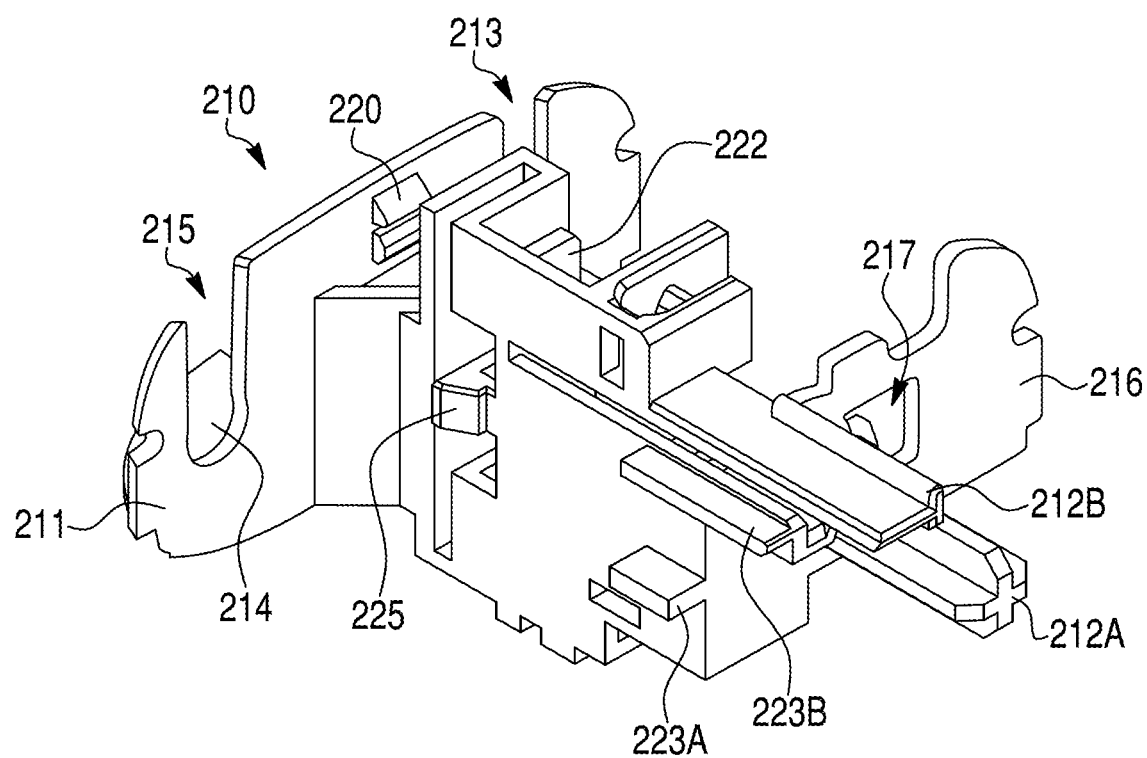

Referring to FIGS. 3 and 19A-19B, carrier 210 may include a first flange 211 and a ledge 214 at a first end of carrier 210, a second flange 216, and a pair of legs 212A, 212B extending away from second flange 216 at a second end of carrier 210 that is opposite of the first end. First flange 211 may extend parallel to transverse axis 14, and ledge 214 may extend parallel to longitudinal axis 10, such that first flange 211 and ledge 214 may be transverse relative to one another. In the embodiment, first flange 211 and ledge 214 may form a 90 degree junction relative to one another. First flange 211 may include a first opening 213 sized and shaped to receive at least a portion of fluid conduit 280, and a second opening 215 sized and shaped to receive at least a portion of sterile connector 290. Openings 213, 215 may allow carrier 210 to receive fluid conduit 280 and sterile connector 290 in a preassembled condition of auto-injector 100.

In the embodiment, and as best seen in FIG. 19A, second flange 216 may include an opening 217 and impediment 218 positioned at least partially within opening 217. Impediment 218 may be configured to engage a component of needle mechanism 200 received within opening 217. Second flange 216 may be configured to receive at least a portion of can actuator 230 (e.g., first leg 234A) through opening 217 when needle mechanism 200 is in an assembled state (see FIG. 4A). As described in detail above, impediment 218 may block the horizontal movement of can actuator 230. A pair of legs 212A, 212B of carrier 210 may extend parallel to longitudinal axis 10. A first leg 212A may be sized and shaped to receive a resilient member 239 (e.g., a spring), such as, for example, about an exterior of first leg 212A. Thus, first leg 212a may be a mandrel that extends through and supports resilient member 239. As described further herein, first leg 212A may be configured to extend into at least a portion of can actuator 230, with resilient member 239 disposed on first leg 212A, when needle mechanism 200 is in an assembled state. Second leg 212B may be sized and shaped to at least partially define a travel path for shuttle actuator 260, along which shuttle actuator 260 may move. Further, second leg 212 may be configured to align shuttle actuator 260 with carrier 210.

Still referring to FIGS. 19A-19B, carrier 210 may further include a post 219 positioned between first flange 211 and second flange 216. Post 219 may be sized and shaped to receive gear 229. Gear 229 may be configured to rotate relative to post 219 in response to movement of one or more features of needle mechanism 200 (e.g., driver 240, shuttle actuator 260). As described in further detail herein, gear 229 may provide selective deployment and retraction of fluid conduit 280 during use of auto-injector 100.

Figure 20A:
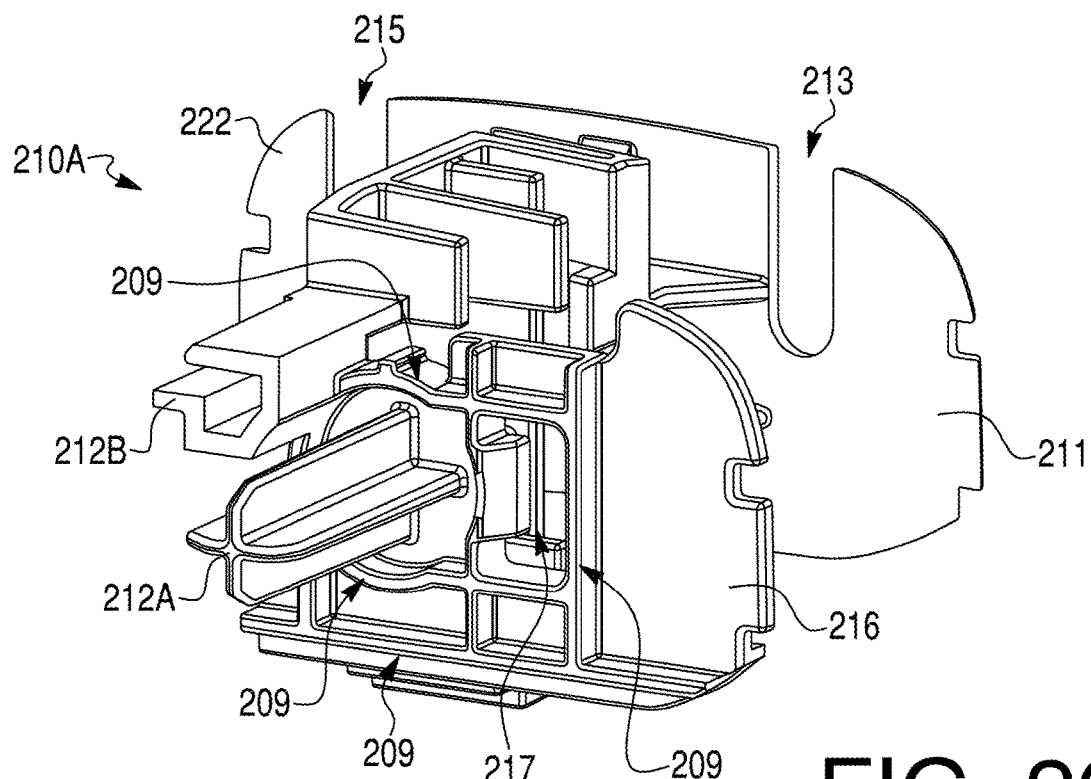
Figure 20B:
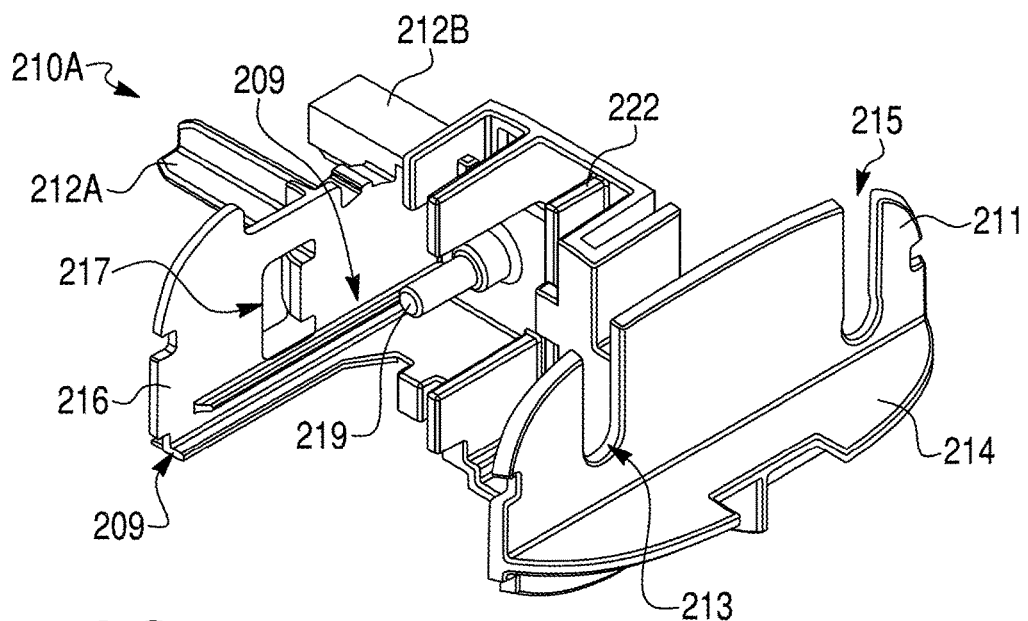

FIGS. 20A-20B depict another carrier 210A that may be substantially similar to carrier 210, such that carrier 210A may be configured and operable similar to carrier 210 shown and described above in FIGS. 19A-19B except for the differences explicitly noted herein. Carrier 210A may include one or more reinforcing ribs 209 along various surfaces and/or features of carrier 210A. In the example, carrier 210A may include at least one reinforcing rib 209 positioned along and/or adjacent to first leg 212A, second flange 216, post 219, etc. In other examples, additional and/or fewer reinforcing ribs 209 may be positioned along other various surfaces and/or features of carrier 210A without departing from a scope of this disclosure.

Each of the one or more reinforcing ribs 209 may be configured to increase a load strength of carrier 210A, and particularly of the surface and/or feature of carrier 210A that the reinforcing rib 209 is positioned on. Accordingly, reinforcing rib 209 may allow the corresponding surface and/or feature to carry a greater structural load (e.g., a spring force, an insertion force, etc.) during use of auto-injector 100. In some embodiments, the one or more reinforcing ribs 209 and/or carrier 210A as a whole may be formed of a partial-glass fill material to further enhance a structural strength of carrier 210A. In further embodiments, the one or more reinforcing ribs 209 may be configured to allow for the ease of moldability of carrier 210A.

Figure 21:
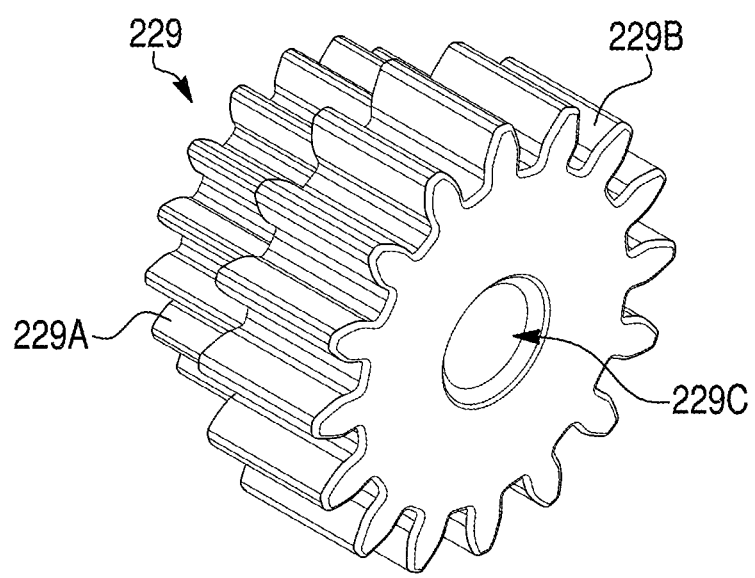
FIG. 21 is a perspective view of a gear of the auto-injector of FIG. 1, according to an example of the disclosure.

As seen in FIG. 21, gear 229 may include a double-spur gear having a first gear portion 229A and a second gear portion 229B, each of which include a plurality of teeth disposed about an outer circumference of the respective gear portion. It should be appreciated that a pitch ratio of the plurality of teeth on each of first gear portion 229A and second gear portion 229B may vary relative to one another. In the embodiment, first gear portion 229A and second gear portion 229B may have a generally circular shape, with first gear portion 229A having a smaller outer diameter than second gear portion 229B, or alternatively first gear portion may have a larger outer diameter than the second gear portion. In this instance, first gear portion 229A may have a first gear ratio that is different (e.g., smaller) than a second gear ratio of second gear portion 229B. First gear portion 229A may abut second gear portion 229B and the two gear portions may rotate about a same axis. It should be appreciated that gear 229 may be configured to mesh and interact with multiple components of needle mechanism 200, such as, for example, at least one component on each of first gear portion 229A (e.g., driver 240) and second gear portion 229B (e.g., shuttle actuator 260). As described in detail above, shuttle actuator 260 and driver 240 may be configured to move different distances relative to one another, during the same rotation of gear 229, due to a difference in size and/or pitch ratio of the two gear portions. Gear 229 may further include an opening 229C for receiving post 219 therethrough.

Figure 27:
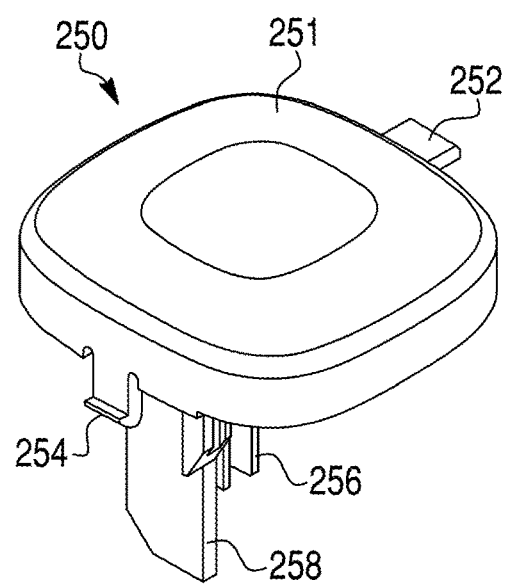
FIGS. 27-29 are perspective views of a button of the auto-injector of FIG. 1, according to an example of the disclosure.

Still referring to FIGS. 19A-19B, carrier 210 may include one or more features (e.g., walls, slots, cavities, platforms, etc.) positioned between first flange 211 and second flange 216 for engaging one or more of driver 240 and button 250. For example, carrier 210 may include a rail 222 that is sized and shaped to mate with a slot of driver 240. Rail 222 may be configured to guide, stabilize, and control movement of driver 240 relative to carrier 210. It is noted that carrier 210 and driver 240 of the present disclosure are not limited to any specific combination of features, such that, for example, driver 240 may include a rail configured to be received within a corresponding slot of carrier 210. Carrier 210 may include a third impediment 220 defined by pair of protrusions with an intermediate gap formed in between. Third impediment 220 may be positioned adjacent to first flange 211, and may be configured to securely couple carrier 210 to button 250 by engaging a fastening mechanism 254 of button 250 (see FIGS. 27-29). For example, fastening mechanism 254 may be received between the pair of protrusions of third impediment 220 (e.g., within the gap defined by the protrusions) when button 250 is in the first (unactuated) position. Fastening mechanism 254 may be removed from the gap when button 250 is moved to the second position, and remain engaged by at least a bottommost protrusion of third impediment 220 to thereby maintain button 250 in the second (actuated) position. In this instance, fastening mechanism 254 may lockout and inhibit further movement of button 250, such as back to the first (unactuated) position. In some embodiments, fastening mechanism 254 may be further configured to balance button 250 relative to carrier 210.

Carrier 210 may further include a pair of ledges 223A, 223B along a sidewall of carrier 210 that are offset from one another by a distance that corresponds to at least a portion of can actuator 230 (e.g., a second leg 234B). Ledges 223A, 22B may be positioned along the sidewall of Carrier 210 including second impediment 225. Accordingly, second impediment 225 may be configured to interface with the portion of can actuator 230 received between ledges 223A, 223B (e.g., second leg 234B).

Can Actuator

Figure 22:
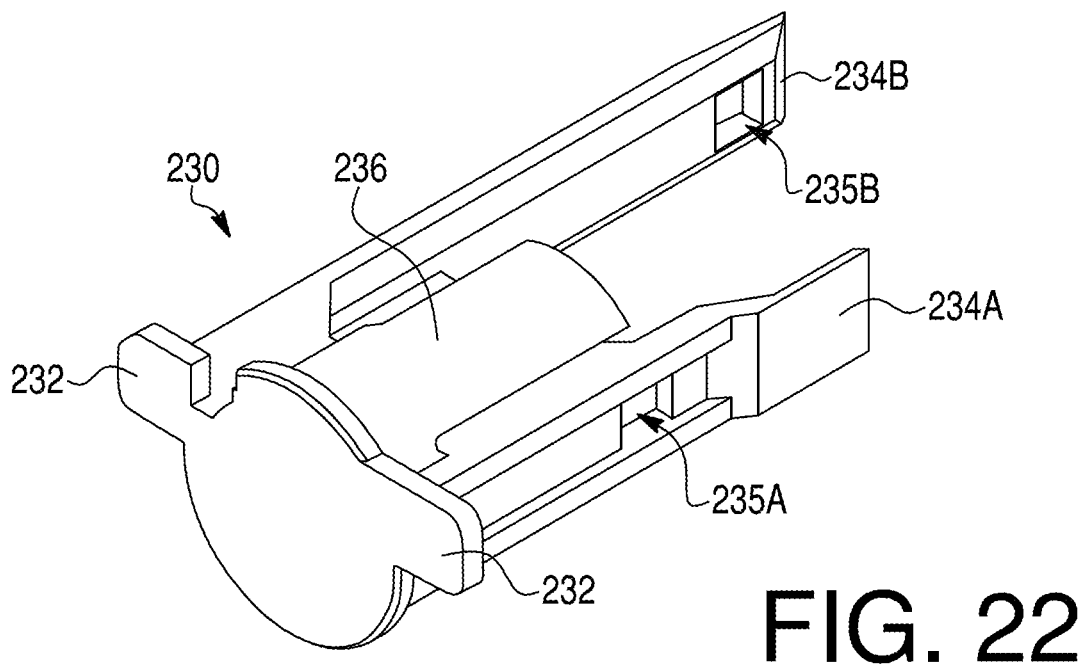
FIGS. 22-23 are perspective views of a can actuator of the auto-injector of FIG. 1, according to an example of the disclosure.
Figure 23:
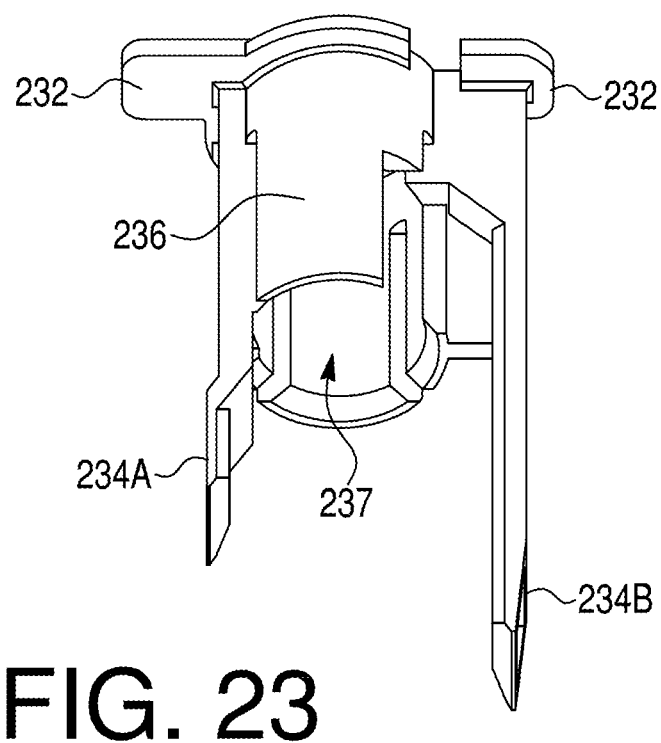

Referring to FIGS. 3 and 22-23, can actuator 230 may include a one or more tabs 232 at a first end of can actuator 230, a pair of legs 234A, 234B at a second, opposite end of can actuator 230, and a central body 236 disposed between the pair of legs 234A, 234B. One or more tabs 232 may be configured to engage at least a portion of shuttle actuator 260 (e.g., stop 267) during use of auto-injector 100 to control movement of shuttle actuator 260 with can actuator 230. In the embodiment, a first leg 234A of can actuator 230 may have a longitudinal length that is relatively less than a second leg 234B. Further, each of the pair of legs 234A, 234B may include an opening 235A, 235B, respectively, that is configured to engage a corresponding impediment (e.g., first impediment 218, second impediment 225) of carrier 210 when needle mechanism 200 is in an assembled state prior to actuation.

For example, as best seen in FIG. 22, first leg 234A may include a first opening 235A and second leg 234B may include a second opening 235B. As shown and described in further detail herein, first leg 234A may be configured to receive first impediment 218 within first opening 235A (see FIG. 5), and second leg 234B may be configured to receive second impediment 225 within second opening 235B (see FIG. 6) when can actuator 230 is coupled to carrier 210. Further, a first end of each of the pair of legs 234A, 234B may be configured to engage at least a portion of button 250, thereby securing button 250 to can actuator 230. In the embodiment, first leg 234A may include a radial bend along the longitudinal length of first leg 234A, such as, for example, adjacent to first opening 235A, while second leg 234B may include a substantially linear profile. It should be appreciated that legs 234A, 234B may include various other suitable shapes, sizes, and/or configurations than those shown and described herein without departing from a scope of this disclosure.

Further, as shown in FIG. 7, can actuator 230 may include an opening 237 at an end of central body 236 for receiving resilient member 239 (FIG. 3). In the embodiment, central body 236 may have a generally cylindrical shape, and opening 237 may provide access into a lumen of central body 236. Central body 236 may be disposed between the pair of legs 234A, 234B, and have a longitudinal length that is defined between tabs 232 and a location of first opening 235A along first leg 234A. In other embodiments, opening 237 may include a post extending through can actuator 230, to facilitate alignment and/or support of resilient member 239 when received within can actuator 230. In further embodiments, opening 237 and a lumen of central body 236 may be sized and shaped to form a close fit connection with resilient member 239, thereby supporting resilient member 239 and inhibiting occurrences of resilient member 239 bending within the lumen of central body 236.

Central body 236 may be sized and shaped to receive resilient member 239 and first leg 212A. Resilient member 239 may be compressed in a longitudinal direction parallel to longitudinal axis 10 (FIG. 3) between central body 236 and second flange 216 (see FIGS. 7-8) when needle mechanism 200 is in an assembled state. As described in detail herein, resilient member 239 may be movable from an energy-storing state (e.g., compressed configuration) with can actuator 230 positioned at a first location (see FIG. 7), to an energy-released state (e.g., expanded configuration) with can actuator 230 positioned at a second location that is different than the first location (see FIG. 8). Stated differently, resilient member 239 may be configured to apply a force onto central body 236 and against second flange 216, thereby causing can actuator 230 to move relative to carrier 210.

Driver

Figure 24:
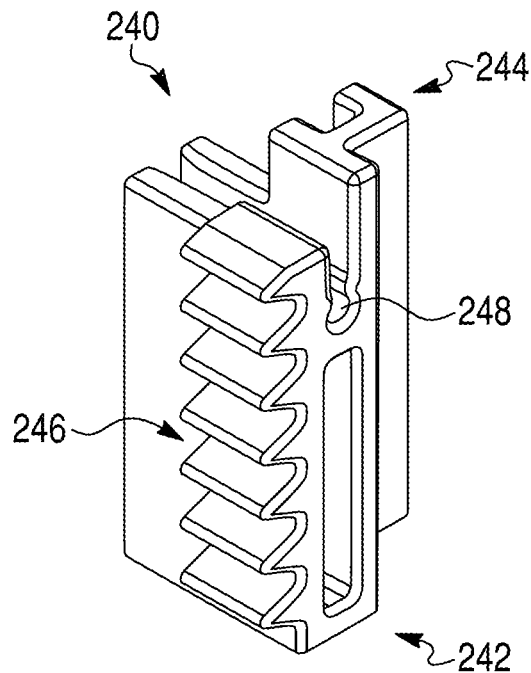
FIGS. 24-26 are perspective views of a driver of the auto-injector of FIG. 1, according to an example of the disclosure.
Figure 25:
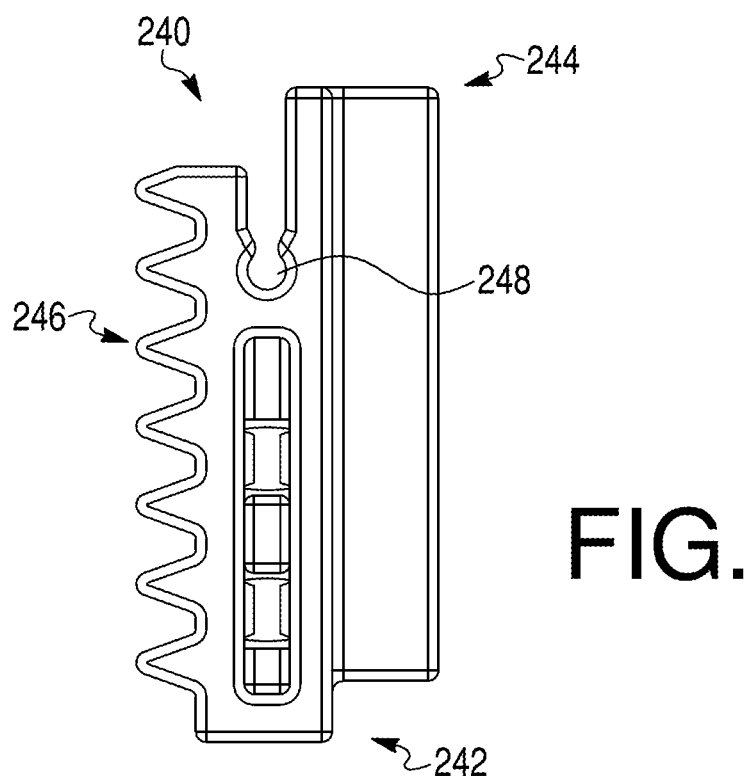
Figure 26:
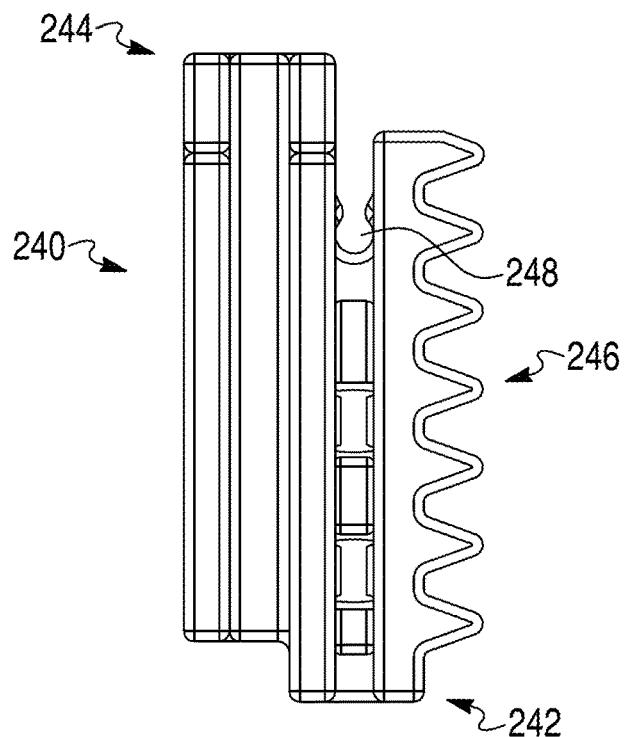

Referring now to FIGS. 24-26, driver 240 may include a first (bottom) end 242 and a second (top) end 244 defining a longitudinal length of driver 240. Driver 240 may further include a rack 246 positioned along at least a portion of one of the sidewalls of driver 240. Rack 246 may include a plurality of teeth, and may extend along a substantial portion of the longitudinal length of driver 240 between first end 242 and second end 244. Rack 246 may be configured to engage and mesh with corresponding teeth of gear 229 (FIG. 3). Driver 240 may further include one or more slots disposed through a body of driver 240, such as slot 248 that is sized and shaped to receive a portion of fluid conduit 280. Accordingly, fluid conduit 280 may be coupled to driver 240 at slot 248 such that movement of driver 240 relative to auto-injector 100 (e.g., vertical translation) may provide for a corresponding movement of fluid conduit 280.

Button

Referring to FIGS. 3 and 27-29, button 250 may be a depressible button having a body 251, a stop tab 252 (e.g., an impediment), a fastening mechanism 254, a first leg 256, and a second leg 258. Body 251 may include a top surface defining a contact interface for actuating button 250. Stop tab 252 may extend outwardly from a first side of body 251, and fastening mechanism 254 may extend outwardly from a second, opposite side of body 251.

Stop tab 252 may include one or more ridges and/or protrusions extending outwardly therefrom. The one or more ridges of stop tab 252 may abut against at least a portion of shuttle actuator 260 to inhibit movement of shuttle actuator 260 relative to carrier 210 prior to actuation of button 250 (see FIG. 31). The one or more protrusions of stop tab 252 may block or otherwise impede movement of indicator slide 270 (see FIG. 4A). As briefly described above, and as seen in FIGS. 3 and 5-6, stop tab 252 may include protrusion 252a extending outwardly from a body of stop tab 252 and ridge 252b defining a terminal end of stop tab 252 opposite of body 251. In other embodiments, stop tab 252 may include additional and/or fewer ridges and/or protrusions along various other sides of stop tab 252. For example, protrusion 252a may be omitted from stop tab 252 and top cover 118 may include stop tab 119 as seen in FIG. 4B. Fastening mechanism 254 may include a flexible hook or clasp for engaging third impediment 220. As described in detail above, fastening mechanism 254 may position button 250 at the first position relative to carrier 210 prior to actuation of button 250, and maintain button 250 at the second position after actuation of button 250.

Figure 28:
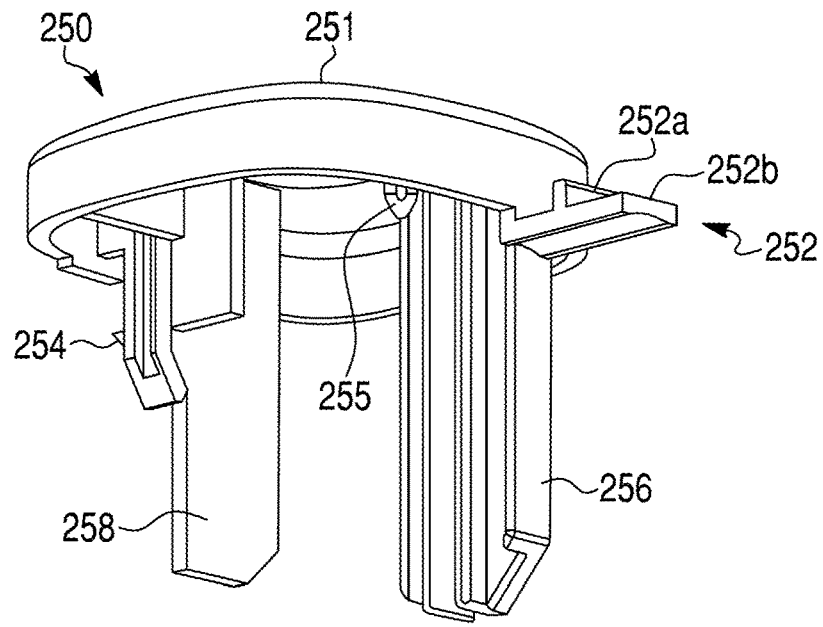
Figure 29:
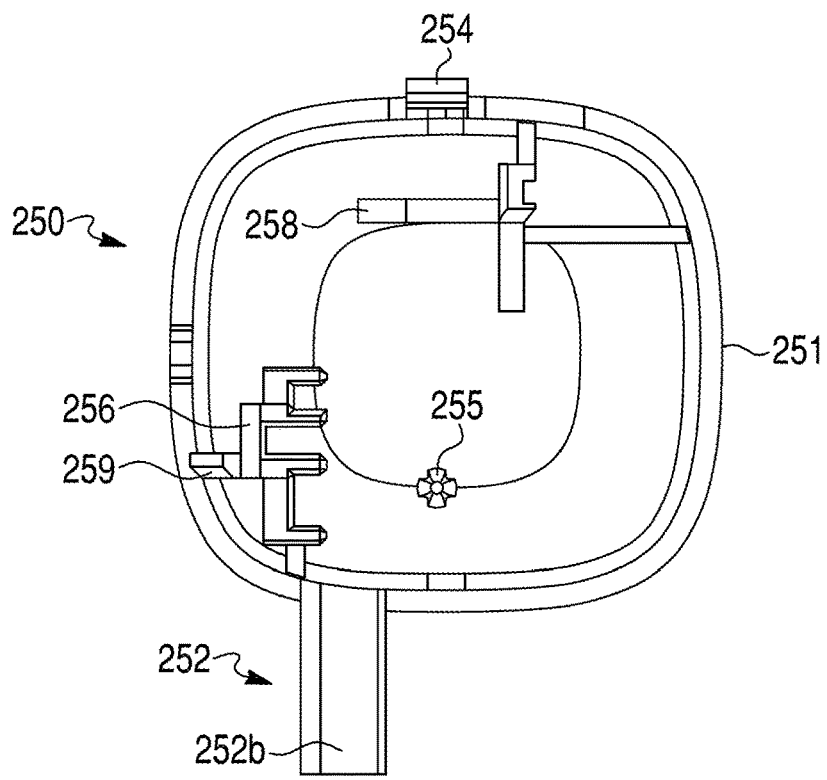

As best seen in FIG. 28, button 250 may include a protrusion 255 along a bottom surface of body 251. Protrusion 255 may be configured to engage a resilient member 249 (e.g., a spring) disposed within carrier 210. Resilient member 249 may apply a resistive force against button 250 to generate a tactile feedback against body 251 when a user actuates button 250. In other embodiments, resilient member 249 may be omitted entirely such that button 250 may exclude protrusion 255. First leg 256 may extend outwardly (e.g., downwardly) from body 251 and have a longitudinal length that is greater than second leg 258. As described in detail above, first leg 256 may be configured to engage at least a portion of can actuator 260 (e.g., first leg 234A) when needle mechanism 200 is in an assembled state and prior to actuation of button 250. Button 250 may further include a ramp 259 positioned along an exterior surface of first leg 256, which may be configured to decouple first leg 234A from carrier 210 upon actuation of button 250.

As seen in FIGS. 4A and 5, ramp 259 may extend outward (e.g., downwardly) from body 251 and may be positioned along first leg 256 such that a sloped surface of ramp 259 is located adjacent to first leg 234A prior to actuation of button 250. As described above, ramp 259 may be configured to move first leg 234A relative to carrier 210 to decouple can actuator 230 from carrier 210 (e.g., by disengaging impediment 218 from first opening 235A). It should be appreciated that ramp 259 may move in response to actuation of button 250 when a user applies a downward force onto body 251. Referring back to FIG. 29, second leg 258 may extend outwardly (e.g., downward) from body 251 along a side of button 250 adjacent to fastening mechanism 254. Second leg 258 may be configured to engage at least a portion of can actuator 260 (e.g., second leg 234B) when needle mechanism 200 is in an assembled state and prior to actuation (FIG. 6).

Shuttle Actuator

Referring to FIGS. 3 and 30-32, shuttle actuator 260 may include a longitudinal body defined between a first end 262 and a second end 264. The longitudinal body of shuttle actuator 260 may be generally cylindrical, and sized to at least partially receive container 370. In some embodiments, shuttle actuator 260 may have an irregularly-shaped body, such as semi-circular (e.g., C-shaped). In this instance, at least a portion of container 370 may be exposed from underneath shuttle actuator 260 when received between first end 262 and second end 264 (e.g., to facilitate visualization of container 370 from underneath shuttle actuator 360 through a housing of auto-injector 100). As described further herein, shuttle actuator 260 may be coupled to container 370, with first end 262 sized and shaped to receive first end 372, and second end 264 sized and shaped to receive second end 374. Shuttle actuator 260 may be shorter, equal to, or longer than container 370. With shuttle actuator 260 coupled to container 370, it should be appreciated that shuttle actuator 260 and container 370 may be configured to move together and/or simultaneously within the housing of auto-injector 100 during use.

Figure 30:
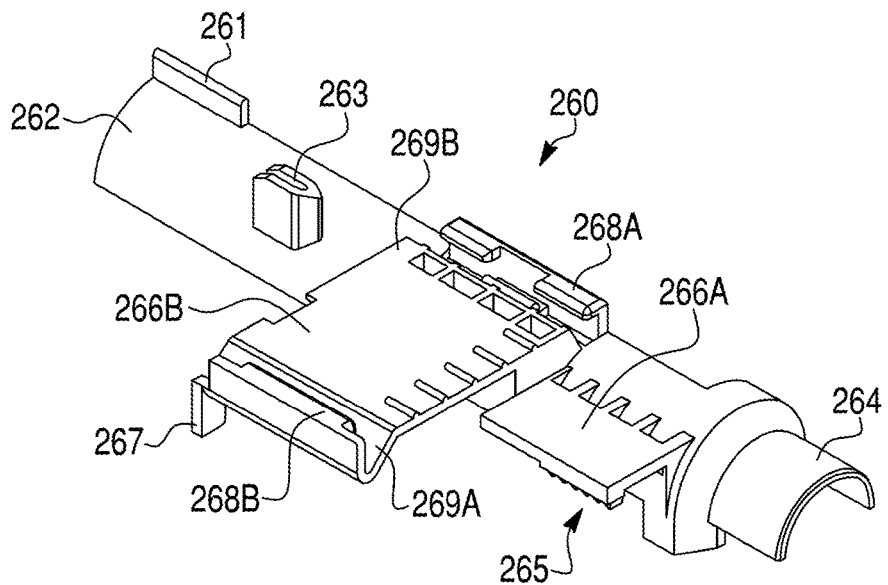
FIGS. 30-32 are perspective views of a shuttle actuator and indicator slide of the auto-injector of FIG. 1, according to an example of the disclosure.

As best seen in FIG. 30, shuttle actuator 260 may include a first platform 266A and a second platform 266B. First platform 266A may be positioned adjacent to second end 264 relative to second platform 266B, and may include a rack 265 disposed along a bottom surface of first platform 266A. As described in further detail herein, movement of shuttle actuator 260 may be at least partially driven by movement of can actuator 230 (from expansion of resilient member 239) and pressurized fluid released from fluid source 350. Further, first platform 266A may at least partially define a travel path of indicator slide 270 along shuttle actuator 260. Second platform 266B may be positioned adjacent to first end 262 relative to first platform 266A, and may include one or more rails for maintaining indicator slide 270 on shuttle actuator 260. Second platform 266B may further serve as an indicator by providing a graphical interface to facilitate visualization of a position of shuttle actuator 260 to a user, which may be indicative of a state of auto-injector 100 during use.

In the embodiment, second platform 266B may include a first rail 268A and a second rail 268B extending along or parallel to longitudinal axis 10 (see FIG. 3). First rail 268A and second rail 268B may be positioned along opposing sides of second platform 266B, such that rails 268A, 268B may define a width of platform 266B. It should be appreciated that the width of platform 266B may correspond to a size of indicator slide 270. Each of rails 268A, 268B may include a protrusion and/or overhang portion that is configured to at least partially extend over indicator slide 270 for maintaining indicator slide 270 on second platform 266B during use of auto-injector 100.

Still referring to FIG. 30, shuttle actuator 260 may include a recessed channel 269A along second platform 266B. Recessed channel 269A may be positioned adjacent to second rail 268B, and may extend along or parallel to longitudinal axis 10 (see FIG. 3). Recessed channel 269A may be sized and shaped to receive at least a portion of indicator slide 270 (e.g., a first edge 276). Recessed channel 269A may be configured to maintain indicator slide 270 on second platform 266B during use of auto-injector 100.

Figure 31:
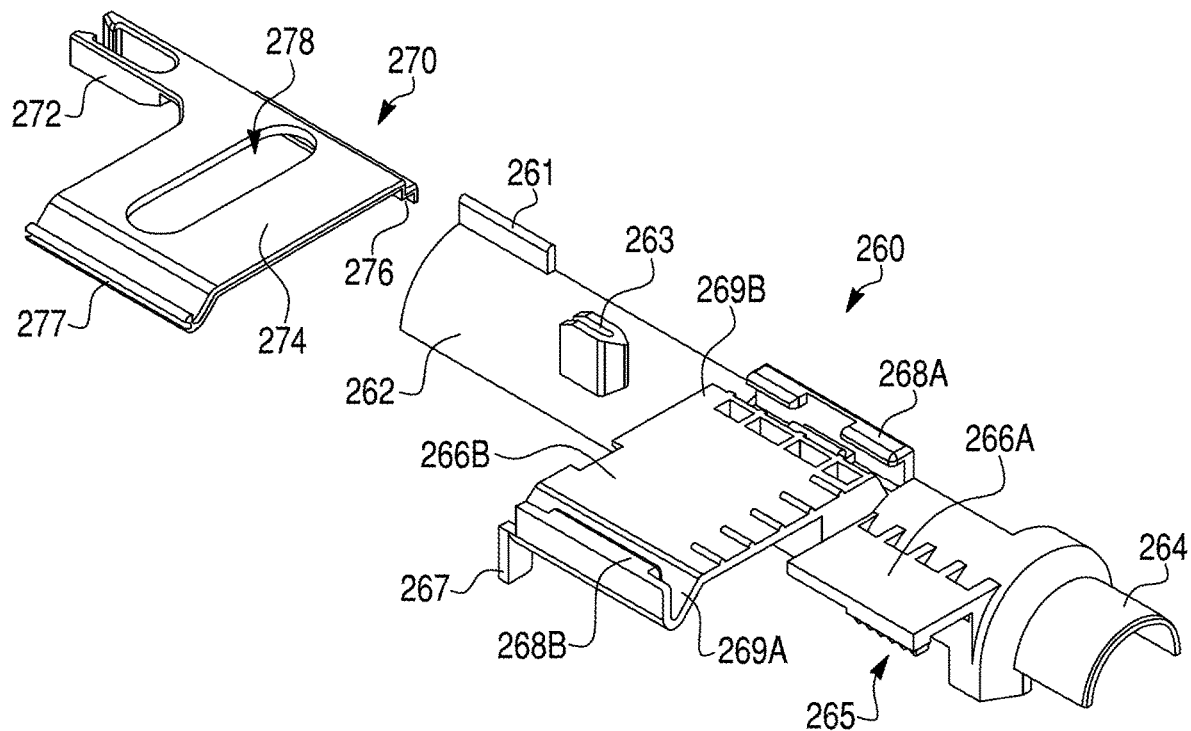

Referring now to FIG. 31, shuttle actuator 260 may further include a projection 261 and a fastening mechanism 263 positioned adjacent to first end 262. Projection 261 may be sized and shaped to extend outwardly (e.g., upward) from the longitudinal body of shuttle actuator 260, and positioned in alignment with first rail 268A. Projection 261 may be configured to facilitate receipt of indicator slide 270 onto shuttle actuator 260, and alignment of indicator slide 270 with second platform 266B. In the embodiment, indicator slide 270 may include a body 274 with a first edge 276 along a sidewall of body 274. First edge 276 may be sized and shaped to be received through first rail 268A, and projection 261 may align first edge 276 with first rail 268A upon receipt of indicator slide 270 onto shuttle actuator 260. Indicator slide 270 may further include a second edge 277 positioned along an opposing sidewall of body 274 from first edge 266. Second edge 277 may be sized and shaped to slide beneath second rail 268B. In the embodiment, second edge 277 may be angled relative to body 274 such that second edge 277 extends along a different plane than first edge 276.

Figure 32:
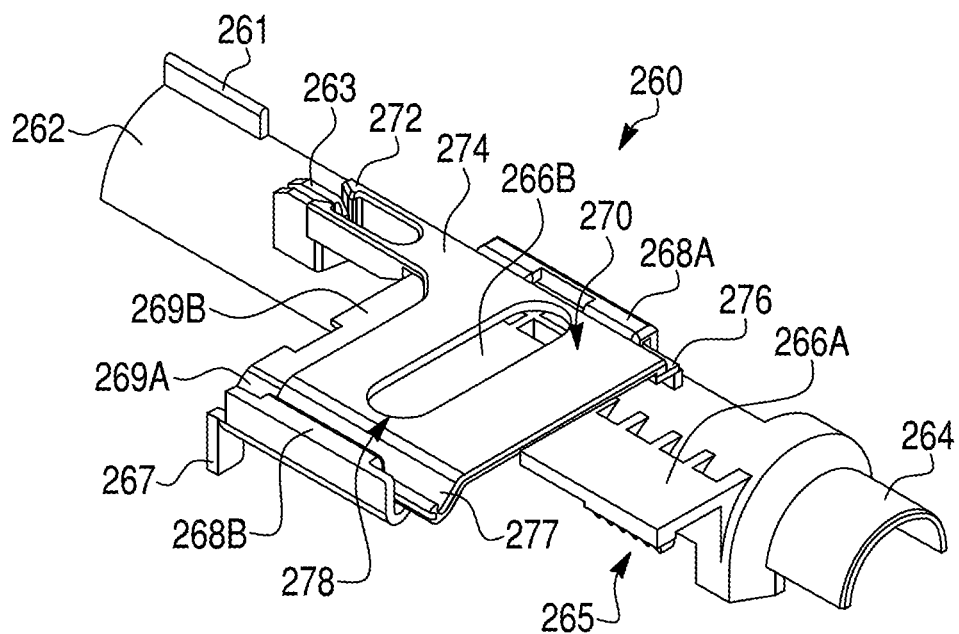

As best seen in FIG. 32, second edge 277 may be received within recessed channel 269A when indicator slide 270 is coupled to shuttle actuator 260. Fastening mechanism 263 may be configured to engage a leg 272 of indicator slide 270 to couple body 274 to shuttle actuator 260. Accordingly, the pair of rails 268A, 268B and fastening mechanism 263 may collectively maintain indicator slide 270 on shuttle actuator 260 during use of auto-injector 100. In some embodiments, indicator slide 270 may further include a shelf 269B positioned adjacent to rail 268A and defining a first edge of second platform 266B. Shelf 269B may be configured to engage at least a portion of indicator slide 270 (e.g., a bottom surface of body 274) to further couple indicator slide 270 to shuttle actuator 260, particularly during assembly of auto-injector 100. Shelf 269B, in conjunction with fastening mechanism 263, may be collectively configured to fix indicator slide 270 relative to shuttle actuator 260 upon receipt. Indicator slide 270 may further include a window 278 positioned within body 274. Window 278 may facilitate visualization of a secondary indicator positioned beneath body 274, such as, for example, a surface of second platform 266B. As described in detail above, second platform 266B may serve as an indicator by providing a graphical interface. Accordingly, window 278 may facilitate visualization of second platform 266B through indicator slide 270. Shuttle actuator 260 may further include a stop 267 extending outwardly (e.g., downward) from second platform 266B in a direction parallel to transverse axis 14 (see FIG. 3). As described in detail herein, stop 267 may be configured to engage at least a portion of can actuator 230 (e.g., tab 232) to form an impediment obstructing movement of can actuator 230 relative to shuttle actuator 260 (see FIGS. 9-10).

Fluid Conduit

Figure 33:
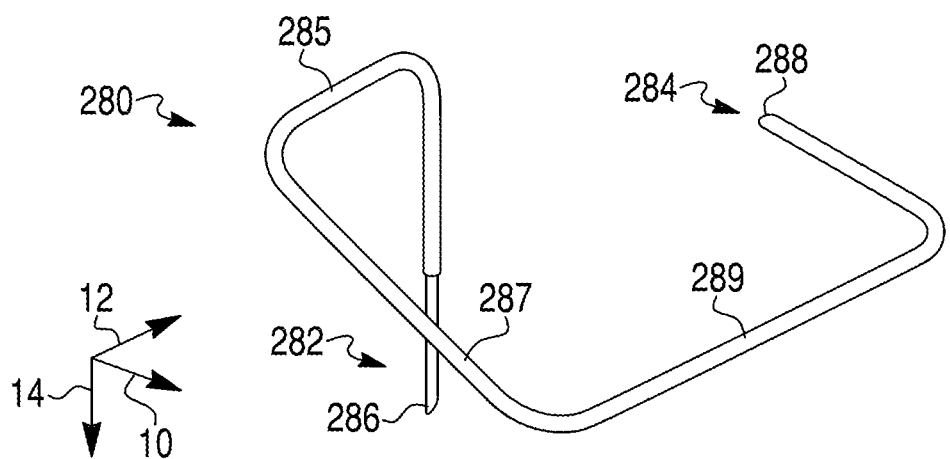
FIG. 33 is a perspective view of a fluid conduit of the auto-injector of FIG. 1, according to an example of the disclosure.

Referring to FIG. 33, fluid conduit 280 may be substantially similar to the fluid conduit described in International PCT Application No. PCT/US2020/040729, published as WO 2021/003409, which is incorporated by reference. In the embodiment, fluid conduit 280 may extend from a first end 282 to a second end 284. First end 282 may include a (first) needle 286 that is configured to be injected into a user. Needle 286 may include a sharp and/or beveled tip, and may extend generally along or parallel to transverse axis 14. Second end 284 may include (second) needle 288 (described previously with respect to FIGS. 2A-2C) that is substantially similar to needle 286, but may be positioned within auto-injector 100 to penetrate container 370 to access medicament 20 to be injected into the user. Fluid conduit 280 may include an intermediate section with a first segment 285 extending along or parallel to lateral axis 12, a second segment 287 extending along or parallel to longitudinal axis 10, and a third segment 289 extending along or parallel to lateral axis 12. First segment 285 and third segment 289 may be joined to one another by second segment 287.

Fluid conduit 280 may be flexibly deformable along one or more of the ends 282, 284 and/or segments 285, 287, 289 of the intermediate section. In this instance, fluid conduit 280 may flex and/or move, such as, for example, when deploying or retracting needle 286 relative to a user, respectively. In some embodiments, fluid conduit 280 may include a coil (not shown) that may facilitate flexion of fluid conduit 280 and movement of needle 286 along transverse axis 14 during deployment and retraction relative to the user. It should be appreciated that any suitable shape for the coil may be included, e.g., a serpentine, curved, or other shape that enables flexion of fluid conduit 280. The coil, or similar structure, may act as a cantilever when needle 286 is deployed and/or retracted.

In some examples, fluid conduit 280 may include only metal or a metal alloy. In other examples, fluid conduit 280 may be include any other suitable material, such as, e.g., polymers or the like. Needle 288 and the intermediate sections may define a 22 or 23 Gauge, thin-walled needle, while needle 286 may be a 27 Gauge needle. In other words, fluid conduit 280 may have a varying needle gauge across its length, and in particular, needle 286 and needle 288 may have different needle gauges. Other needle sizes ranging from, e.g., 6 Gauge to 34 Gauge, also may be utilized as appropriate. Fluid conduit 280 may reduce the amount of material that contacts the drugs, reduce joints and assembly steps, and require less sterilization than conventional devices.

Figure 34:
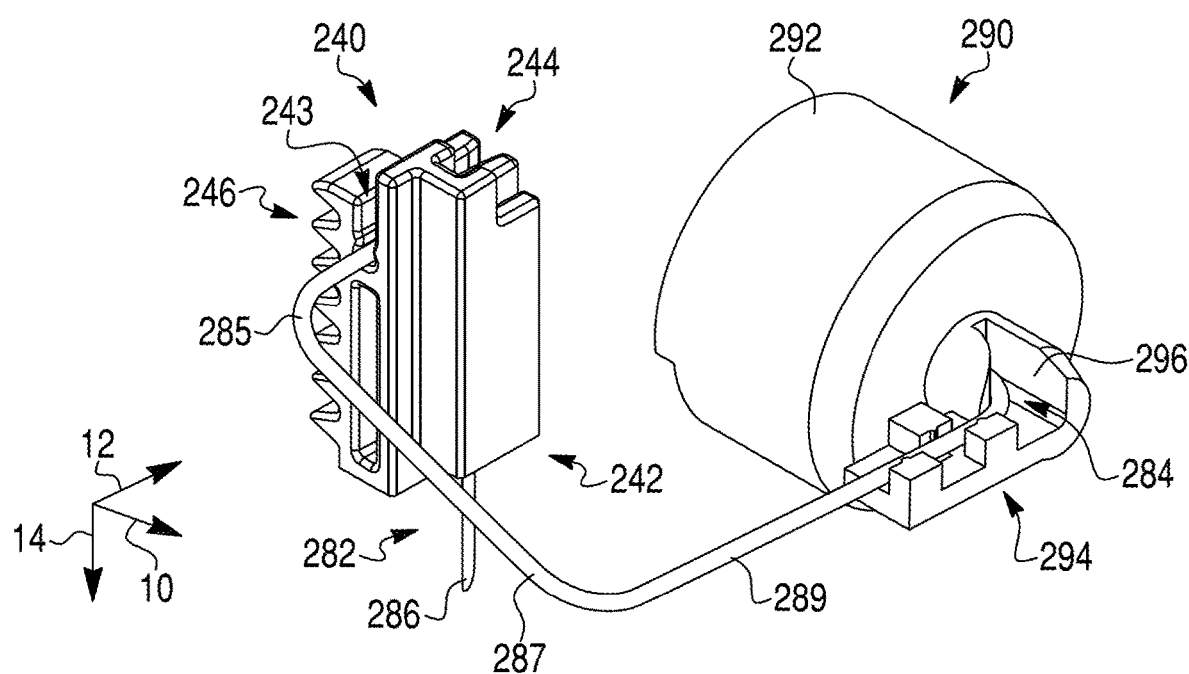
FIG. 34 is a perspective view of the fluid conduit of FIG. 33 and driver of FIGS. 30-32 assembled to a sterile connector, according to an example of the disclosure.

Referring now to FIG. 34, fluid conduit 280 may be coupled to driver 240 along first segment 285. In the embodiment, first segment 285 may be received within slot 248 and coupled to driver 240. Accordingly, first end 282, needle 286, and first segment 285 may be configured to move in response to movement of driver 240 relative to auto-injector 100. It should be appreciated that one or more other intermediate segments of fluid conduit 280 (e.g., second segment 287, third segment 289) may be configured to flex, deform, and/or more to accommodate movement of first end 282, needle 286, and first segment 285. Needle 286 may extend outward from driver 240, and positioned adjacent to first (bottom) end 242.

Fluid conduit 280 may be further coupled to sterile connector 290 along second end 284. In the embodiment, second end 284 may extend through an opening 296 of sterile connector 290 and needle 288 may be disposed within body 292. At least a portion of third segment 289 may be received along seat 294, thereby fixing fluid conduit 280 to sterile connector 290. Once needle 308 penetrates and establishes fluid communication with container 370, in response to container 370 moving relative to (e.g., toward) needle 288 and sterile connector 290 (see FIG. 2B), a medicament may travel from container 370, through needle 308, the intermediate segments 285, 287, 289, and needle 306 (pierced through the user's skin), and into the user. As best seen in FIG. 6, sterile connector 290 may include a rail 291 disposed within body 292 to facilitate an alignment and receipt of container 370. In some embodiments, sterile connector 290 may be configured to move (e.g., rotate) to facilitate movement of fluid conduit 280 within auto-injector 100. In this instance, deformation and/or deflection of fluid conduit 280 may be minimized.

Figure 35:
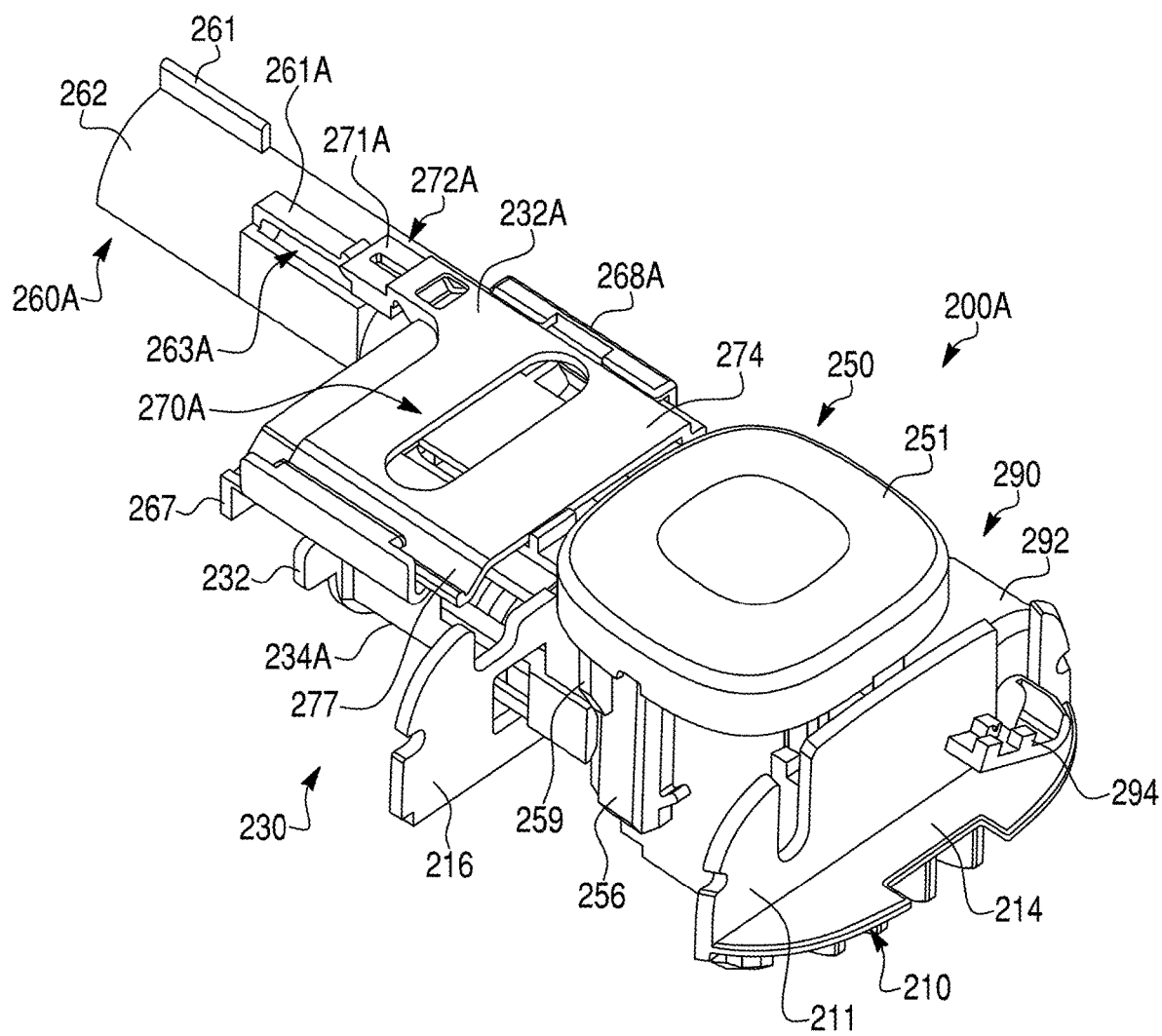
FIGS. 35-36 are partial perspective views of another exemplary needle mechanism of the auto-injector of FIG. 1, according to an example of the disclosure.

Referring now to FIG. 35, another implementation of a needle mechanism is depicted. Needle mechanism 200A may be configured and operable similar to needle mechanism 200 shown and described above except for the differences explicitly noted herein. Accordingly, like reference numerals are used to identify like components. In the embodiment, needle mechanism 200A may include a shuttle actuator 260A and an indicator slide 270A. Shuttle actuator 260A may include a fastening mechanism 263A positioned adjacent to first end 262, and configured to engage a leg 272A of indicator slide 270A to couple body 274 to shuttle actuator 260A. Fastening mechanism 263A may include a flexible tab 261A with a protrusion 262A positioned along an end of the flexible tab 261A.

Figure 36:
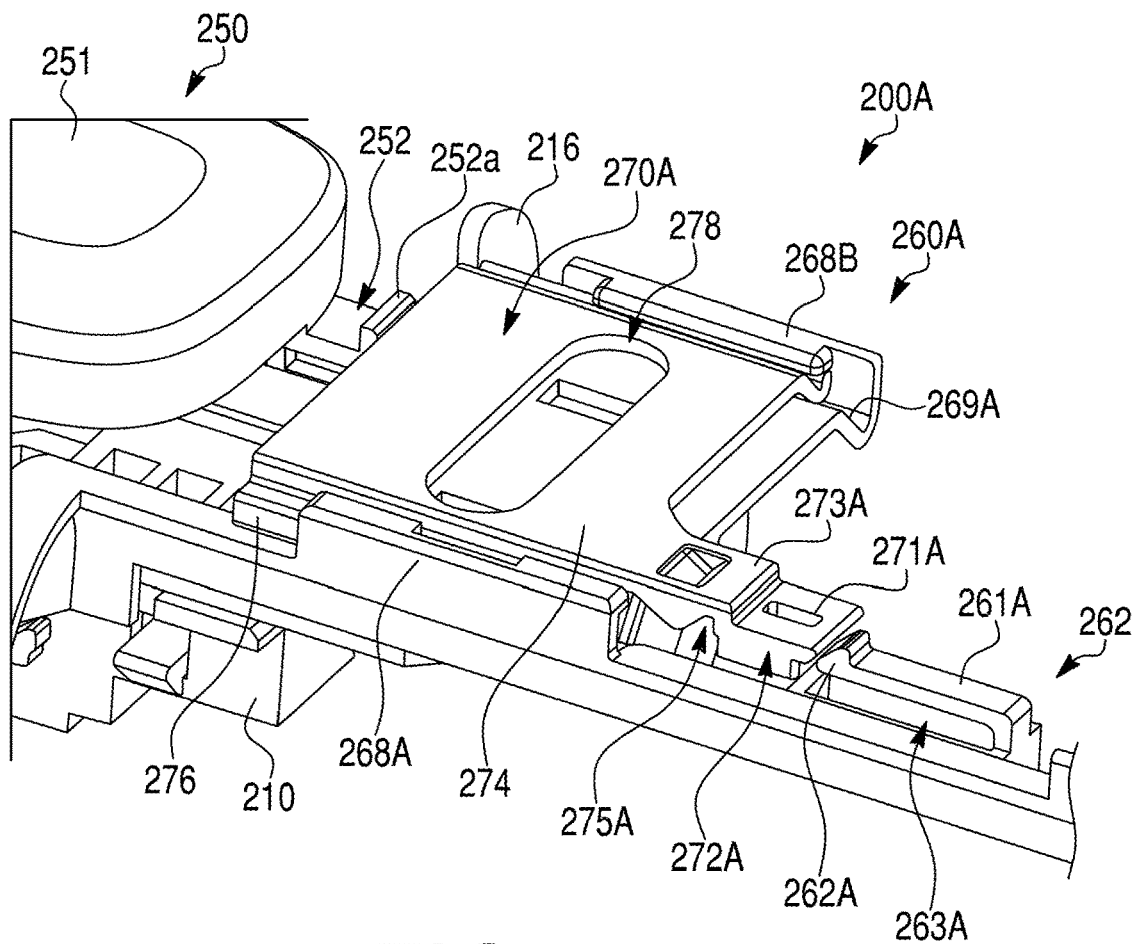
Figure 37:
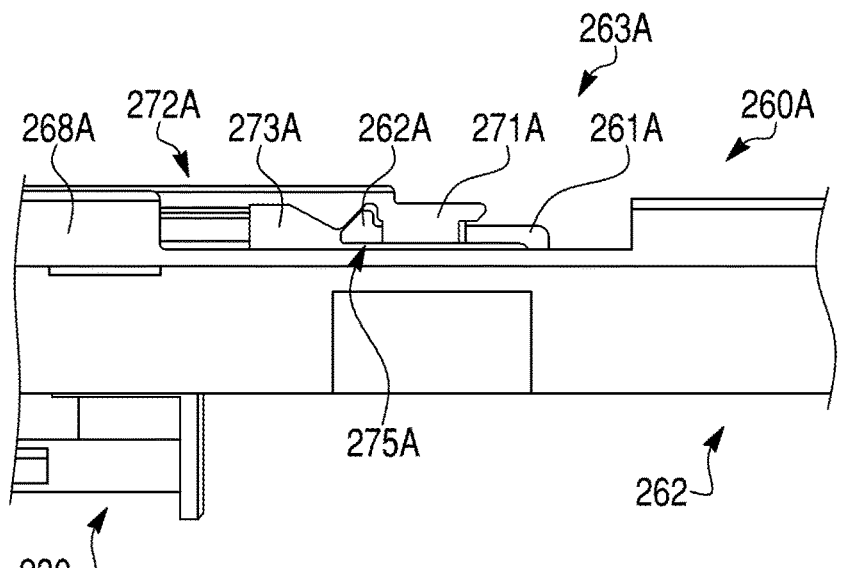
FIG. 37 is a partial side view of the needle mechanism of FIGS. 35-36, according to an example of the disclosure.

Leg 272A may include a first snap 271A and a second snap 273A, with first snap 271A being positioned away from second snap 273A. Further, first snap 271A may be positioned along a plane that is relatively lower than second snap 273A, which is positioned along a plane that is similar to body 274. As best seen in FIGS. 36-37, leg 272A may include a recess 275A defined between first snap 271A and second snap 273A that is sized and shaped to receive protrusion 262A. Accordingly, indicator slide 270A may be configured to couple with shuttle actuator 260A upon receiving protrusion 262A within recess 275A.

Figure 38:
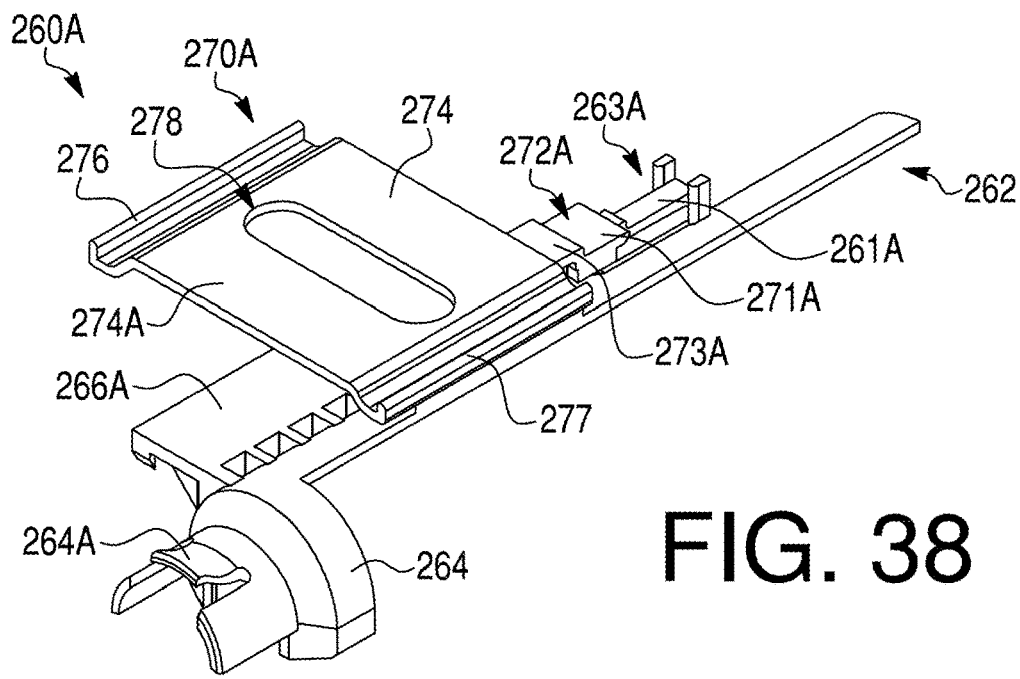
FIG. 38 is a perspective view of a shuttle actuator of the needle mechanism of FIGS. 35-36, according to an example of the disclosure.

Referring now to FIG. 38, indicator slide 270A may further include a graphical interface 274A positioned along at least a portion of body 274 for providing a user with information of a position of indicator slide 270A relative to shuttle actuator 260A, which may be indicative of a state of auto-injector 100 during use. Graphical interface 274A may be visible through a housing of auto-injector 100, such as, for example, via a transparent window along one or more of top cover or bottom cover 110. Graphical interface 274A may include various suitable formats, including, but not limited to, a color, a text, an image, and more. Shuttle actuator 260A may further include a snap connector 264A at second end 264 for coupling shuttle actuator 260A to sterile connector 290. Snap connector 264A may be flexibly deformable in response to receiving an application of force thereto, such as, for example, from protrusion 253A when button 250 is pressed downward.

Figure 39A:
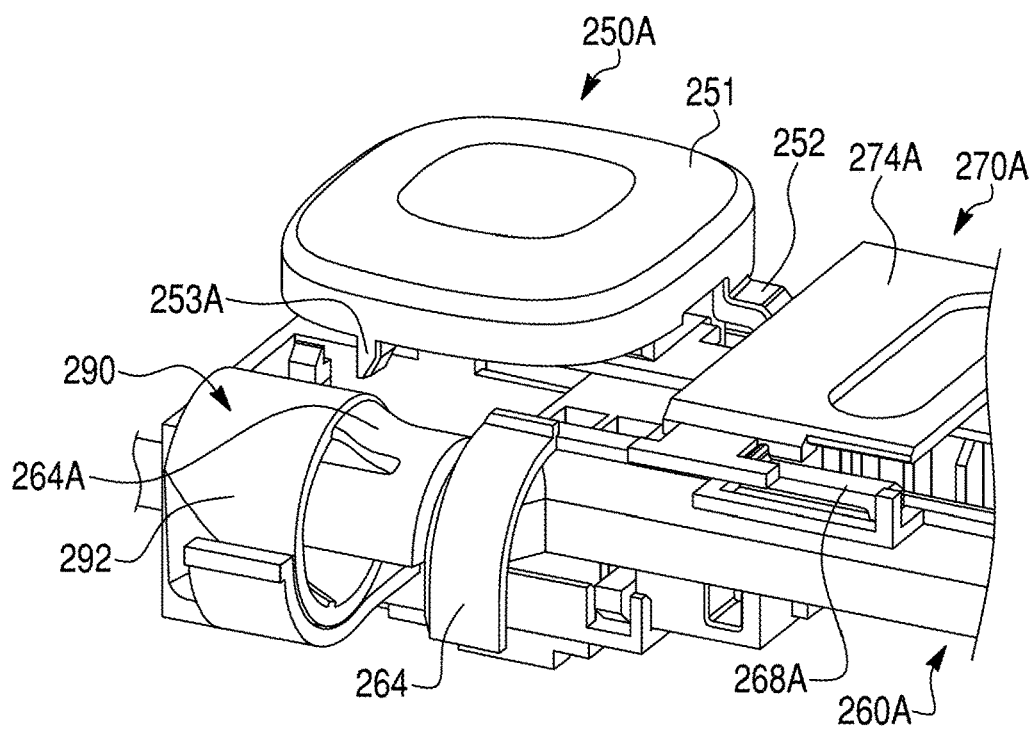
FIGS. 39A-39C are partial perspective views of the needle mechanism of FIGS. 35-36, according to an example of the disclosure.

For example, as seen in FIG. 39A, with shuttle actuator 260A in the first state, first end 264 may be positioned adjacent to sterile connector 290 such that snap connector 264A may abut against body 292. In this instance, shuttle actuator 260A may be locked out from coupling with sterile connector 290 via the interface between snap connector 264A and an outer edge of body 292. Button 250A may include a protrusion 253A extending outwardly (e.g., downward) from body 251, and aligned with snap connector 264A. In response to depressing button 250A, protrusion 253A may move and contact snap connector 264A, thereby applying a downward force onto snap connector 264A, thereby permitting shuttle actuator 260A to move from the first state to the second state. In this state, a first indicator (e.g., graphical interface 274A) may be visible from outside of auto-injector 100 through a window on the housing of auto-injector 100.

Figure 39B:
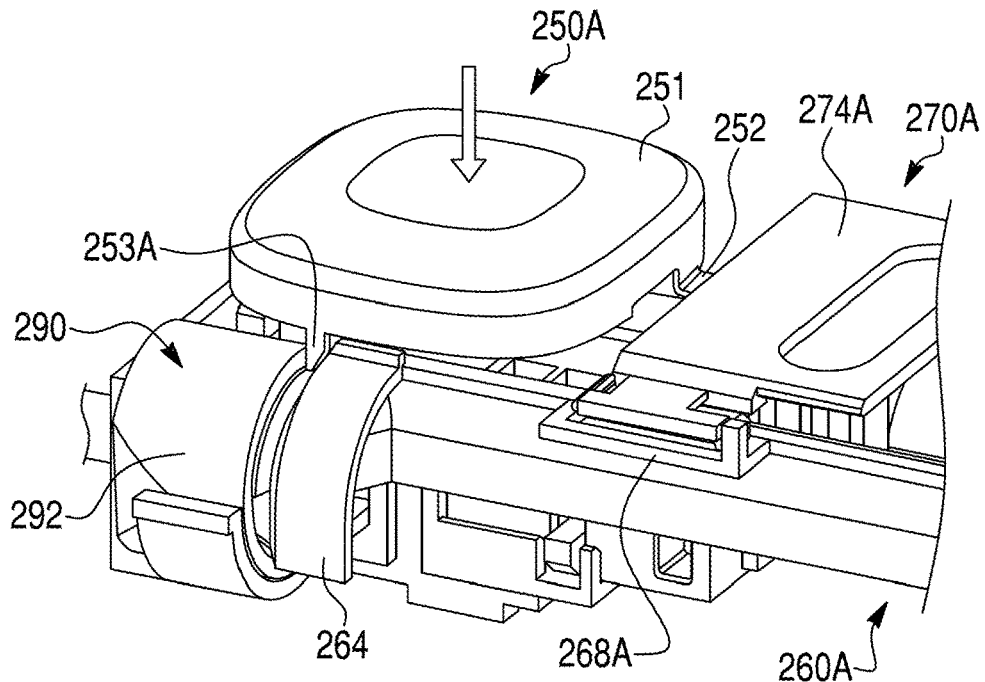
Figure 39C:
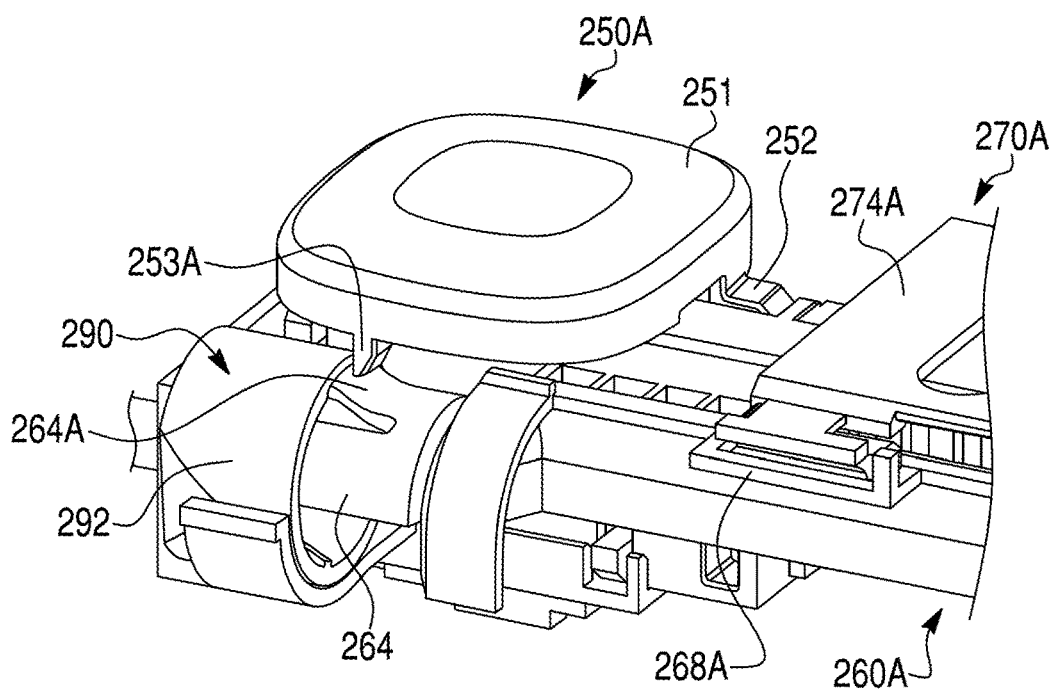

FIG. 39B shows shuttle actuator 260A in a second state during dose delivery. A second indicator (e.g., second platform 266B) may be visible through window 278 and the window on the housing of auto-injector 100. Upon completion of a dose delivery, shuttle actuator 260A may move relative to sterile connector 290, thereby removing snap connector 264A from within body 292, as seen FIG. 39C. In this instance, shuttle actuator 260A may return to a state such that snap connector 264A is locked out from entering sterile connector 290 due to an engagement with an outer edge of body 292. In this instance, graphical interface 274A may be aligned with, and visible through, the window on the housing of auto-injector 100.

Figure 40:
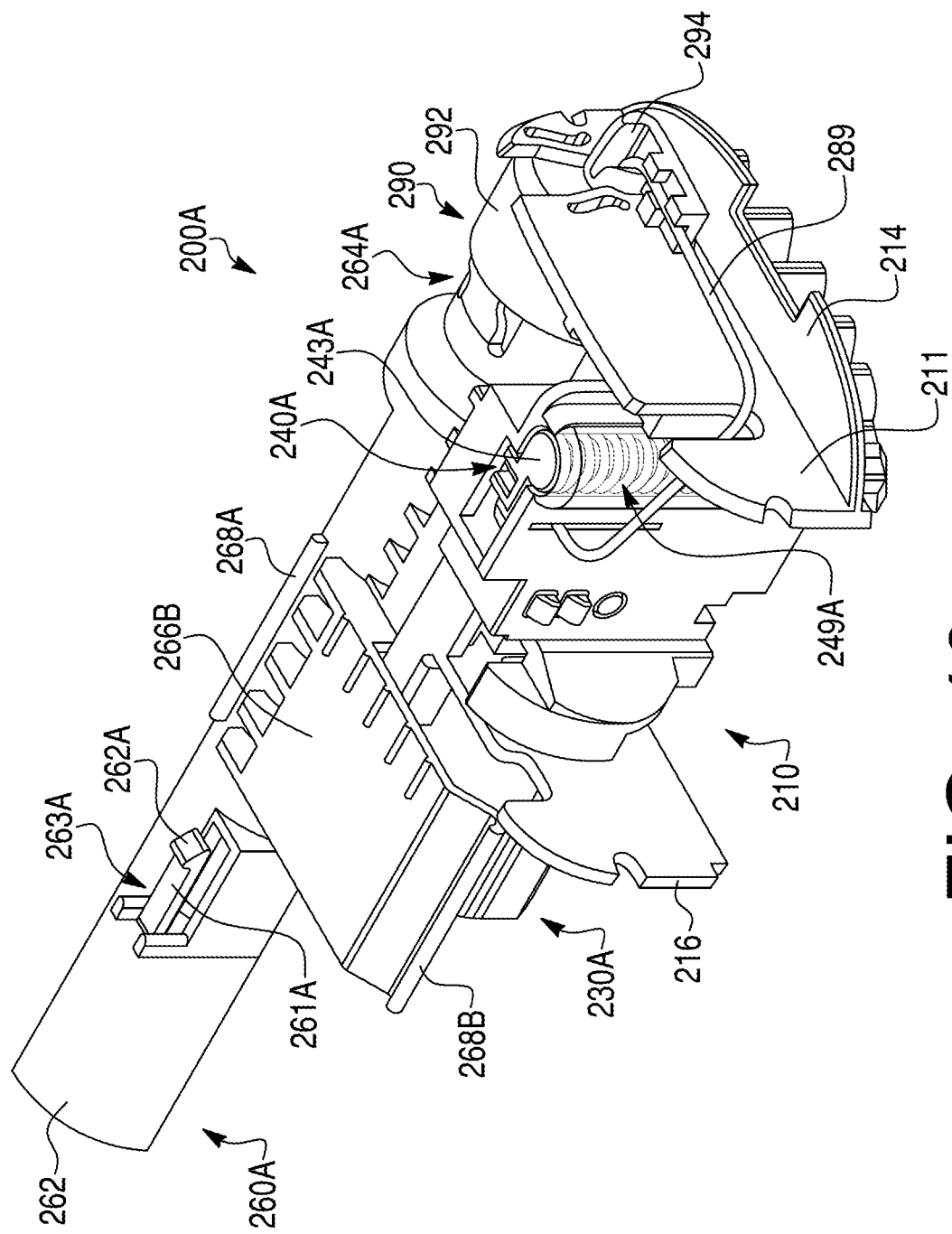
FIG. 40 is a partial perspective view of another exemplary needle mechanism of the auto-injector of FIG. 1, according to an example of the disclosure.

Referring now to FIG. 40, needle mechanism 200A may further include a driver 240A having a resilient member 249A (e.g., a spring) coupled thereto. In the embodiment, resilient member 249A may be disposed within an enclosed slot 243A of driver 240A such that resilient member 249A may be configured to apply a force onto driver 240A when transitioning from an energy-storing state to an energy-releasing state. It should be understood that in other embodiments, resilient member 249A may be omitted entirely.

In exemplary use, as seen in FIG. 41A, shuttle actuator 260A may be in a first state and driver 240A may be in a first position with resilient member 249A fully expanded in the energy-released state. Upon releasing a pressurized fluid from fluid source 50 (see FIG. 2B), shuttle actuator 260 may move in the first direction toward driver 240A and gear 229. As shown in FIG. 41B, rack 265 may mesh with gear 229 as shuttle actuator 260A travels in the first direction, thereby causing gear 229 to rotate in a first rotation direction (e.g., clockwise, counter clockwise). Driver 240A may move from the first position (FIG. 41A) to a second position due to an engagement between rack 246 and gear 229. In this instance, resilient member 249A may be compressed within enclosed slot 243A as driver 240A moves to the second position, thereby transitioning resilient member 249A from the energy-released state to the energy-storing state. The movement of driver 240A to the second position may deploy needle 286 out of the housing of auto-injector 100 (e.g., through the opening of bottom cover 110) and into a user.

Upon completing delivery of the medicament 20 (e.g., when piston 378 bottoms out at second end 374), the pressure generated within container 370 may be reduced and/or eliminated. For example, venting system 172 (FIG. 2C) may release a pressure generated within valve assembly 300 upon delivering the medicament 20 through fluid conduit 280. As seen in FIG. 41C, an opposing force applied against driver 240A by resilient member 249A may cause driver 240A to move to a third position, thereby returning to shuttle actuator 260A to the first state and/or a third state that is different from the first state. Stated differently, resilient member 249A may transition from the energy-storing state to the energy-released state, thereby moving the shuttle actuator 260A after a threshold amount of the pressurized fluid is released from fluid source 50.

In this instance, driver 240A may move from the second position to a third position in response to movement of shuttle actuator 260A. Shuttle actuator 260A may interface with gear 229 via rack 265, thereby causing rotation of gear 229 in a second rotational direction that is opposite of the first rotation direction (e.g., clockwise, counter clockwise). With rack 246 coupled to gear 229, rotation of gear 229 may cause a corresponding movement of driver 240A from the second position to the third position in a direction parallel to transverse axis 14 (see FIG. 3), thereby retracting needle 286 back into the housing of auto-injector 100. Accordingly, needle 286 may be disposed within bottom cover 110 when driver 240A is in the third position, which may be substantially similar to the first position of driver 240A.

Figure 42:
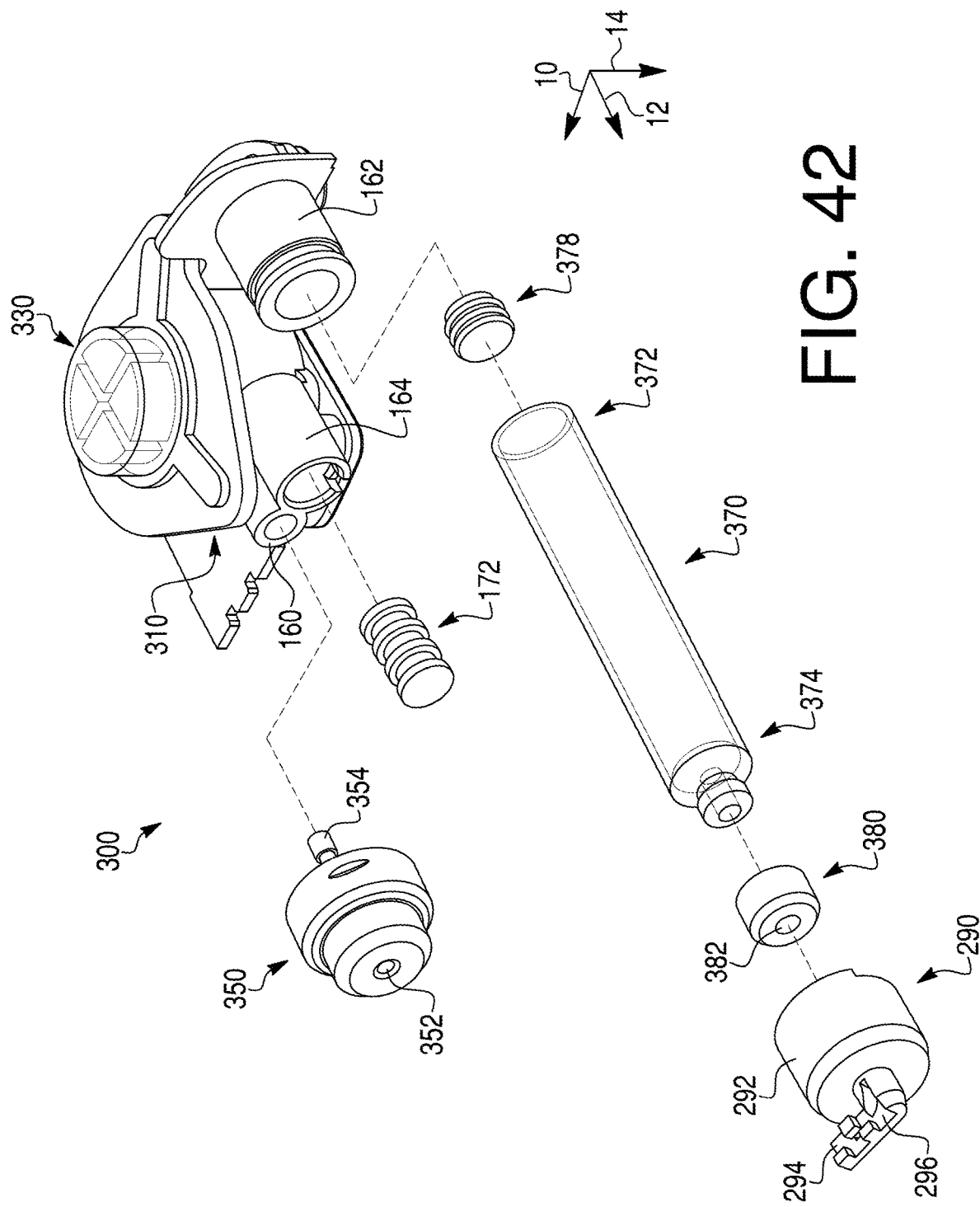
FIG. 42 is an exploded perspective view of a valve assembly of the auto-injector of FIG. 1, according to an example of the disclosure.

Referring now to FIG. 42 an implementation of valve assembly 300 is depicted. Valve assembly 300 may be compatible with container 370 whose longitudinal axis may be parallel to the surface of the skin of a patient. Valve assembly 300 may be designed to operate at a specific pressure, based on a balancing of one or more parameters including a thickness and/or durometer of diaphragm 320, a height of valve seat 166, and/or a diameter of high pressure cavity 161 (see FIGS. 2A-2C). In some embodiments, low pressure inlet 162 may include a seal to facilitate movement of cartridge 370 relative to valve assembly 300 (e.g., ranging from between 50 durometer to 70 durometer). During pressure equalization between high pressure cavity 161 and low pressure cavity 163, the low pressure in conduit 164 may create a retention force that may prevent diaphragm 320 from returning to the neutral stage (FIG. 2A). This may be avoided by reducing the diameter of conduit 164 and/or increasing the return force of diaphragm 320 by adjusting one or more of pre-tension, a thickness and/or diameter of diaphragm 320, or a height of valve seat 166. For example, a flat, stamped diaphragm 320 may shift in relation to the rest of the valve due to forces acting on it during deflection such that it may lose its return force.

Figure 43:
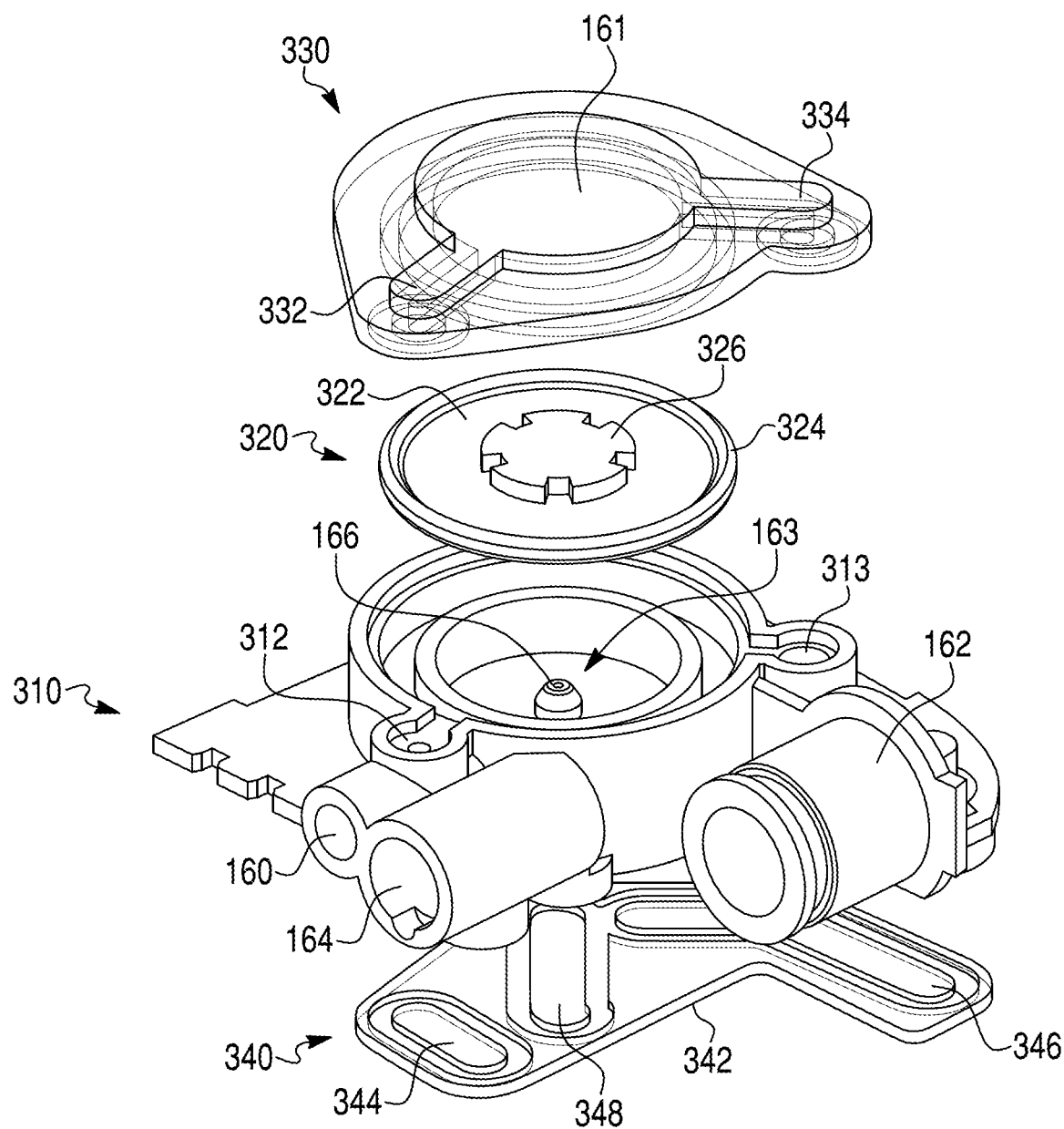
FIGS. 43-47 are perspective views of the valve assembly of FIG. 42, according to an example of the disclosure.
Figure 44:
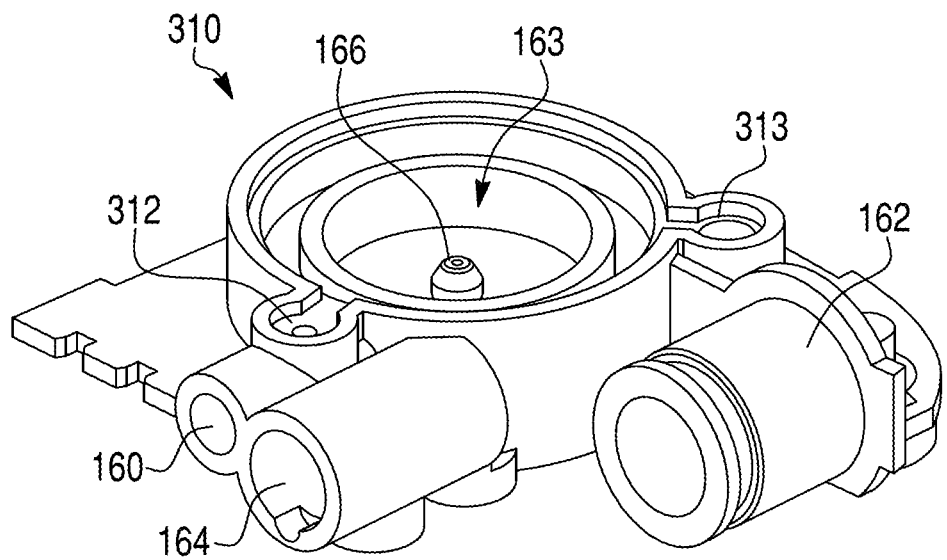
Figure 45:
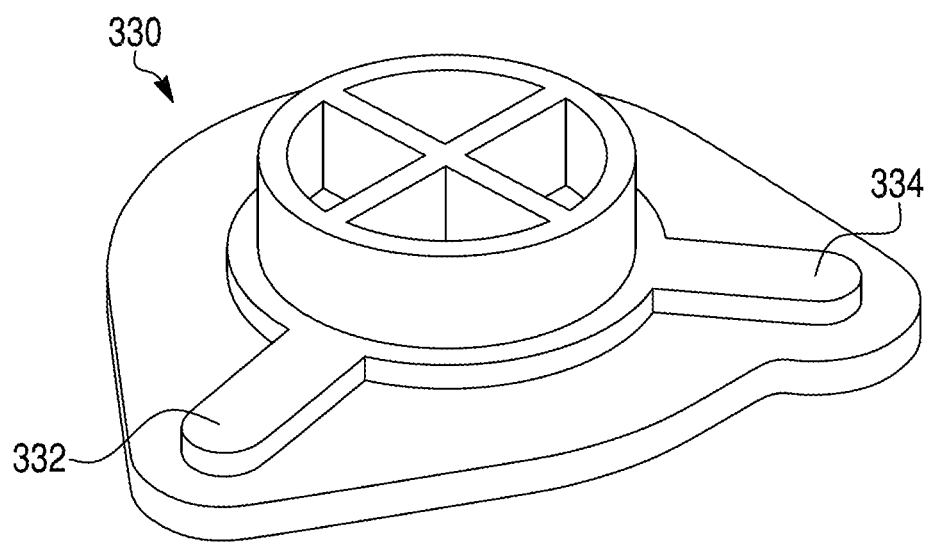

FIG. 43 illustrates a four-piece construction valve assembly 300 (including diaphragm 320). The embodiment of FIG. 43 may exhibit improved moldability and simplicity of construction, requiring only one type of weld. In some embodiments, the push rod port may be omitted. Valve assembly 300 may include low pressure body portion 310 and high pressure body portion 330. Low pressure body portion 310 may include low pressure cavity 163, and high pressure body portion 330 may include high pressure cavity 161 (FIGS. 2A-2C). In some embodiments, high pressure body portion 330 may include a tenting boss surrounding low pressure cavity 163, and that stretches diaphragm 320 (in a manner similar to a drum head) when low pressure body portion 310 and high pressure body portion 330 are mated to one another.

Valve seat 166 may be positioned within low pressure cavity 163, as shown and described above in FIGS. 2A-2C. Pressurized fluid may flow from the energy source (e.g., fluid source 350) through high pressure (first) inlet 160 on low pressure body portion 310, and flow into high pressure cavity 161 via a port 312 of low pressure body portion 310 and a channel 332 of high pressure body portion 330. Low pressure body portion 310 may further include a port 313 that contains flow restrictor 170. Low pressure body portion 310 may include low pressure inlet 162 for interfacing with container 370, and conduit 164.

Figure 46:
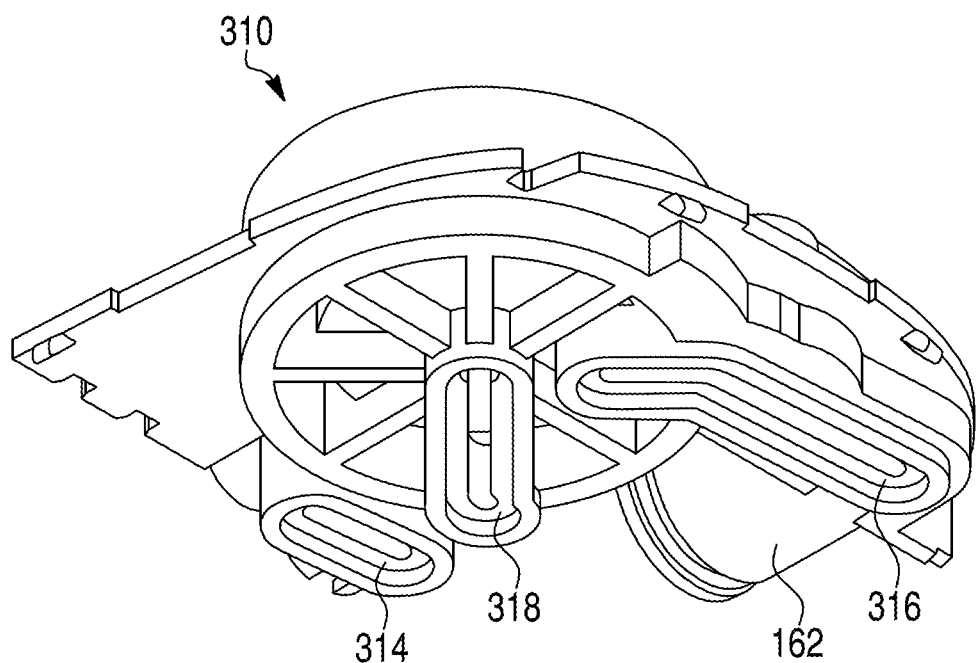
Figure 47:
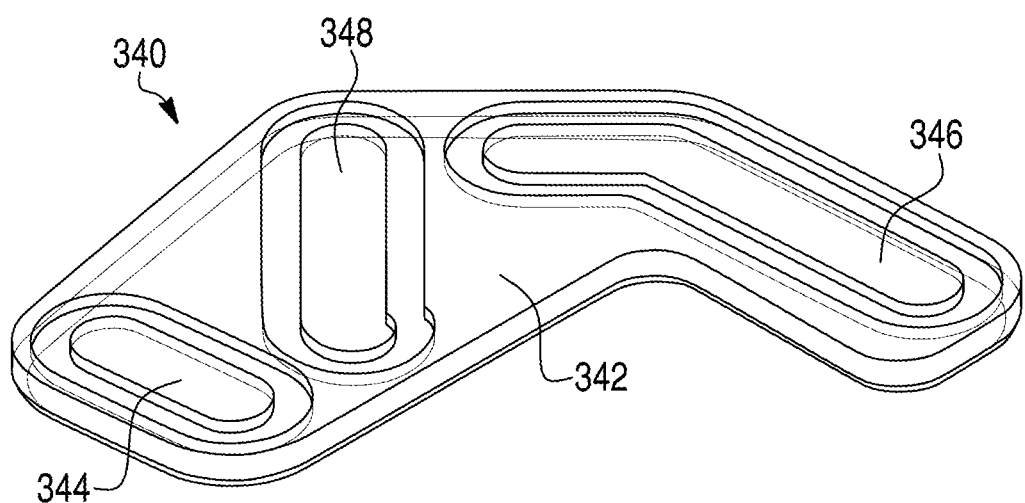

FIGS. 44-47 depict the four-piece construction valve assembly 300 disassembled into separate components, including low pressure body portion 310 (FIGS. 44 and 46), high pressure body portion 330 (FIG. 45), and a bottom cover 340 (FIG. 47). FIG. 46 illustrates one or more pressure lines 314, 316, 318 positioned along a bottom surface of low pressure body portion 310. FIG. 47 illustrates one or more pressure cavities 344, 346, 348 formed (e.g., etched) along a body 342 of bottom cover 340. Bottom cover 340 may be coupled to the bottom surface of low pressure body portion 310 such that the pressure lines 314, 316, 318 may be aligned with the pressure cavities 344, 346, 348. It should be appreciated that bottom cover 340 may allow gas from low pressure body portion 310 to travel to one or more locations in valve assembly 300 via the one or more pressure lines 314, 316, 318 and pressure cavities 344, 346, 348.

Figure 48:
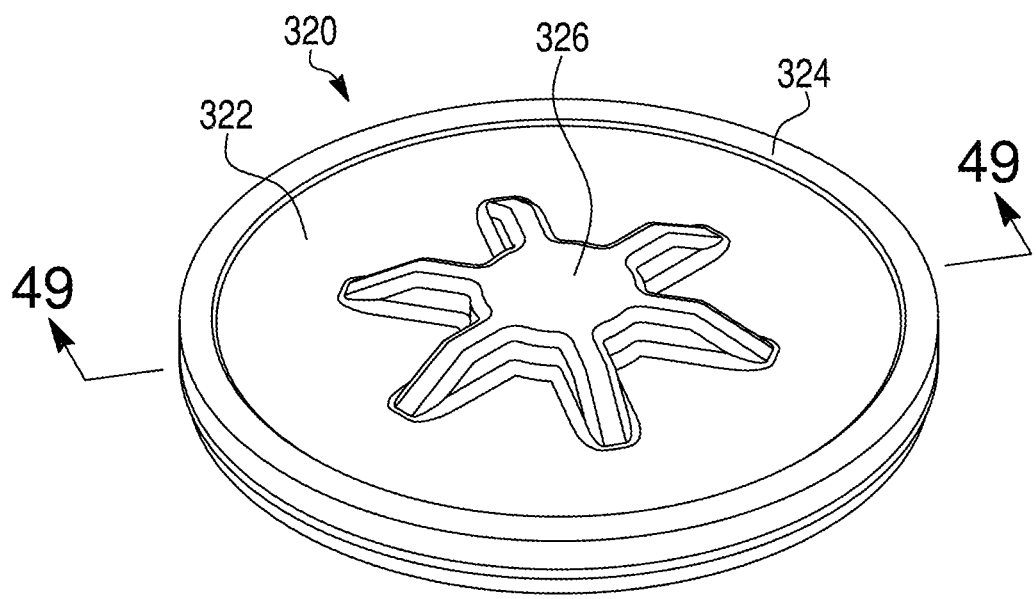
FIG. 48 is a perspective view of a diaphragm of the valve assembly FIG. 42, according to an example of the disclosure.
Figure 49:
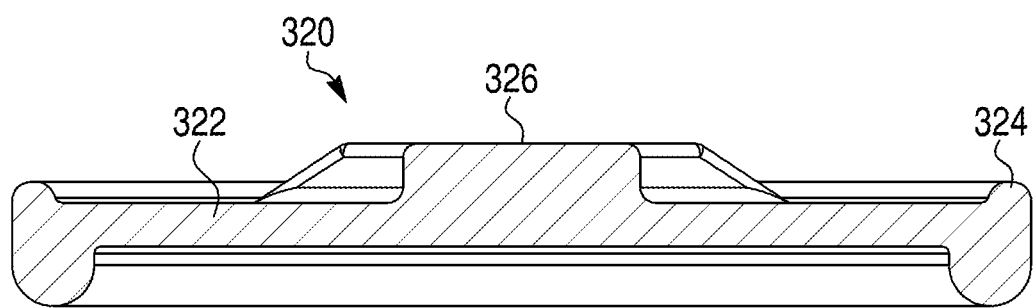
FIG. 49 is a cross-sectional side view of the diaphragm of the valve assembly FIG. 42, according to an example of the disclosure.

FIGS. 48 and 49 illustrate different views of an exemplary diaphragm 320, which may be incorporated in valve assembly 300 or any other valve as discussed herein. FIG. 48 is a perspective view of a first side of diaphragm 320. FIG. 49 is a cross-sectional view of a portion of diaphragm 320. Diaphragm 320 may have a unitary central body 322 that is generally circular. Diaphragm 320 may include an outer rim or gland 324 that extends around the periphery of body 322. Gland 324 may extend away from body 322 in opposite directions, and may include an increased thickness relative to body 322 of diaphragm 320. Gland 324 may also include a round face, for example, along an entire face of gland 324 (e.g., the surface extending perpendicularly from the radial direction of diaphragm 320). Additionally, diaphragm 320 may include a raised portion 326 positioned on and/or coupled to body 322, for example, in a radially centered position on diaphragm 320. Raised portion 326 may have a circular center, and may include a thickness (e.g., extending away from body 322). The thickness of raised portion 326, may be about 1 mm, about 2 mm, from about 0.5 mm to about 10 mm, from about 1 mm to about 9 mm, from about 3 mm to about 8 mm, from about 4 mm to about 6 mm, or about 5 mm. In some embodiments, the thickness of raised portion 326 may be at least 1 mm to assist with manufacturability. As shown, raised portion 326 may include a plurality of fingers that protrude radially outward from the center portion.

Figure 50:
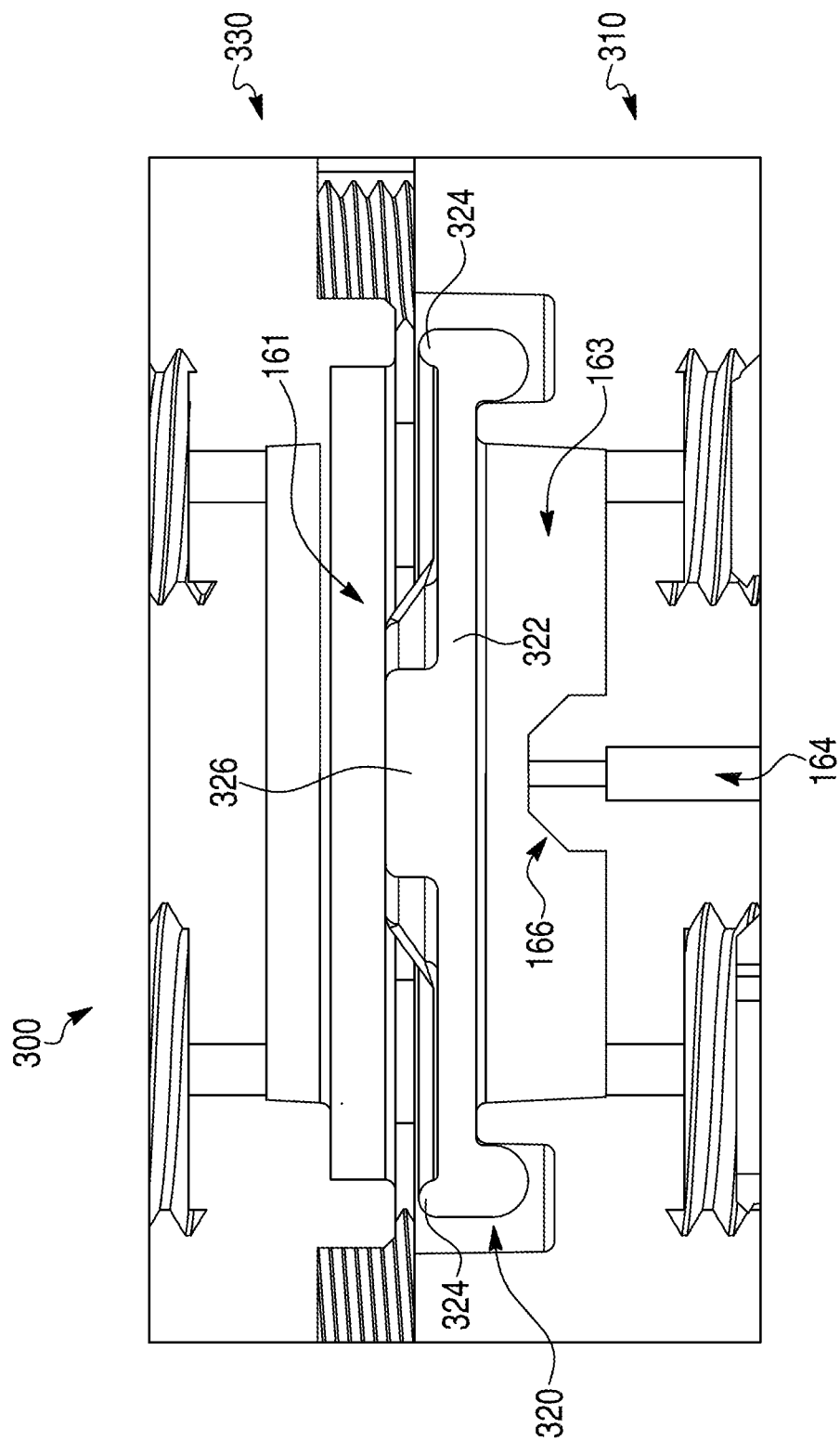
FIG. 50 is a cross-sectional side view of the diaphragm of FIG. 48 disposed within the valve assembly of FIG. 42, according to an example of the disclosure.
Figure 51A:
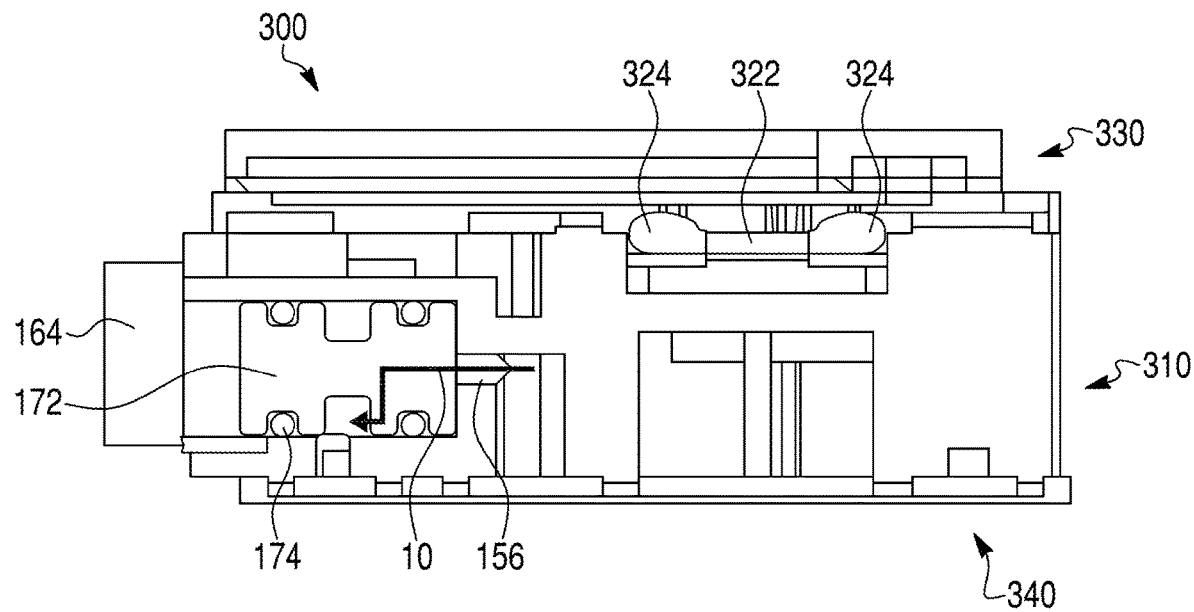
FIGS. 51A-51B are side schematic views of a vent system according to an example of the disclosure.
Figure 51B:
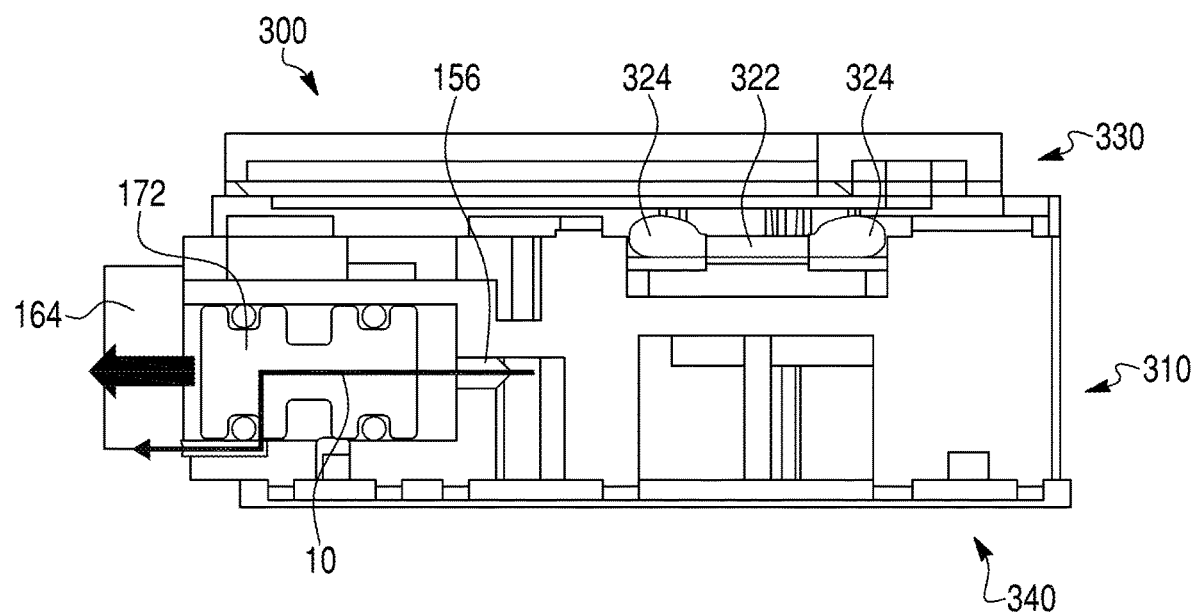

Diaphragm 320 may be formed of a unitary, single, or composite material, or any other suitable material. Diaphragm 320 with raised portion 326 may be able to receive a greater force and/or pressure, for example, such that diaphragm 320 deflects and/or changes shape more uniformly, which may help during lift-off from a valve seat at higher pressures. For example, diaphragm 320 may have a material composition having a hardness ranging from about 30 durometer to 80 durometer, such as 40 durometer. FIG. 50 shows diaphragm 320 between assembled portions 310 and 330. In an initial configuration, diaphragm 320 may be positioned in a stretched and/or tensioned state with gland 324 in contact with an upper tooth of high pressure body portion 330 and offset from a bottom surface of low pressure body portion 310 by a distance. In the embodiment, a size and/or shape of gland 324 (in both directions relative to body 322) may facilitate a deflection and lift off of diaphragm 320 at specified pressure differentials. FIGS. 51A-51B illustrate valve assembly 300 in fluid communication with venting system 172, and particularly a fluid path 10 that travels through valve assembly 300 when venting system 172 is in a first position (FIG. 51A) and a second position (FIG. 51B).

Figure 52:
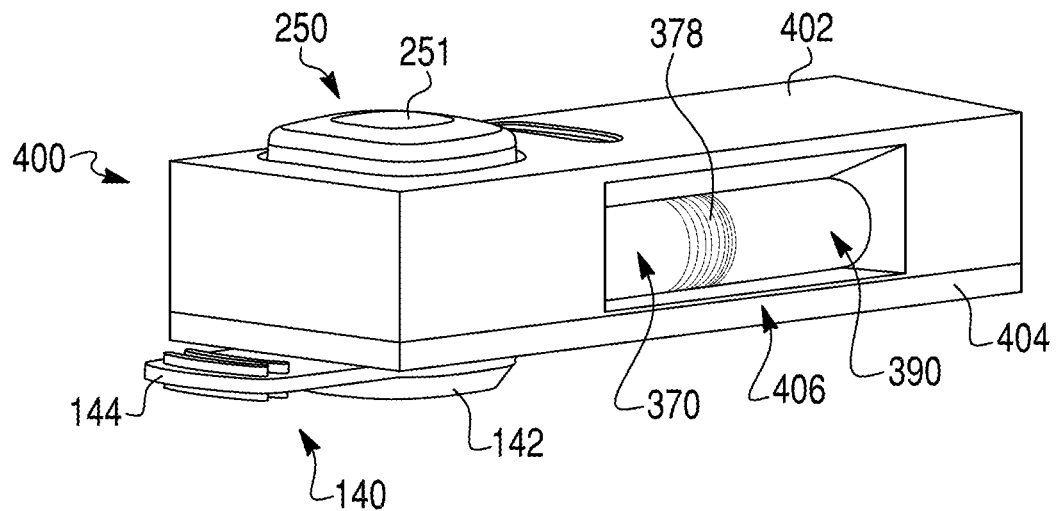
FIG. 52 is a perspective view of another auto-injector, according to an example of the disclosure.

Referring now to FIG. 52, another implementation of an auto-injector is depicted. Auto-injector 400 may be configured and operable similar to auto-injector 100 shown and described above except for the differences explicitly noted herein. Accordingly, like reference numerals are used to identify like components. In the embodiment, auto-injector 400 may include a housing having a top cover 402, a bottom cover 404, and a window 406 formed along a sidewall of top cover 402. Window 406 may include a transparent or partially-transparent material, and may provide an opening to facilitate a visual inspection of one or more internal components of auto-injector 400, such as piston 378, container 370, and the fluid stored therein. In other embodiments, window 406 may be positioned along various other walls and/or surfaces of auto-injector 400 from which container 370 may be visible. For example, window 406 may be positioned along a bottom surface of bottom cover 404, a top surface of top cover 402, and/or along multiple surfaces of the housing. Auto-injector 400 may further include a plug assembly 390 disposed within container 370 and positioned against piston 378, as described in further detail herein.

Figure 53:
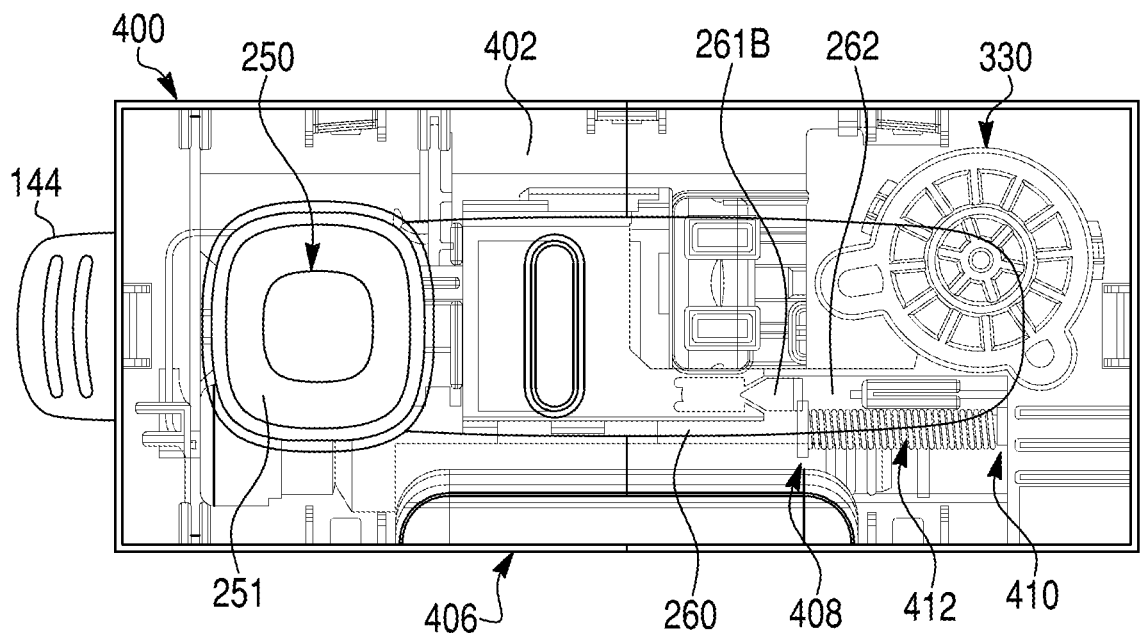
FIG. 53 is a partial top view of the auto-injector of FIG. 52, according to an example of the disclosure.
Figure 54:
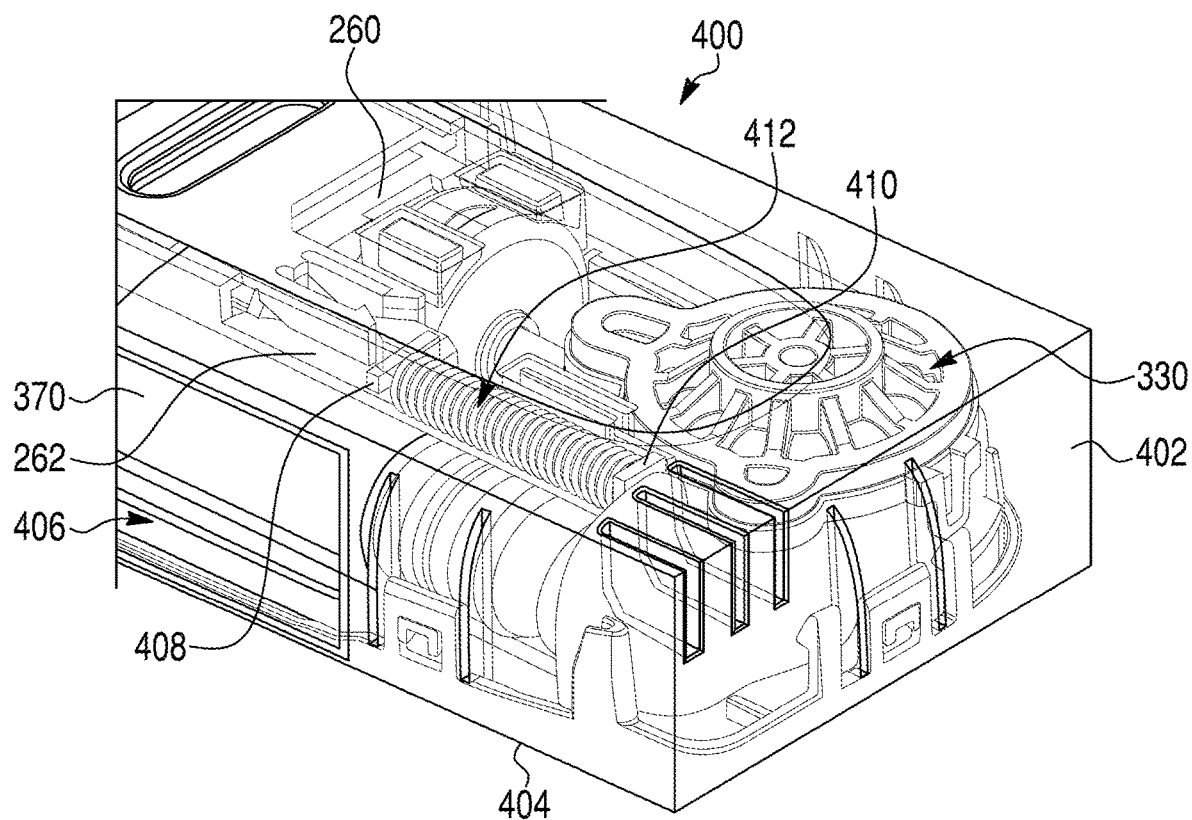
FIG. 54 is a partial perspective view of the auto-injector of FIG. 52, according to an example of the disclosure.

As seen in FIGS. 53-54, auto-injector 400 may include a resilient member 412 (e.g., a spring) disposed between a first flange 408 and a second flange 410. First flange 408 may extend outwardly (e.g., downward) from an interior surface of top cover 402, and second flange 410 may extend outwardly (e.g., upward) from a top surface of first end 262 of shuttle actuator 260. First flange 408 may be positioned relative to top cover 402 at a location that overlaps with first end 262 of shuttle actuator 260. Second flange 410 may be configured to move relative to first flange 408 in response to a movement of shuttle actuator 260. In this instance, shuttle actuator 260 may be configured to transition resilient member 412 from an energy-releasing state (expanded configuration) to an energy-storing state (compressed configuration) by moving second flange 410 toward first flange 408, thereby compressing resilient member 412.

In exemplary use, resilient member 412 may be compressed as shuttle actuator 260 moves in response to an actuation of needle mechanism 200, as shown and described in further detail above. Accordingly, shuttle actuator 260 may compress resilient member 412 as fluid conduit 280 extends outwardly from a housing of auto-injector 400 for delivering the fluid substance to a patient. In response to auto-injector 400 releasing the pressurized fluid (i.e., venting), as shown and described in detail above with respect to venting system 172, a force stored by resilient member 412 when compressed between first flange 408 and second flange 410 may be released, causing resilient member 412 to return to the expanded configuration and move shuttle actuator 260 to its original position. In this instance, needle 286 of fluid conduit 280 may be simultaneously retracted into the housing of auto-injector 400.

It should be appreciated that resilient member 412 may be incorporated in auto-injector 400 in conjunction with resilient member 249A shown and described above. In this instance, the structural requirements of resilient member 249A, for generating a sufficient force to deploy and retract needle 286, may be reduced. Stated differently, resilient member 249A may be configured to generate a necessary extension (actuation) force of needle 286 while resilient member 412 may be configured to generate a separate, retraction force. Accordingly, auto-injector 400 may separate the components required to generate each of the respective forces, thereby reducing the individual requirements of each resilient member. In the embodiment, each of the respective resilient members may only be required to generate one of the two energy-states for operating auto-injector 400. In other embodiments, resilient member 249A may be omitted entirely such that resilient member 412 may be configured to generate both an insertion force and retraction force of needle 286.

Figure 55:
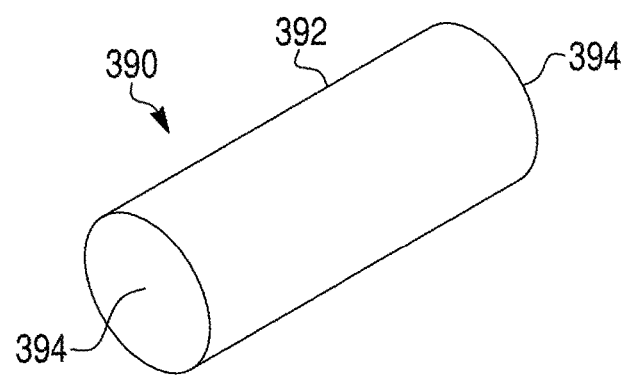
FIG. 55 is a perspective view of a plug assembly of the auto-injector of FIG. 52, according to an example of the disclosure.

Referring now to FIG. 55, plug assembly 390 is depicted in accordance with an example of the present disclosure. Plug assembly 390 may have a body 392 with a longitudinal length defined between opposing ends 394. In the example, body 392 may have a cross-sectional profile that is sized and shaped to be received within container 370. Body 392 may have various suitable shapes and/or sizes without departing from a scope of this disclosure. In one embodiment, body 392 may be generally cylindrical.

Figure 56:
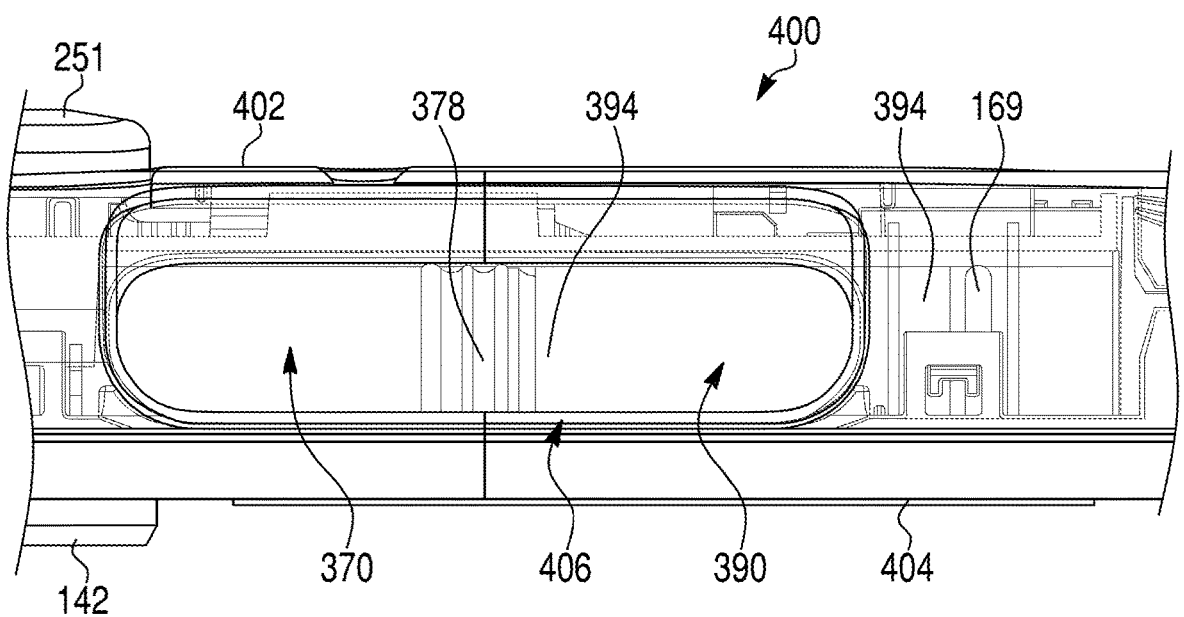
FIG. 56 is a partial side view of the plug assembly disposed within the auto-injector of FIG. 52, according to an example of the disclosure.

As best seen in FIG. 56, plug assembly 390 may be disposed within container 370 with one of the ends 394 abutting against piston 378, and the opposing end 394 abutting against a valve boss 169 of high pressure (first) inlet 160. Plug assembly 390 may be configured to occupy at least a portion of the cavity in container 370. The longitudinal length and/or diameter of body 392 may correspond to a volume within container 370 that is occupied by plug assembly 390 such that a remaining volume of container 370 may be filled with a fluid substance for delivery to a patient. For example, body 392 may have a longitudinal length and/or diameter that corresponds to 1 milliliter of fluid substance, 2 milliliter of fluid substance, etc.

In the embodiment, plug assembly 390 may be sized in accordance with a diameter of container 370 such that body 392 may be positioned flush against an interior surface of container 370, thereby inhibiting fluid from traveling around plug assembly 390. In other embodiments, body 392 may be sized less than a diameter of container 370 to allow a pressurized fluid (e.g., gas) to travel about plug assembly 390. In further embodiments, plug assembly 390 may have an internal channel (not shown) extending through a longitudinal length of body 392 with an opening at each of the opposing ends 394. The internal channel extending through body 392 may be configured to facilitate a transfer of the pressurized fluid through plug assembly 390. In an alternative embodiment, some portions of plug assembly may be porous, and those porous portions may extend along a longitudinal length of the plug assembly 390.

In another example, plug assembly 390 may be integral with one or more of piston 378 and/or valve boss 169. It should be appreciated that plug assembly 390 may be operable to facilitate use of auto-injector 400 for delivering fluid doses of lower volume to a patient by occupying a greater portion of container 370. Plug assembly 390 may be configured to minimize a delayed duration for delivering the fluid from container 370, relative to the actuation of button 250, by occupying a vacant portion of container 370 between piston 378 and valve boss 169 when the cavity of container 370 is filled with a volume of fluid substance that is less than a total capacity of container 370.

Figure 57A:
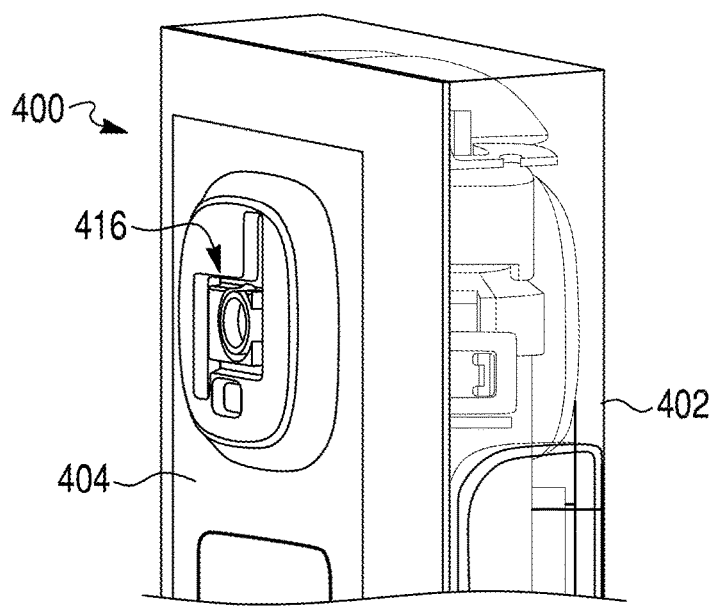
FIGS. 57A-57C are partial bottom views of a needle shroud mechanism of the auto-injector of FIG. 52, according to an example of the disclosure.
Figure 57B:
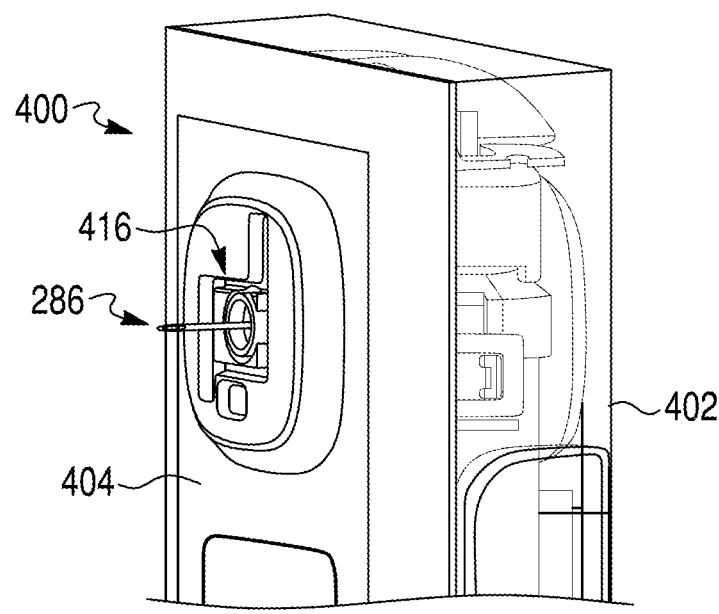
Figure 57C:
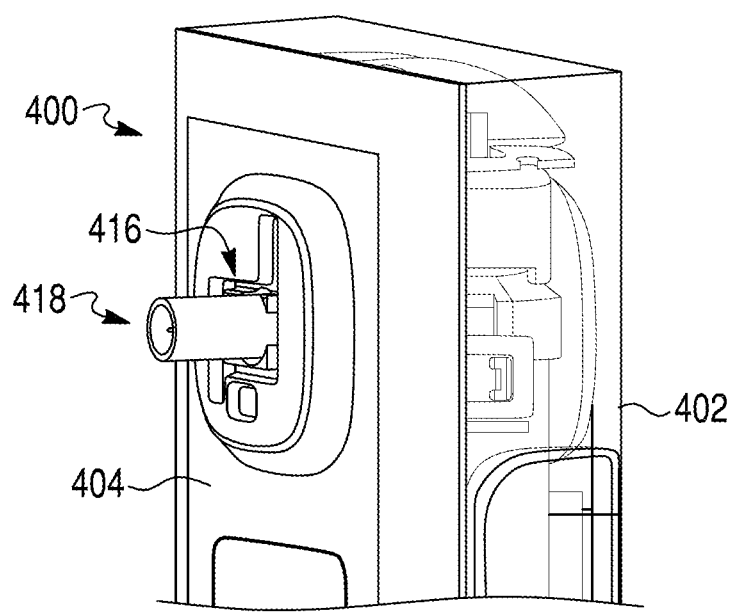

Referring now to FIGS. 57A-57C, auto-injector 400 may include an opening 416 along bottom cover 404. As described above, opening 416 may be configured to allow at least a portion of fluid conduit 280 to extend outwardly from the housing of auto-injector 400 when delivering the fluid substance to a patient. In an initial configuration, as seen in FIG. 57A, fluid conduit 280 may be fully disposed within the housing of auto-injector 400, such that needle 286 is not extending through opening 416 prior to substance delivery. Referring now to FIG. 57B, and in response to an actuation of needle mechanism 200 (as described in detail above) by button 250 (see FIG. 3), needle 286 may extend outwardly (e.g., downward) from bottom cover 404 via opening 416 to facilitate delivery of the fluid substance to a patient.

As seen in FIG. 57C, auto-injector 400 may include a needle shroud mechanism 418 that is coupled to an internal resilient member (e.g., spring) disposed within the housing of auto-injector 400. Needle shroud mechanism 418 may be spring-loaded and configured to extend outwardly from the housing via opening 416 in response to one or more trigger events. In some embodiments, the one or more trigger events may be a mechanical response by needle shroud mechanism 418, such as, for example, in response to a manual interaction with auto-injector 400. In an example of a trigger event, needle shroud mechanism 418 may be deployed through opening 416 to cover needle 286 in response to the manual removal of auto-injector 400 from contact with a patient during an active delivery of the fluid substance. In this instance, the internal resilient member may extend needle shroud mechanism 418 outwardly from opening 416 upon the premature removal of auto-injector 400, thereby enclosing needle 286 to reduce a likelihood of inadvertent contact with the patient. It should be appreciated that needle shroud mechanism 418 may remain disposed within the housing of auto-injector 400 after delivery of the fluid substance (and retraction of needle 286 into the housing) when the trigger event is not achieved.

In another example of a trigger event, needle shroud mechanism 418 may be configured to automatically extend out of opening 416 in response to completing delivery of the fluid substance from auto-injector 400. In this instance, needle 286 may be configured to remain outside of the housing upon delivering the fluid substance to the patient, such that needle shroud mechanism 418 may be deployed to cover needle 286 once auto-injector 400 completes fluid delivery and is removed from the patient's body. In either example, it should be understood that needle shroud mechanism 418 may be configured to lock-out when in the extended state to prevent retraction of needle shroud mechanism 418 into the housing once deployed.

In one embodiment, needle shroud mechanism 418 may include one or more snap tabs that are configured to interface with the carrier to lock (fix) needle shroud mechanism 418 in the extended configuration once deployed from the housing of auto-injector 400. In response to needle shroud mechanism 418 being deployed outwardly from the housing, the one or more snap tabs may inhibit needle shroud mechanism 418 from translating back into the carrier, thereby maintaining needle shroud mechanism 418 over needle 286.

In other embodiments, needle shroud mechanism 418 may be maintained in an initial, extended configuration. For example, needle shroud mechanism 418 may extend out of auto-injector 400 and be disposed within a blister pack prior to use. In another example, needle shroud mechanism 418 may be spring-biased and configured to extend out of auto-injector 400 as a user removes auto-injector 400 from a blister pack. In either instance, needle shroud mechanism 418 may be configured toward the extended configuration prior to a use of auto-injector 400. Further, needle 286 may be positioned in either an extended state and/or an enclosed state relative to auto-injector 400. Auto-injector 400 may facilitate an identification of the needle's location to a user prior to use when needle 286 is maintained in the extended state.

With needle shroud mechanism 418 maintained in an extended configuration, auto-injector 400 may be configured such that needle shroud mechanism 418 is compressed into the housing of auto-injector 400 in response to a user positioning the housing against an injection site (e.g., a body). Needle shroud mechanism 418 may be configured to interact with a locking mechanism (not shown) capable of releasing a lock inhibiting movement of button 250, thereby rendering button 250 operable for actuation to initiate delivery of fluid from auto-injector 400.

Figure 58A:
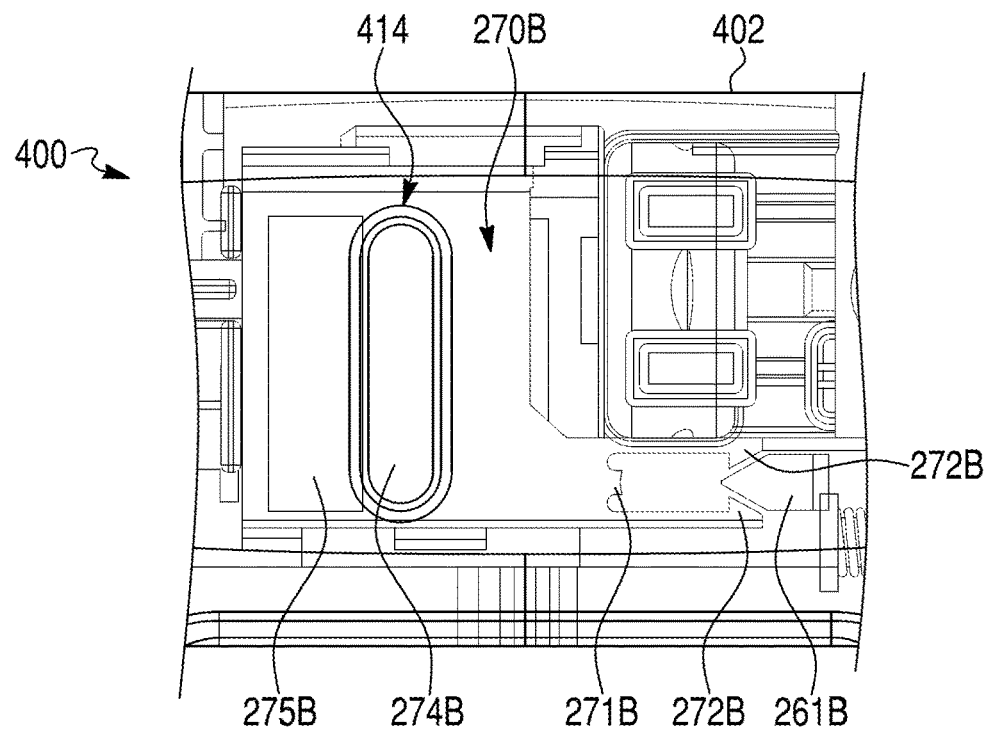
FIGS. 58A-58C are partial top views of an indicator slide of the auto-injector of FIG. 52, according to an example of the disclosure.
Figure 58B:
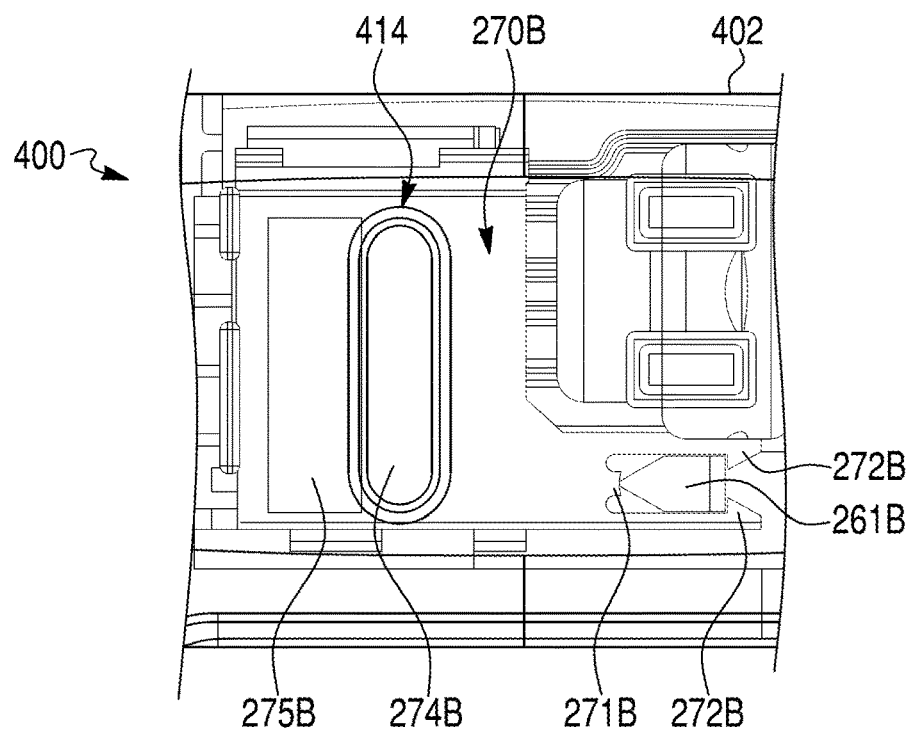
Figure 58C:
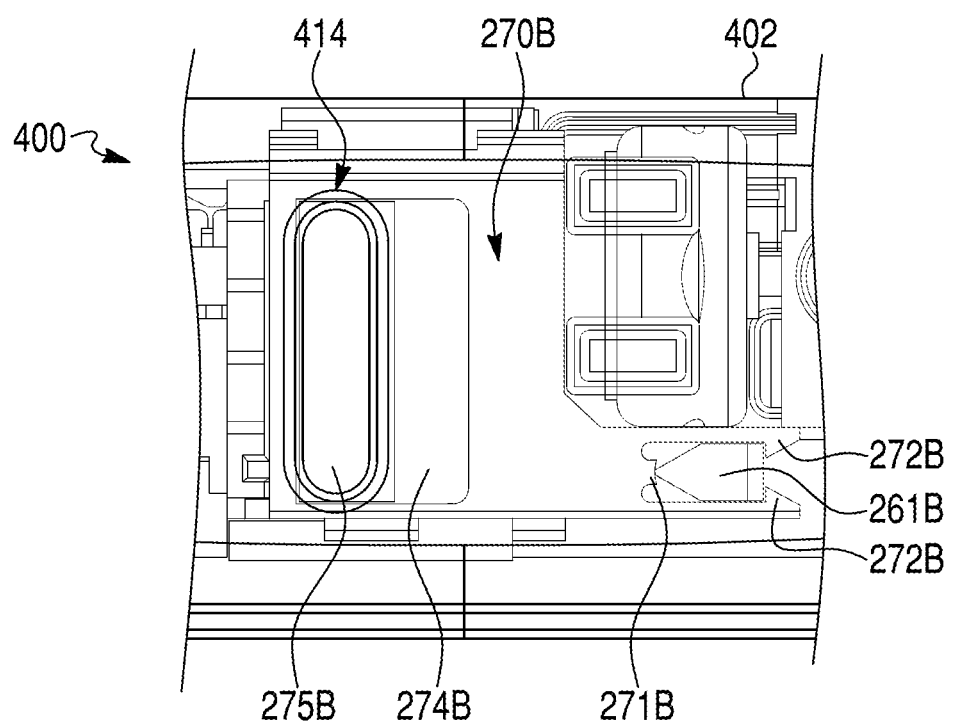

Referring now to FIGS. 58A-58C, an indicator slide 270B of auto-injector 400 is depicted. In the example, auto-injector 400 may include a window 414 along top cover 402 for providing visualization of one or more internal components of auto-injector 400, such as indicator slide 270B. Indicator slide 270B may be substantially similar to indicator slide 270 shown and described above. For example, indicator slide 270B may include a pair of legs 272B and a body 274B, with the pair of legs 272B configured to couple body 274B to shuttle actuator 260. In the example, the pair of legs 272B are configured and operable similar to legs 272 described in detail above. For example, the pair of legs 272B may be separated from one another by a cavity that is sized and shaped to receive a projection 261B of shuttle actuator 260.

In the example, indicator slide 270B may include one or more relief cuts 271B positioned between the pair of legs 272B. Relief cuts 271B may be operable to increase an effective longitudinal length of each of the pair of legs 272B, thereby enhancing a flexibility of each leg 272B. In other words, providing relief cuts 271B into body 274B adjacent to the pair of legs 272B may allow legs 272B greater lateral space to flex upon receipt of protrusion 261B. By increasing a flexibility of legs 272B, indicator slide 270B may be configured to decrease a force required to deflect the pair of legs 272B when projection 261B is translated therebetween to couple shuttle actuator 260 to indicator slide 270B. Decreasing a force necessary to couple shuttle actuator 260 to indicator slide 270B may allow fluid substances with relatively lower viscosities to be delivered from auto-injector 400.

Referring specifically to FIG. 58A, indicator slide 270B may include a graphical indicator 275B (e.g., a color, a text, a marking, etc.) on a top surface of body 274B. Graphical indicator 275B may be indicative of a current state of auto-injector 400, and may be viewable by a user through window 414. Indicator slide 270B may be configured to provide an indication of two states during use of auto-injector 400. For example, with indicator slide 270B in an initial position relative to shuttle actuator 260 (e.g., prior to an engagement of projection 261B by legs 272B), graphical indicator 275B may be misaligned with window 414 such that indicator slide 270B may identify a first (new) state of auto-injector 400 to a user.

As seen in FIG. 58B, upon translating shuttle actuator 260 relative to indicator slide 270B to deploy needle 286 from the housing of auto-injector 400, a position of graphical indicator 275B relative to window 414 may remain unchanged such that indicator slide 270B may continue to identify the first (new) state of auto-injector 400 to the user. Stated differently, with indicator slide 270B remaining fixed as the pair of legs 272B receive projection 261B, a relative position of body 274B may be the same such that graphical indicator 275B continues to be misaligned from window 414.

With indicator slide 270B coupled to shuttle actuator 260 via the engagement between the pair of legs 272B and projection 261B, shuttle actuator 260 may be configured to move indicator slide 270B. For example, shuttle actuator 260 may cause indicator slide 270B to move when needle 286 is retracted into the housing of auto-injector 400, such as, for example, in response to the expansion of resilient member 412 which causes a corresponding movement of shuttle actuator 260. As seen in FIG. 58C, body 274B may be moved relative to top cover 402, causing graphical indicator 275B to move into alignment with window 414. In this instance, indicator slide 270B may identify a second (used) state of auto-injector 400 to a user through window 414.

In other embodiments, auto-injector 400 may include indicator slide 270 shown and described above (see FIG. 3). Indicator slide 270 may include window 278 and shuttle actuator 260 may include three indicators on second platform 266B as described in further detail above. In this instance, the first and second indicators on second platform 266B may be the same and indicative of the first (new) state of auto-injector 400. The third indicator on second platform 266B may be different than the first and second indicators, and indicative of the second (used) state. Accordingly, auto-injector 400 may continue to provide an indication of two states during use of auto-injector 400 with indicator slide 270 including three graphical indicators.

Figure 59:
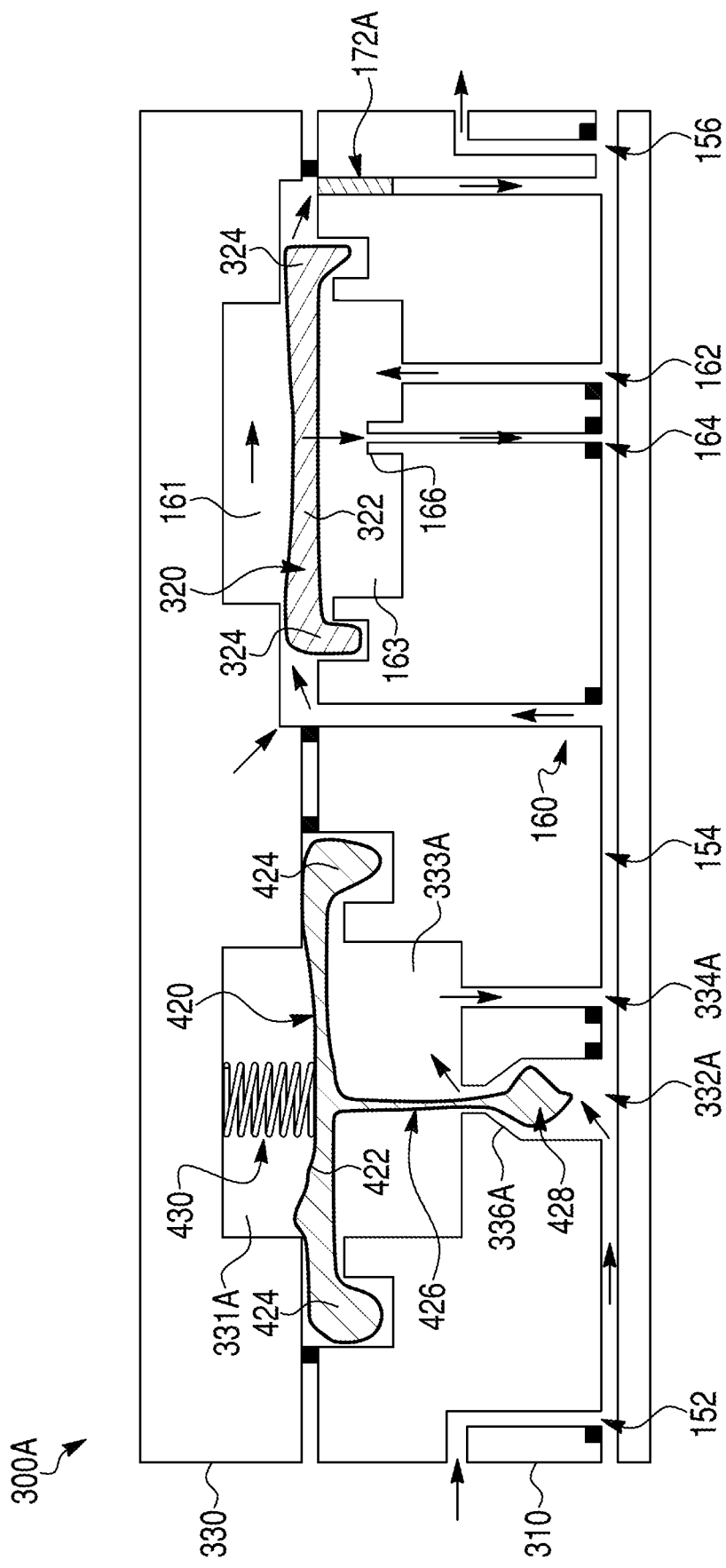
FIG. 59 is a schematic illustration of features of an auto-injector, according to an example of the disclosure.

Referring now to FIG. 59, a valve assembly 300A of auto-injector 400 is depicted. Valve assembly 300A may be substantially similar to valve assembly 300 shown and described above such that like reference numerals are used to identify like components. For example, valve assembly 300A may include a low pressure body portion 310 and a high pressure body portion 330. Valve assembly 300A may be operatively coupled to fluid conduit 280 via container 370. In the example, valve assembly 300A may include a regulator 420 and diaphragm 320 positioned between low pressure body portion 310 and high pressure body portion 330. Regulator 420 may include a central body 422 and an outer rim or gland 424 disposed about central body 422. Regulator 420 may further include a leg 426 extending outwardly (e.g., downward) from central body 422.

Within valve assembly 300A, regulator 420 defines a first cavity 331A and a second cavity 333A that is separate from the high pressure (first) cavity 161 and low pressure (second) cavity 163 defined by diaphragm 320. Valve assembly 300A may include a resilient member 430 (e.g., a spring) disposed within first cavity 331A and positioned between an internal (top) surface of high pressure body portion 330 and central body 422. Resilient member 430 may be configured to apply a downward force against regulator 420 toward second cavity 333A. Leg 426 may extend into second cavity 333A, and may include a foot 428 at a terminal end of leg 426 opposite of central body 422. In the example, foot 428 may have a cross-sectional profile that is greater than leg 426. For example, foot 428 may have an enlarged (bulbous) shape that is sized relatively greater than a valve seat 336A positioned below and leading into second cavity 333A. As described herein, foot 428 may be configured to interface with valve seat 336A to selectively inhibit fluid communication between high pressure line 152 and second cavity 333A.

Still referring to FIG. 59, second cavity 333A may be in fluid communication with high pressure line 152 via an inlet 332A, and in communication with low pressure line 154 via an outlet 334A. Low pressure line 154 may be in further fluid communication with high pressure (first) inlet 160. Regulator 420 may be configured to minimize an accumulation of high pressure within auto-injector 400 from the use of pressurized fluid to deliver the fluid substance to a patient.

For example, in a pre-activated state of auto-injector 400, a propellant (e.g., pressurized gas) dispensed from fluid source 350 may flow through high pressure line 152. Some pressurized gas from high pressure line 152 may be diverted toward inlet 332A and into second cavity 333A. Upon entering second cavity 333A, the pressurized gas may cause regulator 420 to move into first cavity 331A and resilient member 430 to compress. As central body 422 is urged upward into first cavity 331A, leg 426 and foot 428 are simultaneously moved in an upward direction until foot 428 interfaces with valve seat 336A, thereby sealing first cavity 331A and second cavity 333A.

Still referring to FIG. 59, with valve seat 336A sealed by foot 428, the pressurized gas causing regulator 420 to move into first cavity 331A may exit second cavity 333A at outlet 334A, thereby reducing the pressure within second cavity 333A. The pressure difference between first cavity 331A and second cavity 333A may allow an energy stored by resilient member 430 (from its compression in first cavity 331A) to move regulator 420 toward the second cavity 333A as it returns to an expanded configuration. Resilient member 430 may cause central body 422 and leg 426 to move, thereby decoupling foot 428 from valve seat 336A. Regulator 420 may continue to move (e.g., oscillate) relative to first cavity 331A and second cavity 333A as high pressurized gas is received in second cavity 333A (via inlet 332A) and released from second cavity 333A (via outlet 334A), thereby causing resilient member 430 to compress and expand when an equilibrium state is achieved between the cavities.

The pressurized gas exiting second cavity 333A at outlet 334A may be directed to low pressure line 154 to travel to high pressure (first) inlet 160. In this instance, the pressurized gas received in high pressure (first) inlet 160 may cause diaphragm 320 to move into low pressure cavity 163 and toward conduit 164, thereby sealing valve seat 166. The pressurized gas received in high pressure cavity 161 may be directed toward a flow restrictor 172A (e.g., a frit) that may be configured and operable similar to flow restrictor 170 shown and described in detail above. A material of flow restrictor 172A may cause a pressure drop to be experienced in the pressurized gas flowing through it from high pressure cavity 161, and the pressure-reduced gas is then diverted to third line 156 where the gas may vent out, such as, for example, in drive system 150 (see FIGS. 2A-2C).

Still referring to FIG. 59, a reduced-pressure gas diverted into low pressure cavity 163 via low pressure inlet 162 may cause a pressure difference between high pressure cavity 161 and low pressure cavity 163. The pressure difference may provide the force required to seal conduit 164 by diaphragm 320. As the pressure across high pressure cavity 161 and low pressure cavity 163 equilibrates, diaphragm 320 may lift off of valve seat 166 and open conduit 164, thereby allowing the gas in low pressure cavity 163 to travel to third line 156 where the gas may vent out in drive system 150 (see FIGS. 2A-2C).

Figure 60A:
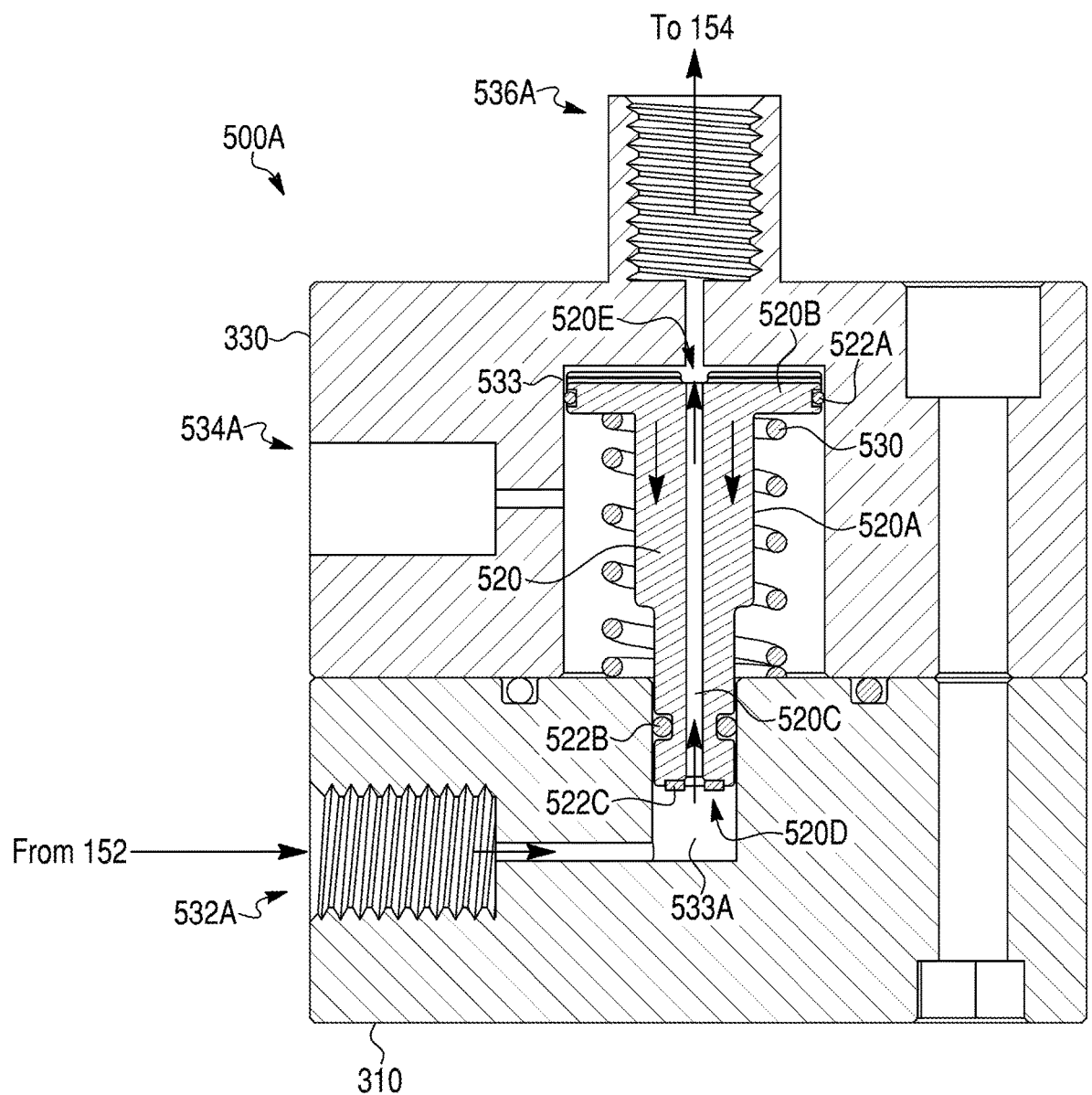
FIGS. 60A-60B are schematic illustrations of yet additional features of an auto-injector, according to an example of the disclosure.
Figure 60B:
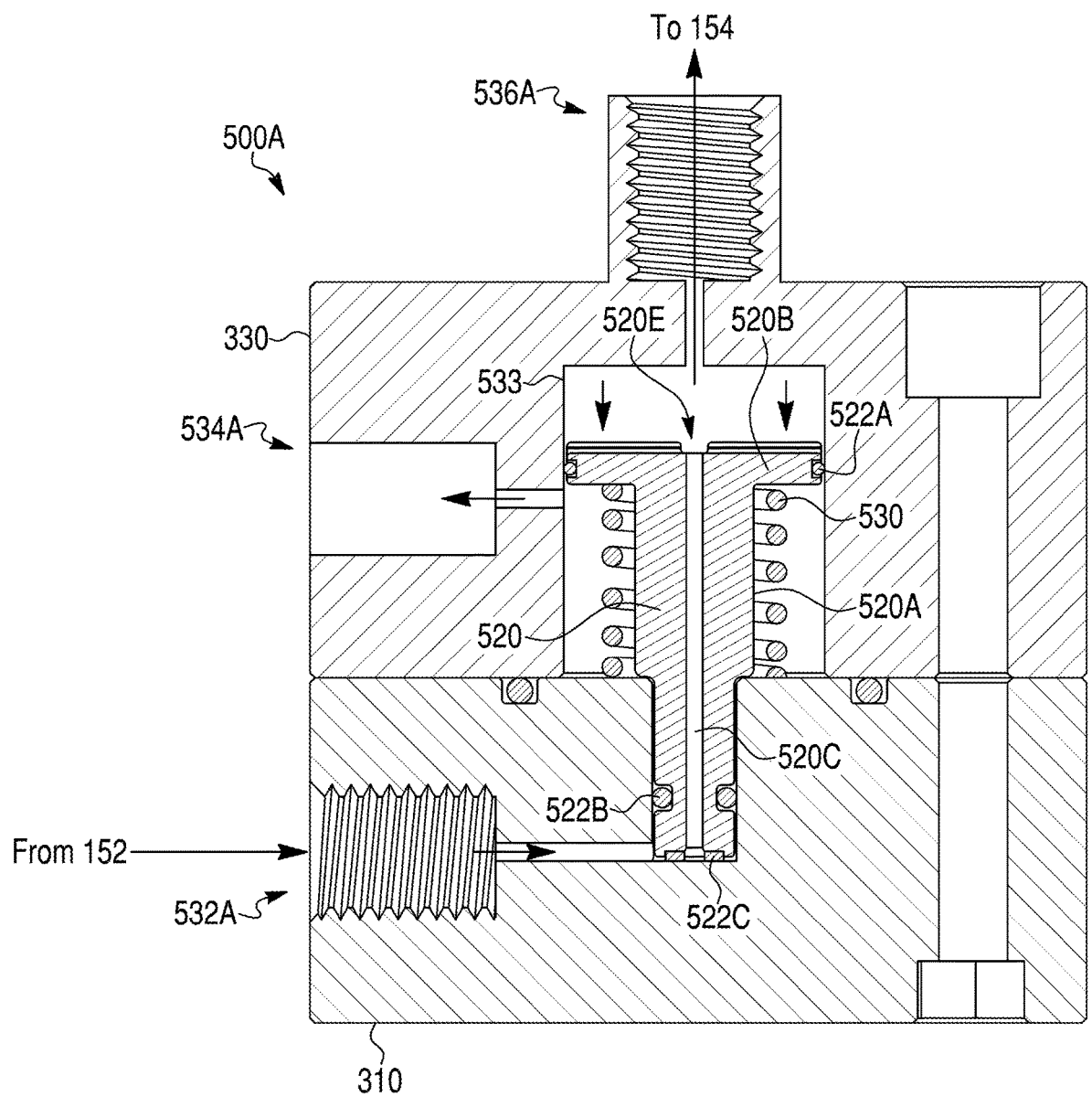

Referring now to FIGS. 60A-60B, a valve assembly 500A of auto-injector 400 is depicted. Valve assembly 500A may be substantially similar to valve assembly 300A described herein. For example, valve assembly 500A may include a low pressure body portion 310, and a high pressure body portion 330. Valve assembly 500A may be operatively coupled to fluid conduit 280 via container 370. In the example, valve assembly 500A may include a regulator 520 positioned between low pressure body portion 310 and high pressure body portion 330. Regulator 520 may be a piston including a rod 520A extending from a flange 520B. Flange 520B may be disposed only within high pressure body portion 330, whereas rod 520A may extend through both high pressure body portion 330 and low pressure body portion 310.

Within valve assembly 500A, regulator 520 may extend through a cavity 533 positioned substantially or entirely within high pressure body portion 330. A channel 533A may be disposed substantially or entirely within low pressure body portion 310, and may receive an end of rod 520A furthest from flange 520B. Valve assembly 500A may include a resilient member 530 (e.g., a spring) disposed within first cavity 533 and positioned between an internal (inward facing) surface of high pressure body portion 330 and a top (inward facing) surface of low pressure body portion 310. Resilient member 530 may be configured to be in an expanded state at rest as shown in FIG. 60A. Regulator 520 may further include a first gasket 522A coupled to and disposed about a circumferential exterior of flange 520B, a second gasket 522B coupled to and disposed about a circumferential exterior of rod 520A, and a third gasket 522C coupled to the axial end surface of rod 520A opposite of flange 520B.

In the example, first gasket 522A may be positioned within high pressure body portion 330, and third gasket 522C may be positioned with low pressure body portion 310. In the example, second gasket 522B may be coupled to a portion of rod 520A adjacent to the axial end surface of rod 520A such that second gasket 522B may be positioned within low pressure body portion 310. Accordingly, first gasket 522A may be configured to interface with an interior surface of first cavity 533, whereas second gasket 522B and third gasket 522C may be configured to interface with an interior surface of channel 533A. Regulator 520 may include a conduit 520C extending through rod 520A and flange 520B, with an opening 520D at the axial end surface of rod 520A and an opening 520E at an opposing end of flange 520B. Third gasket 522C may extend about opening 520D at the axial end surface of rod 520A.

Still referring to FIG. 60A, channel 533A may be in fluid communication with high pressure line 152 via an inlet 532A, and cavity 533 may be in fluid communication with atmospheric pressure via a first outlet 534A and with low pressure line 154 via a second outlet 536A. Channel 533A may be in communication with low pressure line 153 via cavity 533. Regulator 520 may be configured to minimize an accumulation of high pressure within auto-injector 400 from the use of pressurized fluid to deliver the fluid substance to a patient.

For example, in a pre-activated state of auto-injector 400 as shown in FIG. 60A, a propellant (e.g., pressurized gas) dispensed from fluid source 350 may flow through high pressure line 152. Some pressurized gas from high pressure line 152 may be diverted toward inlet 532A and into second channel 533A. Upon entering channel 533A, pressurized gas may enter opening 520D or conduit 520C, and ultimately out of opening 520E at an opposite end of conduit 520C. Gas may travel through conduit 520C in a first direction (from low pressure body portion 310 to high pressure body portion 330. Second gasket 522B may be configured to form a seal against the interior surface of channel 533A, and inhibit the pressurized gas (received from inlet 532A) from traveling about an exterior of rod 520A and moving from channel 533A toward cavity 533.

Referring now to FIG. 60B, after traveling through conduit 520C and exiting opening 520E, the pressurized gas may be received in cavity 533 and act on flange 520B (and regulator 520 generally) in an opposite direction (e.g., from high pressure body portion 330 toward low pressure body portion 310). First gasket 522A may be configured to form a seal against the interior surface of cavity 533, and inhibit the pressurized gas (received from conduit 520C) from traveling about an exterior of flange 520B and moving from cavity 533 toward first outlet 534A and/or channel 533A. The high pressure gas accumulating within cavity 533 (above first gasket 522A) and acting in the second, opposite direction, may compress resilient member 530. Any air and/or gas disposed within cavity 533 between first gasket 522A and second gasket 522B may exit high pressure body portion 330 via first outlet 534A as resilient member 530 is compressed.

With regulator 520 moved to the lowered position, as shown in FIG. 60B, third gasket 522C may be configured to form a seal against an interior surface of channel 533A, thereby inhibiting additional pressurized gas (received from inlet 532A) from being received through opening 520D and into conduit 520C. With resilient member 530 compressed, the pressurized gas causing the compression may exit cavity 533 at second outlet 536A, thereby reducing the pressure within cavity 533. The pressure difference within cavity 533 on opposing sides of flange 520B (and particularly first gasket 522A) may allow an energy stored by resilient member 530 (from its compression in cavity 533) to move regulator 520 back toward its initial configuration (see FIG. 60A) as resilient member 530 returns to an expanded configuration. Regulator 520 may continue to move (e.g., oscillate) within cavity 533 as high pressurized gas is received in cavity 533 (via conduit 520C) and released from cavity 533 (via second outlet 536A), thereby causing resilient member 530 to compress and expand when an equilibrium state is achieved.

The pressurized gas exiting cavity 533 at second outlet 536A may be directed to low pressure line 154 and may work through the system in substantially the same manner as described with respect to FIGS. 2A-2C.

Referring now to FIGS. 61A-61B, an alternative valve assembly 600A of auto-injector 400 is depicted. Valve assembly 600A may be substantially similar to valve assembly 300A described herein. For example, valve assembly 600A may include a low pressure body portion 310 and a high pressure body portion 330. Valve assembly 600A may be operatively coupled to fluid conduit 280 via container 370. In the example, valve assembly 600A may include a regulator 620 positioned within high pressure body portion 330. Regulator 620 may be a piston including a body 620A and a rod 620B extending from body 620A. Body 620A and rod 620B may be disposed within, and moveable relative to, high pressure body portion 330.

Regulator 620 may include a first gasket 622A disposed about an upper portion of body 620A, and a second gasket 622B disposed about an intermediate portion of body 620A. The upper portion of body 620A may be positioned adjacent to rod 620B relative to the intermediate portion of body 620A. Regulator 620 may further include a bottom flange 624 extending outwardly (downward) from a bottom portion of body 620A.

As seen in FIG. 61A, bottom flange 624 may be configured to abut against a top (inward facing) surface of low pressure body portion 310 when regulator 620 is in an initial, default configuration. As described in detail herein, bottom flange 624 may be configured to surround and/or block an opening of a channel (second channel 633B) of low pressure body portion 310 when regulator 620 is in the default position, thereby inhibiting fluid communication between high pressure body portion 330 and low pressure body portion 310.

Within valve assembly 600A, regulator 620 may extend through a first channel 633A positioned entirely within high pressure body portion 630. First gasket 622A and second gasket 622B may be configured to interface with an interior surface of first channel 633A when each respective gasket is aligned with an upper portion of first channel 633A having a first diameter. High pressure body portion 330 may include a recessed wall 602 extending along a lower portion of first channel 633A that is adjacent to low pressure body portion 310. Recessed wall 602 may define a cut out along a sidewall of first channel 633A, such that first channel 633A may have a second diameter along the lower portion that is greater than the first diameter of the upper portion of first channel 633A.

In a default position, body 620A may be positioned adjacent to low pressure body portion 310 with first gasket 622A positioned relatively above inlet 632A and second gasket 622B positioned in alignment with recessed wall 602. First gasket 622A may be engaged with the interior surface of first channel 633A when body 620A is in the default position due to first gasket 622A being positioned in alignment with the upper portion of first channel 633A (having the first (smaller) diameter). Second gasket 622B may be disengaged and spaced apart from the interior surface of first channel 633A when body 620A is in the default position due to second gasket 622B being positioned in alignment with the lower portion of first channel 633A (having the second (greater) diameter) along the recessed wall 602.

A second channel 633B may be disposed entirely within low pressure body portion 310, and may be in fluid communication with first channel 633A when regulator 620 is in a raised position (FIG. 61B). Valve assembly 600A may include a resilient member 630 (e.g., a spring) disposed within first channel 633A. Resilient member 630 may be disposed about rod 620B, and positioned between an internal (inward facing) surface of high pressure body portion 330 and a top (inward facing) surface of low pressure body portion 310. Resilient member 630 may be configured to be in an expanded state at rest, as shown in FIG. 61A. In the expanded state, body 620A may be in the default position with second gasket 622B aligned with the recessed channel 602 and bottom flange 624 engaged against the top (inward facing) surface of low pressure body portion 310. When engaged with low pressure body portion 310, bottom flange 624 may be configured to extend around and seal the second channel 633B from the first channel 633A.

Still referring to FIG. 61A, first channel 633A may be in fluid communication with high pressure line 152 via an inlet 632A, and second channel 633B may be inhibited from fluid communication with high pressure line 152 via regulator 620. Second channel 633B may be in fluid communication with low pressure line 154 via an outlet 634A. Regulator 620 may be configured to minimize an accumulation of high pressure within auto-injector 400 from the use of pressurized fluid to deliver the fluid substance to a patient.

For example, in a pre-activated state of auto-injector 400, a propellant (e.g., pressurized gas) dispensed from fluid source 350 may flow through high pressure line 152. Some pressurized gas from high pressure line 152 may be diverted toward inlet 632A and into first channel 633A. Upon entering first channel 633A, pressurized gas may flow about an exterior of body 620A between first gasket 622A and second gasket 622B. With regulator 620 in a default position and resilient member 630 in the expanded state, second gasket 622B may be positioned in alignment with the recessed channel 602. Accordingly, the pressurized gas may flow beyond second gasket 622B and toward second channel 633B via the recessed wall 602.

The pressurized gas may travel in a first (downward) direction (e.g., from high pressure body portion 330 toward low pressure body portion 310). With bottom flange 624 sealing the second channel 633B, the pressurized gas may accumulate within the lower portion of first channel 633A and beneath body 620A. In this instance, the pressurized gas may act on body 620A (and regulator 620 generally) in a second (upward) direction (e.g., from low pressure body portion 310 toward high pressure body portion 330). The high pressure gas acting in the second, opposite direction may cause regulator 620 to translate, thereby compressing resilient member 630. As resilient member 630 is compressed and regulator 620 moves upward within first channel 633A, at least a portion of rod 620B may extend outwardly from high pressure body portion 330 through an opening 604.

The pressurized gas received in first channel 633A is inhibited from exiting opening 604 due to a continuous seal formed against the interior surface of first channel 633A by first gasket 622A. It should be understood that the portion of first channel 633A positioned above first gasket 622A may be maintained at atmospheric pressure given opening 604. The pressurized gas may cause bottom flange 624 to disengage the top (inward facing) surface of low pressure body portion 310. In this instance, second channel 633B may establish fluid communication with first channel 633A upon bottom flange 624 moving upward relative to high pressure body portion 330, as seen in FIG. 61B. Further, second gasket 622B may move upward and interface with the interior surface of the upper portion of first channel 633A. Accordingly, second gasket 622B may be configured to inhibit fluid communication between inlet 632A and low pressure body portion 310 by forming a seal within first channel 633A.

With regulator 620 moved from the default position (FIG. 61A) to the raised position (FIG. 61B), outlet 634A may be in fluid communication with the high pressure gas stored and accumulated within first channel 633A below second gasket 622B. With resilient member 630 compressed, the pressurized gas causing the compression may exit first channel 633A at outlet 634A via second channel 633B, thereby reducing the pressure within first channel 633A. The pressure difference within first channel 633A on opposing sides of body 620A may allow an energy stored by resilient member 630 (from its compression in first channel 633A) to move regulator 620 back toward the default position (FIG. 61A) as resilient member 630 returns to an expanded configuration. Regulator 620 may continue to move (e.g., oscillate) within first channel 633A as high pressurized gas is received in high pressure body portion 330 (via inlet 632A) and released from low pressure body portion 310 (via outlet 634A), thereby causing resilient member 630 to compress and expand when an equilibrium state is achieved.

The pressurized gas exiting first channel 633A at outlet 634A via second channel 633B may be directed to low pressure line 154, and may work through the system in substantially the same manner as described with respect to FIGS. 2A-2C.

Figure 62:
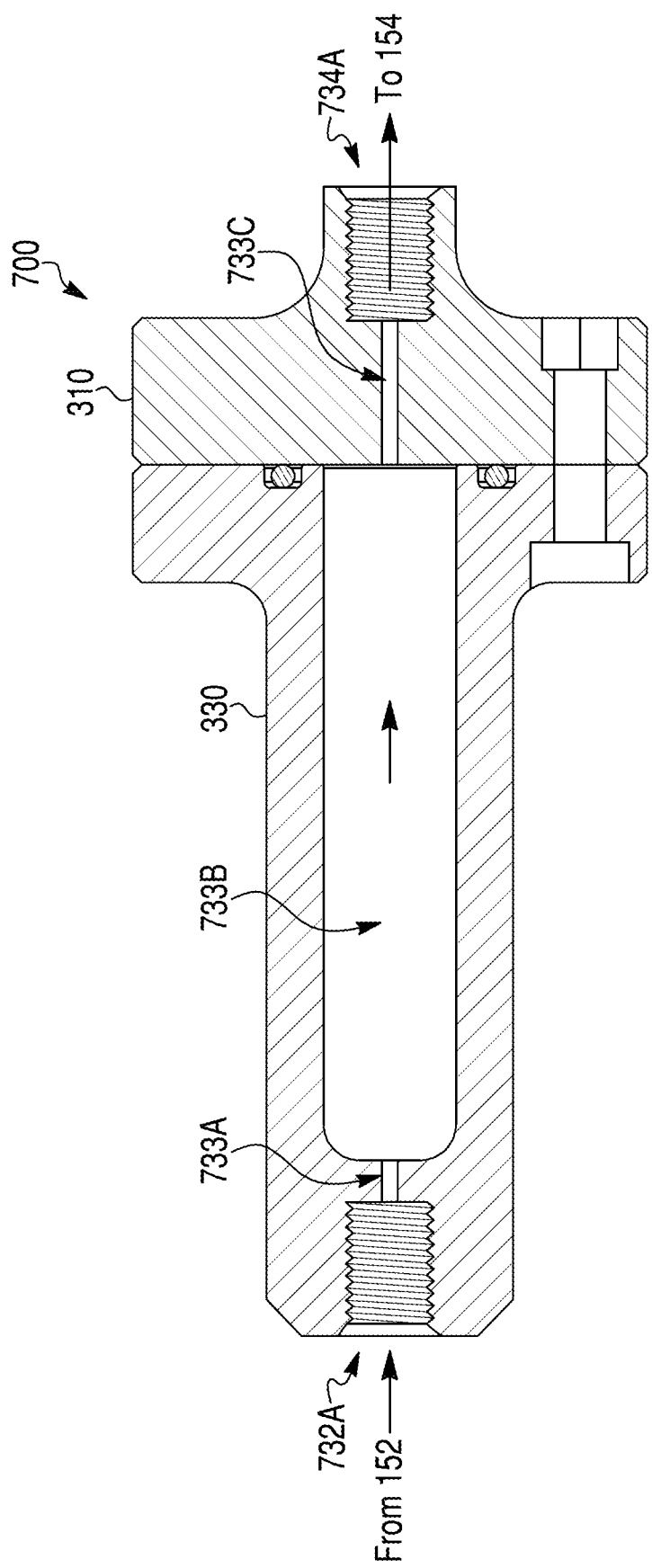
FIG. 62 is a schematic illustration of a volume accumulator of an auto-injector, according to an example of the disclosure.

Referring now to FIG. 62, a volume accumulator assembly 700 of auto-injector 400 is depicted. In some embodiments, volume accumulator assembly 700 may be included in auto-injector 400 in addition to and/or in lieu of the one or more of valve assemblies 300A, 500A, 600A shown and described above. Volume accumulator assembly 700 may include high pressure body portion 330 and low pressure body portion 310, with an inlet 732A in fluid communication with high pressure body portion 330 and an outlet 734A in fluid communication with low pressure body portion 310.

Volume accumulator assembly 700 may further include a first channel 733A and a cavity 733B disposed substantially or entirely within high pressure body portion 330, and a second channel 733C disposed substantially or entirely within low pressure body portion 310. First Channel 733A may be in fluid communication with inlet 732A, and second channel 733C may be in fluid communication with outlet 734A. Cavity 733B may be positioned between and have a cross-sectional profile (e.g., diameter) that is greater than each of first channel 733A and second channel 733C. First channel 733A and second channel 733C may have substantially similar and/or different cross-sectional profiles relative to one another.

Volume accumulator assembly 700 may be configured to passively minimize an accumulation of high pressure within auto-injector 400, from the use of pressurized fluid to deliver the fluid substance to a patient, without the use of an active regulator. In other words, volume accumulator assembly 700 may be configured to regulate the pressure within auto-injector 400. For example, in a pre-activated state of auto-injector 400, a propellant (e.g., pressurized gas) dispensed from fluid source 350 may flow through high pressure line 152. Some pressurized gas from high pressure line 152 may be diverted toward inlet 732A and into first channel 733A. Upon entering the relative narrow conduit of first channel 733A, the high pressure gas may be directed toward cavity 733B, which may have a greater volume than first channel 733A. In this instance, the gas may be transitioned to a relatively lower pressure as the gas enters cavity 733B and moves through the expanded space.

It should be appreciated that a volume of cavity 733B may influence a rate and/or degree at which the pressure of the gas is lowered by volume accumulator assembly 700. For example, and for illustrative purposes only, the pressurized gas from high pressure line 152 may include Argon (Ar), which may be received at inlet 732A at a pressure of about 1100 psi. With cavity 733B defining a volume of about 3 milliliters, volume accumulator assembly 700 may be configured to reduce the pressure of the gas to about 350 psi within cavity 733B. Upon moving toward a second end of cavity 733B, opposite a first end adjacent to first channel 733A, the low pressure gas may be directed into the relatively narrow conduit of second channel 733C and toward low pressure line 154.

In some embodiments, the low pressure gas received through outlet 734A may be further reduced as the gas travels through auto-injector 400. For example, at the conclusion of an injection procedure by auto-injector 400, the pressure of the gas may have decreased to about 200 psi.

Features enumerated above have been described within the context of particular embodiments. However, as one of ordinary skill in the art would understand, features and aspects of each embodiment may be combined, added to other embodiments, subtracted from an embodiment, etc. in any manner suitable to assist with controlled preparation and/or delivery of a drug.

While a number of embodiments are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

Embodiments of the present disclosure may include the following features:

Item 1. An auto-injector, comprising:
a container capable of comprising a medicament;
a shuttle coupled to the container and on a horizontal path with a first state and a second state;
an energy source configured to release energy to translate the container and to translate the shuttle, preferably the energy source is pressurized fluid from a can;
an impediment preventing horizontal movement of the shuttle before activation of the auto-injector; and
a needle having
a first end configured to extend out of the auto-injector, and
a second end configured to extend into the container, wherein the second end of the needle and the container are not in fluid communication with one another before activation of the auto-injector;
and the energy is released from the energy source after:
a. the auto-injector is activated; and
b. the shuttle moves along its path, whereby
i. the container and the second end of the needle are put into fluid communication with one another, and
ii. the first end of the needle extends out of the auto-injector.

Item 2. The auto-injector of Item 1, wherein activation of the auto-injector allows for movement of an actuator from its first location to its second location, whereby the actuator contacts a portion of the energy source, preferably a can, to release energy, preferably as a pressurized fluid.

Item 3. The auto-injector of Item 2, wherein the actuator is interlocked with the impediment before the auto-injector is activated.

Item 4. The auto-injector of Item 3, wherein movement of the actuator from its first location to its second location is horizontal and, the release of energy from the energy source causes the shuttle to move horizontally from its first state to its second state.

Item 5. The auto-injector of Item 4, further including:
a driver that can traverse the auto-injector vertically, is coupled to the needle, and has a first position, a second position, and a third position; and
a gear movable by the shuttle,
wherein horizontal movement of the shuttle from its first state toward its second state causes the gear to rotate and the driver to move vertically from its first position to its second position, and the vertical movements and horizontal movements are substantially perpendicular to one another.

Item 6. The auto-injector of Item 5, further including a housing enclosing the container, the shuttle, the energy source, and at least a portion of the needle, wherein the first end of the needle is positioned:
within the housing when the driver is in the first position;
outside of the housing when the driver is in the second position; and
within the housing when the driver is in the third position.

Item 7. The auto-injector of Item 5, wherein the actuator at its first location comprises
a resilient member that is movable from a first energy-storing state to a first energy-released state and is capable of translating the actuator from its first location to its second location, respectively.

Item 8. The auto-injector of Item 7, wherein upon release of the energy, preferably a pressurized fluid from the energy source, the resilient member is moved from its first energy-released state toward a second energy-storing state by the shuttle and by the actuator, causing vertical translation of the first end of the needle to outside of the housing.

Item 9. The auto-injector of Item 8, wherein after a threshold amount of energy is released, the resilient member is moved from the second energy-storing state toward a second energy-released state, causing vertical translation of the first end of the needle into the housing.

Item 10. The auto-injector of Item 9, wherein after the threshold amount of energy is released, movement of the resilient member from the second energy-storing state toward the second energy-released state, urges the shuttle to move in the horizontal direction from its second state toward its first state, causing rotation of the gear in a second rotational direction that is opposite of the first rotational direction, thereby causing the driver to move vertically from the second position, to the third position.

Item 11. The auto-injector of Item 8, wherein the first energy-storing state and the second energy-storing state are the same location within the housing.

Item 12. The auto-injector of Item 8, wherein the first energy-storing state and the second energy-storing state are different locations within the housing.

Item 13. The auto-injector of Item 9, wherein the first energy-released state and the second energy-released state are the same location within the housing.

Item 14. The auto-injector of Item 9, wherein the first energy-released state and the second energy-released state are different locations within the housing.

Item 15 The auto-injector of Item 7, wherein the resilient member is a spring.

Item 16. The auto-injector of Item 15, wherein the spring is the only spring contained within the auto-injector.

Item 17. The auto-injector of Item 15, wherein the energy-storing state is a compressed position of the spring, and the energy-release state is an expanded position of the spring.

Item 18. The auto-injector of Item 2, further including a resilient member, movable from an energy-storing state to an energy-released state, wherein the resilient member moves the activator from the first location to the second location by moving from the energy-storing state to the energy-released state.

Item 19. The auto-injector of Item 18, wherein the resilient member is moved from the energy-released state toward another energy-storing state by the shuttle and by the activator upon release of energy, preferably pressurized fluid from the fluid source.

Item 20. The auto-injector of Item 19, wherein after a threshold amount of pressurized fluid is released from the fluid source, the resilient member is moved from the second energy-storing state toward its second energy-released state, causing translation of the first end of the needle into an interior of the auto-injector.

Item 21. The auto-injector of Item 1, wherein energy released from the energy source acts against the container and moves the container into fluid communication with the needle.

Item 22. The auto-injector of Item 1, wherein before the auto-injector is activated, a first stop prevents the shuttle from moving and prevents the container from moving into fluid communication with the needle.

Item 23. The auto-injector of Item 22, wherein the first stop abuts a surface of the shuttle before the auto-injector is activated.

Item 24. The auto-injector of Item 1, wherein the auto-injector is activated by a button configured to be depressed by a user.

Item 25. An auto-injector, comprising:
a container capable of comprising a medicament;
an energy source that is configured to translate the container and a shuttle within the auto-injector, wherein the energy source is preferably a pressurized fluid;
a needle having a first end configured to extend out of the auto-injector, and a second end configured to extend into the container, wherein, before activation of the auto-injector, the second end of the needle and the container are not in fluid communication with one another; and
a resilient member movable between an energy-storing state and an energy-released state, wherein 1) a first movement of the resilient member from the energy-storing state to the energy-released state can cause a release of pressurized fluid from the energy source, that results in 2) a second movement of the resilient member from its energy-released state toward a second energy-storing state, followed by 3) a third movement of the resilient member toward a second energy-released state that causes the first end of the needle to retract into the auto-injector from outside of the auto-injector.

Item 26. The auto-injector of Item 25, wherein the resilient member is a spring.

Item 27. The auto-injector of Item 26, wherein the spring is the only spring contained within the auto-injector.

Item 28. The auto-injector of Item 5, wherein the gear moveable by the shuttle includes:
a first gear portion and a second gear portion that rotate about a same axis, wherein the first gear portion and the second gear portion have different diameters.

Item 29. The auto-injector of Item 28, wherein the first gear portion has a larger diameter than the second gear portion.

Item 30. The auto-injector for Item 28, wherein the second gear portion has a larger diameter than the first gear portion.

Item 31. The auto-injector of Item 28, wherein the driver further comprises a driver rack gear configured to engage with the first gear portion.

Item 32. The auto-injector of Item 31, wherein the shuttle further comprises a shuttle rack gear configured to engage with the second gear portion.

Item 33. The auto-injector of Item 22, wherein before the auto-injector is activated, a second stop prevents the button from being depressed by a user.

Item 34. The auto-injector of Item 33, further including a tab coupled to an outer surface of the auto-injector before the auto-injector is activated, wherein the tab includes the second stop.

Item 35. The auto-injector of Item 34, wherein the tab must be removed from the auto-injector to enable the button to be depressed by the user.

Item 36. The auto-injector of Item 1, further including a first indicator, wherein the first indicator is visible from outside of the housing before the auto-injector is activated.

Item 37. The auto-injector of Item 36, wherein the first indicator is positioned on the shuttle.

Item 38. The auto-injector of Item 37, further including a second indicator, wherein the second indicator is visible from outside of the housing only after the auto-injector is activated.

Item 39. The auto-injector of Item 38, wherein the second indicator is positioned on the shuttle, and is visible from outside of the housing only after the release of energy from the energy source moves the shuttle from the first state to the second state.

Item 40. The auto-injector of Item 38, further including a third indicator, wherein the third indicator is visible from outside the housing only after an injection performed by the auto-injector is complete.

Item 41. The auto-injector of Item 40, further including an indicator slide that is 1) uncoupled from the shuttle before activation of the auto-injector, and 2) becomes coupled to the shuttle when the shuttle moves from the first state to the second state, and wherein the third indicator is positioned on the indicator slide.

Item 42. The auto-injector of Item 41, wherein movement of the shuttle from the second state back toward the first state also moves the indicator slide in a same direction so that the third indicator is visible from outside of the auto-injector.

Item 43. The auto-injector of Item 8, wherein movement of the shuttle from its first state to its second state:

causes the shuttle to contact and push the actuator in the same direction;
transition the resilient member from its first energy-released state toward its second energy-storing state; and
causes movement of the driver and extension of the first end of the needle outside of the housing.

Item 44. The auto-injector of Item 10, wherein movement of the resilient member from the second energy-storing state toward the second energy-released state urges the actuator into direct contact with the shuttle during horizontal movement of the shuttle from its second state toward its first state to cause rotation of the gear and retraction of the first end of the needle into the auto-injector.

Item 45. The auto-injector of Item 22, wherein the auto-injector is activated by a button configured to be depressed by a user, and the button includes the first stop.

Item 46. The auto-injector of Item 6, wherein:
the housing includes a third stop;
the auto-injector further includes an indicator slide configured to facilitate visibility of an indicator from outside of the auto-injector; and
the third stop maintains a position of the indicator slide so that horizontal movement of the shuttle locks the shuttle to the indicator slide.

Item 47. The auto-injector of Item 1, further including a valve assembly coupled to the container, the valve assembly including a diaphragm having a unitary central body with an outer rim extending outwardly from the central body and about a periphery of the central body.

Item 48. The auto-injector of Item 47, wherein the diaphragm includes a raised portion located at a radially center position of the central body, the raised portion having a thickness protruding outward from the central body at a distance that is greater than an extension of the outer rim relative to the central body.

What is claimed is:

1. An auto-injector, comprising:
a container capable of comprising a medicament;
a shuttle coupled to the container and horizontally movable with the container on a horizontal path between a first position and a second position;
an energy source configured to release energy to translate the container and to translate the shuttle along the horizontal path from the first position to the second position, the energy source is pressurized fluid from a can;
an impediment preventing horizontal movement of the shuttle before activation of the auto-injector; and
a needle having
  a first end configured to extend out of the auto-injector, and
  a second end configured to extend into the container, wherein the second end of the needle and the container are not in fluid communication with one another before activation of the auto-injector;
and the energy is released from the energy source after:
  a. the auto-injector is activated; and
  b. the shuttle moves along the horizontal path, whereby
    i. the container and the second end of the needle are put into fluid communication with one another, and
    ii. the first end of the needle extends out of the auto-injector.

2. The auto-injector of claim 1, wherein activation of the auto-injector allows for movement of an actuator from its first location to its second location, whereby
  the actuator contacts a portion of the can, to release the pressurized fluid.

3. The auto-injector of claim 2, wherein the actuator is interlocked with the impediment before the auto-injector is activated.

4. The auto-injector of claim 3, wherein movement of the actuator from its first location to its second location is horizontal and, the release of energy from the energy source causes the shuttle to move horizontally along the horizontal path from its first position to its second position.

5. The auto-injector of claim 4, further including:
a driver that can traverse the auto-injector vertically, is coupled to the needle, and has a first position, a second position, and a third position; and
a gear movable by the shuttle,
  wherein horizontal movement of the shuttle from its first position toward its second position causes the gear to rotate and the driver to move vertically from the first position of the driver to the second position of the driver, and the vertical movements and horizontal movements are substantially perpendicular to one another.

6. The auto-injector of claim 5, further including a housing enclosing the container, the shuttle, the energy source, and at least a portion of the needle, wherein the first end of the needle is positioned:
within the housing when the driver is in the first position;
outside of the housing when the driver is in the second position; and
within the housing when the driver is in the third position.

7. The auto-injector of claim 5, wherein the actuator at its first location comprises
a resilient member that is movable from a first energy-storing state to a first energy-released state and is capable of translating the actuator from its first location to its second location, respectively.

8. The auto-injector of claim 7, wherein upon release of the energy from the energy source, the resilient member is moved from its first energy-released state toward a second energy-storing state by the shuttle and by the actuator, causing vertical translation of the first end of the needle to outside of the housing.

9. The auto-injector of claim 8, wherein after a threshold amount of energy is released, the resilient member is moved from the second energy-storing state toward a second energy-released state, causing vertical translation of the first end of the needle into the housing.

10. The auto-injector of claim 9, wherein after the threshold amount of energy is released, movement of the resilient member from the second energy-storing state toward the second energy-released state, urges the shuttle to move in the horizontal path from its second position toward its first position, causing rotation of the gear in a second rotational direction that is opposite of the first rotational direction, thereby causing the driver to move vertically from the second position of the driver, to the third position of the driver.

11. The auto-injector of claim 7, wherein the resilient member is a spring.

12. The auto-injector of claim 11, wherein the energy-storing state is a compressed position of the spring, and the energy-release state is an expanded position of the spring.

13. The auto-injector of claim 2, further including a resilient member, movable from an energy-storing state to an energy-released state, wherein the resilient member moves the actuator from the first location to the second location by moving from the energy-storing state to the energy-released state.

14. The auto-injector of claim 13, wherein the resilient member is moved from the energy-released state toward another energy-storing state by the shuttle and by the actuator upon release of the pressurized fluid from the energy source.

15. The auto-injector of claim 14, wherein after a threshold amount of the pressurized fluid is released from the energy source, the resilient member is moved from the second energy-storing state toward its second energy-released state, causing translation of the first end of the needle into an interior of the auto-injector.

16. The auto-injector of claim 1, wherein energy released from the energy source acts against the container and moves the container into fluid communication with the needle.

17. The auto-injector of claim 5, wherein the gear moveable by the shuttle includes:
   a first gear portion and a second gear portion that rotate about a same axis, wherein the first gear portion and the second gear portion have different diameters.

18. The auto-injector of claim 1, further including a valve assembly coupled to the container, the valve assembly including a diaphragm having a unitary central body with an outer rim extending outwardly from the central body and about a periphery of the central body.

19. The auto-injector of claim 18, wherein the diaphragm includes a raised portion located at a radially center position of the central body, the raised portion having a thickness protruding outward from the central body at a distance that is greater than an extension of the outer rim relative to the central body.

20. An auto-injector, comprising:
a container capable of comprising a medicament;
an energy source that is configured to translate the container and a shuttle within the auto-injector, wherein the energy source is a pressurized fluid;
a needle having a first end configured to extend out of the auto-injector, and a second end configured to extend into the container, wherein, before activation of the auto-injector, the second end of the needle and the container are not in fluid communication with one another;
an actuator configured to move from an extended position to a depressed position; and
a resilient member disposed inside a carrier that is engaged with the actuator when in the extended position, and movable between an energy-storing state and an energy-released state, the resilient member is maintained in the energy-storing state when the carrier is engaged with the actuator, and moved to the energy-released state when the actuator disengages the carrier upon moving to the depressed position;
wherein 1) a first movement of the resilient member from the energy-storing state to the energy-released state can cause a release of pressurized fluid from the energy source, that results in 2) a second movement of the resilient member from its energy-released state toward a second energy-storing state, followed by 3) a third movement of the resilient member toward a second energy-released state that causes the first end of the needle to retract into the auto-injector from outside of the auto-injector.

* * * * *